US 11,845,997 B2

(12) United States Patent
Wu et al.

(10) Patent No.: US 11,845,997 B2
(45) Date of Patent: Dec. 19, 2023

(54) BIOAEROSOL DETECTION SYSTEMS AND METHODS OF USE

(71) Applicant: University of Florida Research Foundation, Inc., Gainesville, FL (US)

(72) Inventors: Chang-Yu Wu, Gainesville, FL (US); Xiao Jiang, Gainesville, FL (US); Maohua Pan, Gainesville, FL (US); John Lednicky, Gainesville, FL (US); Alexandros Demetrios Theodore, Gainesville, FL (US); Zhonghui Hugh Fan, Gainesville, FL (US); Nima Afshar Mohajer, Baltimore, MD (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 669 days.

(21) Appl. No.: 17/104,525

(22) Filed: Nov. 25, 2020

(65) Prior Publication Data

US 2021/0102265 A1 Apr. 8, 2021

Related U.S. Application Data

(63) Continuation-in-part of application No. 16/089,099, filed as application No. PCT/US2017/026305 on Apr. 6, 2017, now Pat. No. 10,859,473.

(Continued)

(51) Int. Cl.
*C12Q 1/70* (2006.01)
*G01N 33/569* (2006.01)

(52) U.S. Cl.
CPC ......... *C12Q 1/70* (2013.01); *G01N 33/56983* (2013.01); *G01N 2333/11* (2013.01); *G01N 2333/165* (2013.01)

(58) Field of Classification Search
CPC ........ B01L 2200/12; B01L 2300/0825; B01L 2300/126; C12Q 1/6806; C12Q 1/70;
(Continued)

(56) References Cited

U.S. PATENT DOCUMENTS

2005/0000196 A1   1/2005  Schultz
2005/0244980 A1  11/2005  Hering et al.
(Continued)

FOREIGN PATENT DOCUMENTS

WO   2009094233 A9   7/2009

OTHER PUBLICATIONS

International Search Report and Written Opinion for PCT/US2017/026305 dated Jun. 27, 2017.
(Continued)

*Primary Examiner* — Jennifer Wecker
(74) *Attorney, Agent, or Firm* — Thomas | Horstemeyer, LLP

(57) ABSTRACT

Described herein are bioaerosol detection systems and methods of use. In embodiments of bioaerosol detection systems and methods of use as described herein, systems and methods detect one or more coronaviruses and/or one or more influenza strains. In embodiments, coronaviruses according to systems and methods as described herein are SARS-CoV-2 coronavirus. In embodiments, influenza strains and/or particles according to the present disclosure are H1N1 influenza.

20 Claims, 26 Drawing Sheets

Specification includes a Sequence Listing.

Related U.S. Application Data

(60) Provisional application No. 62/318,962, filed on Apr. 6, 2016.

(58) Field of Classification Search
CPC .............. C12Q 1/701; C12Q 2527/101; C12Q 2527/109; G01N 1/2202; G01N 1/42; G01N 2001/2223; G01N 2015/0046; G01N 2333/11; G01N 2333/165; G01N 33/56983
See application file for complete search history.

(56) References Cited

U.S. PATENT DOCUMENTS

| | | | |
|---|---|---|---|
| 2008/0236305 A1 | 10/2008 | Masset et al. | |
| 2009/0281442 A1* | 11/2009 | Paz | A61B 5/097 600/543 |
| 2010/0206094 A1 | 8/2010 | Shenderov | |
| 2011/0095095 A1 | 4/2011 | Hering et al. | |
| 2011/0111387 A1* | 5/2011 | Wu | G01N 15/06 435/5 |
| 2014/0029154 A1 | 1/2014 | Hering et al. | |
| 2014/0033915 A1 | 2/2014 | Hering et al. | |
| 2014/0158125 A1 | 6/2014 | O'Donnell et al. | |
| 2015/0024379 A1 | 1/2015 | Ensor et al. | |
| 2015/0345522 A1 | 12/2015 | Fong et al. | |
| 2016/0107137 A1 | 4/2016 | Hering et al. | |

OTHER PUBLICATIONS

Davis and Orlando (2018) "For flu detection, just add water" University of Florida News. Published Feb. 26, 2018 at http://news.ufl.edu/articles/2018/02/for-flu-detection-just-add-water.php. Accessed Sep. 27, 2018.

* cited by examiner

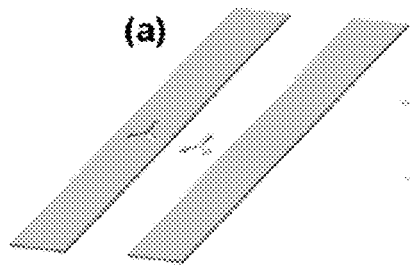
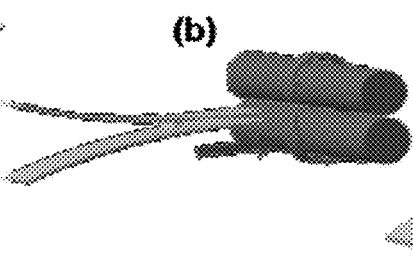
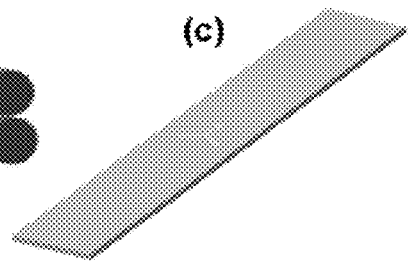
FIG. 3(a)　　　　　FIG. 3(b)　　　　　FIG. 3(c)
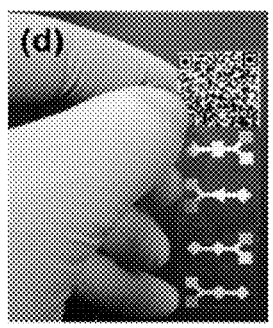
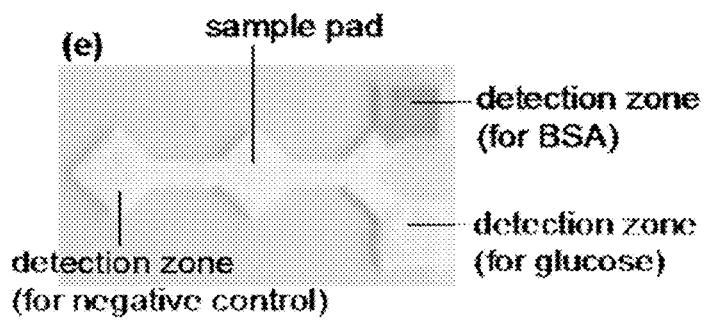
FIG. 3(d)　　　　　FIG. 3(e)

FIG. 4(a)    FIG. 4(b)

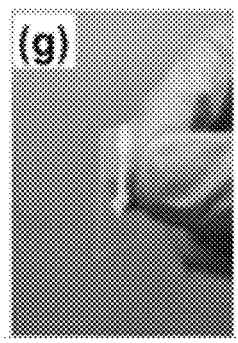
FIG. 13(g)
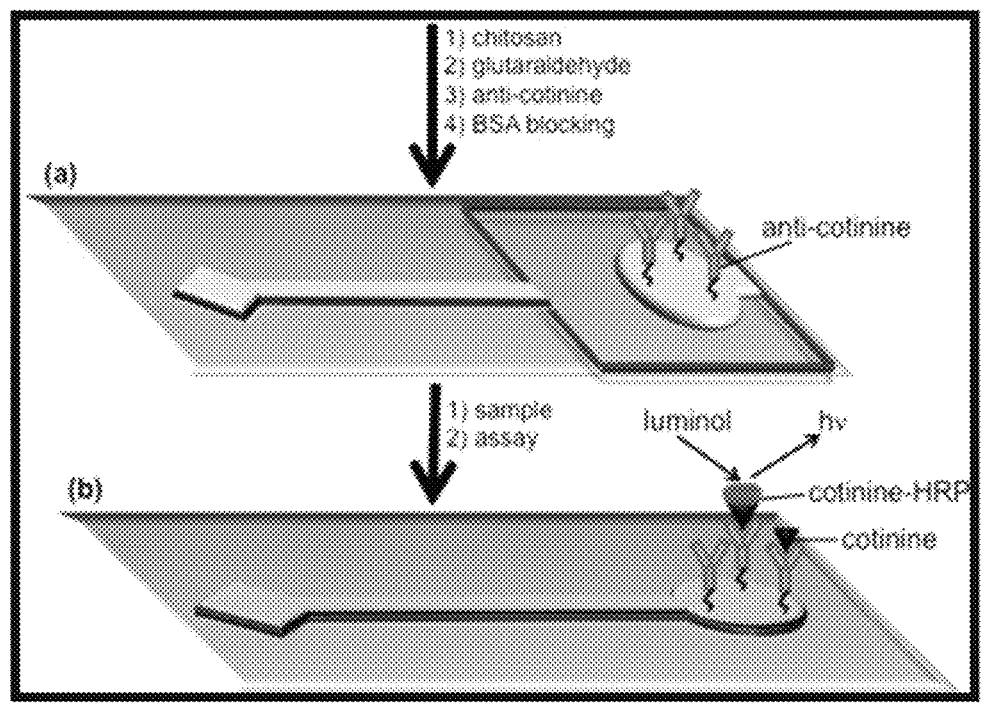
FIG. 14(a)
FIG. 14(b)

FIG. 16(a)
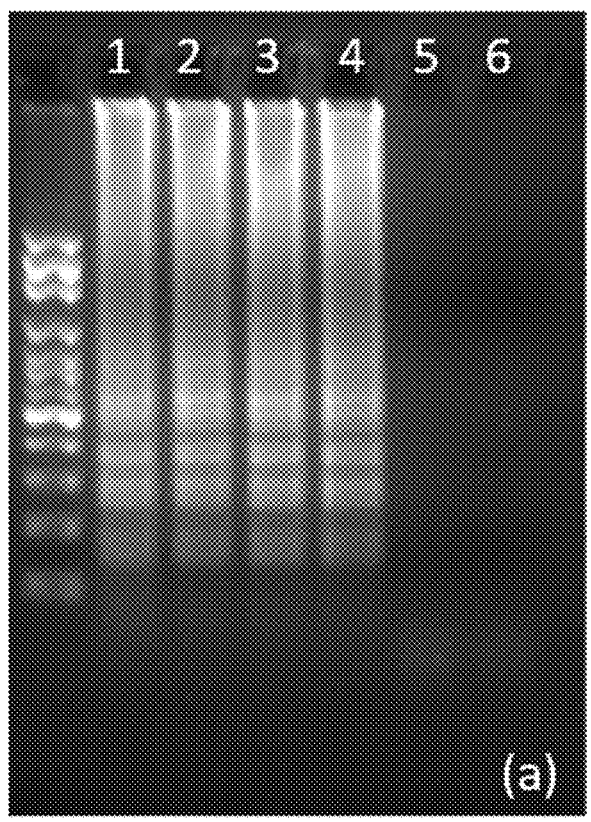
FIG. 16(b)
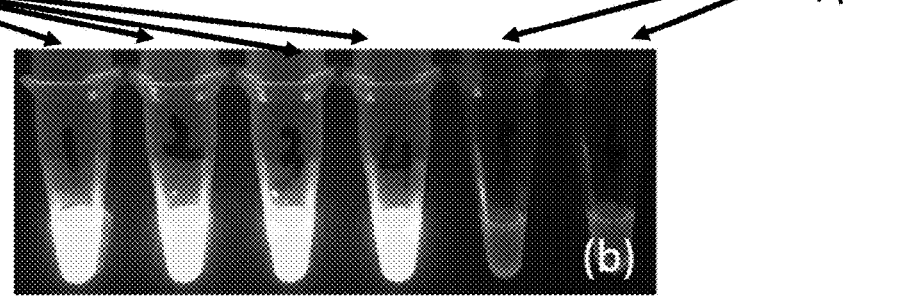
green — Red/pink
FIG. 16(c)
FIG. 16(d)
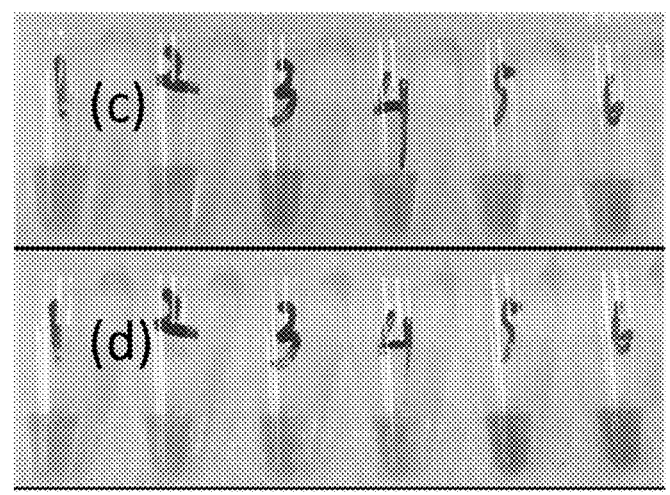

(a)

(b)

(a)

(b)

(c)

(d)

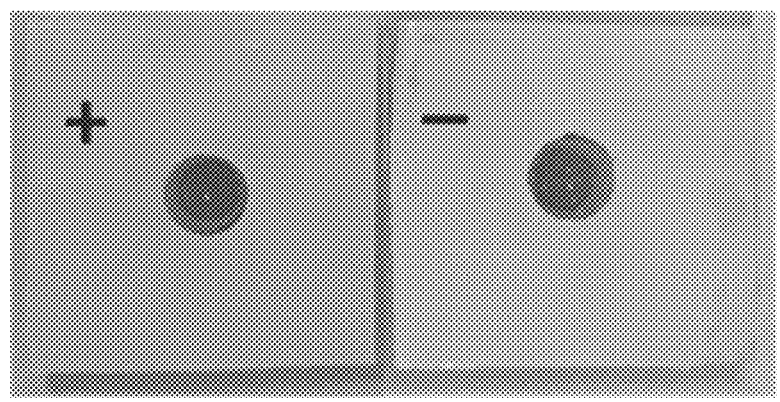
FIG. 23(a)
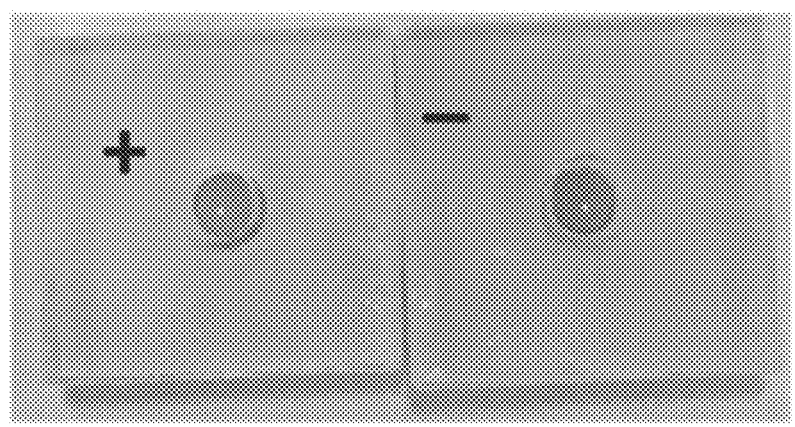
FIG. 23(b)
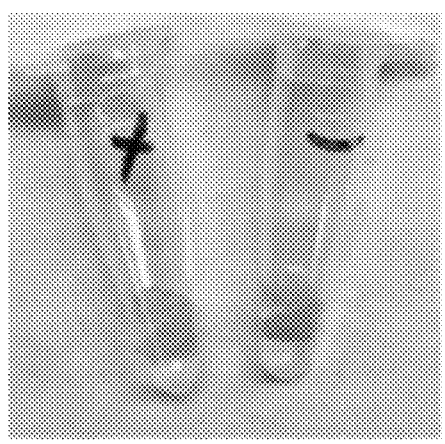 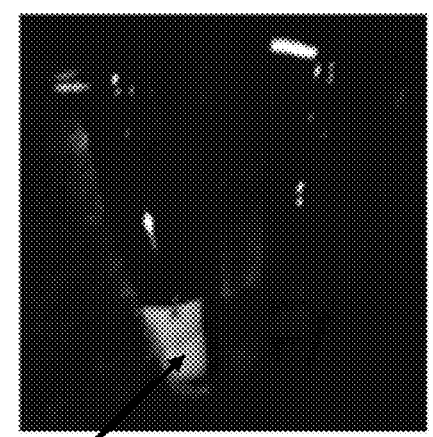
FIG. 23(c)　　　　　　　　FIG. 23(d)
Green fluorescence

SEQUENCE LISTING

<160> NUMBER OF SEQ ID NOS: 15

<210> SEQ ID NO 1
<211> LENGTH: 22
<212> TYPE: DNA
<213> ORGANISM: Artificial Sequence
<220> FEATURE:
<223> OTHER INFORMATION: SARS CoV-2 N Forward Primer

<400> SEQUENCE: 1
gggagcagag gcggcagtca ag                                    22

<210> SEQ ID NO 2
<211> LENGTH: 24
<212> TYPE: DNA
<213> ORGANISM: Artificial Sequence
<220> FEATURE:
<223> OTHER INFORMATION: SARS CoV-2 N Reverse Primer

<400> SEQUENCE: 2
catcaccgcc attgccagcc attc                                  24

<210> SEQ ID NO 3
<211> LENGTH: 25
<212> TYPE: DNA
<213> ORGANISM: Artificial Sequence
<220> FEATURE:
<223> OTHER INFORMATION: SARS CoV-2 N Probe

<400> SEQUENCE: 3
cctcatcacg tagtcgcaac agttc                                 25

<210> SEQ ID NO 4
<211> LENGTH: 18
<212> TYPE: DNA
<213> ORGANISM: Artificial Sequence
<220> FEATURE:
<223> OTHER INFORMATION: F3

<400> SEQUENCE: 4
tggaccccaa aatcagcg                                         18

<210> SEQ ID NO 5
<211> LENGTH: 20
<212> TYPE: DNA
<213> ORGANISM: Artificial Sequence
<220> FEATURE:
<223> OTHER INFORMATION: B3

<400> SEQUENCE: 5
agccaatttg gtcatctgga                                       20

<210> SEQ ID NO 6
<211> LENGTH: 40
<212> TYPE: DNA
<213> ORGANISM: Artificial Sequence
<220> FEATURE:
<223> OTHER INFORMATION: Forward inner primer (FIP)

<400> SEQUENCE: 6
cgttgttttg atcgcgcccc attacgtttg gtggaccctc                 40

<210> SEQ ID NO 7
<211> LENGTH: 41
<212> TYPE: DNA
<213> ORGANISM: Artificial Sequence

```
<220> FEATURE:
<223> OTHER INFORMATION: Backward inner primer (BIP)

<400> SEQUENCE: 7
atactgcgtc ttggttcacc gcattggaac gccttgtcct c                    41

<210> SEQ ID NO 8
<211> LENGTH: 22
<212> TYPE: DNA
<213> ORGANISM: Artificial Sequence
<220> FEATURE:
<223> OTHER INFORMATION: Forward loop primer (LF)

<400> SEQUENCE: 8
tgcgttctcc attctggtta ct                                         22

<210> SEQ ID NO 9
<211> LENGTH: 22
<212> TYPE: DNA
<213> ORGANISM: Artificial Sequence
<220> FEATURE:
<223> OTHER INFORMATION: Backward loop primer (LB)

<400> SEQUENCE: 9
tctcactcaa catggcaagg aa                                         22

<210> SEQ ID NO 10
<211> LENGTH: 22
<212> TYPE: DNA
<213> ORGANISM: Artificial Sequence
<220> FEATURE:
<223> OTHER INFORMATION: F3

<400> SEQUENCE: 10
accttctaga agacaagcat aa                                         22

<210> SEQ ID NO 11
<211> LENGTH: 14
<212> TYPE: DNA
<213> ORGANISM: Artificial Sequence
<220> FEATURE:
<223> OTHER INFORMATION: B3

<400> SEQUENCE: 11
tcctcataat cgat                                                  14

<210> SEQ ID NO 12
<211> LENGTH: 42
<212> TYPE: DNA
<213> ORGANISM: Artificial Sequence
<220> FEATURE:
<223> OTHER INFORMATION: Forward inner primer (FIP)

<400> SEQUENCE: 12
tggatttccc aggatccagc ggaaactatg caaactaaga gg                   42

<210> SEQ ID NO 13
<211> LENGTH: 38
<212> TYPE: DNA
<213> ORGANISM: Artificial Sequence
<220> FEATURE:
<223> OTHER INFORMATION: Backward inner primer (BIP)

<400> SEQUENCE: 13
tccacagcaa gctcatggtc tcctgggtaa cacgttcc                        38
```

```
<210> SEQ ID NO 14
<211> LENGTH: 19
<212> TYPE: DNA
<213> ORGANISM: Artificial Sequence
<220> FEATURE:
<223> OTHER INFORMATION: Forward loop primer (LF)

<400> SEQUENCE: 14
ccaaatgcaa tggggctac                                            19

<210> SEQ ID NO 15
<211> LENGTH: 26
<212> TYPE: DNA
<213> ORGANISM: Artificial Sequence
<220> FEATURE:
<223> OTHER INFORMATION: Backward loop primer (LB)

<400> SEQUENCE: 15
ctacattgtg gaaacatcta gttcag                                    26
```

BIOAEROSOL DETECTION SYSTEMS AND METHODS OF USE

CROSS-REFERENCE TO RELATED APPLICATION

This application is a continuation-in-part of U.S. Non-Provisional Utility Application entitled "BIOAEROSOL DETECTION SYSTEMS AND METHODS OF USE," having Ser. No. 16/089,099, and filed on Sep. 27, 2018, which is the 35 U.S.C. § 371 national stage application of PCT Application No. PCT/US2017/026305, filed Apr. 6, 2017, which claims priority to and the benefit of U.S. Provisional Application entitled "BIOAEROSOL DETECTION SYSTEMS AND METHODS OF USE," having Ser. No. 62/318,962, filed on Apr. 6, 2016, all of which are entirely incorporated herein by reference.

STATEMENT REGARDING FEDERALY SPONSORED RESEARCH OR DEVELOPMENT

This invention was made with government support under grant number DBI-1353423 and CBET-2030844 awarded by the National Science Foundation. The government has certain rights to the invention.

SEQUENCE LISTING

This application contains a sequence listing filed in electronic form as an ASCII.txt file entitled "(222110-1631) Sequence Listing_ST25.txt", created on Nov. 23, 2020 and having a size of 4 kb. The content of the sequence listing is incorporated herein in its entirety.

BACKGROUND

Existing bioaerosol sampling systems are designed for bacterial aerosol collection/detection based on inertia principles. They are very ineffective for viral aerosols because viruses are much smaller than bacteria and are not effectively captured by the equipment. In addition to being ineffective, conventional detection methods for viruses are time consuming and do not allow determination in field investigation. The present disclosure discusses systems and methods for bioaerosol detection, in particular viral aerosols, to address the aforementioned deficiencies and inadequacies.

SUMMARY

Described herein are embodiments of bioaerosol amplification and detection systems. Bioaerosol amplification and detection systems as described herein can be modular systems and can comprise a bioaerosol amplification unit comprising a chamber configured to receive air containing bioaerosols, wherein the chamber is further configured for adiabatic amplification of the bioaerosols; and a biosampler, wherein the biosampler is in fluid communication with the bioaerosol amplification unit, and wherein the biosampler is configured to receive and collect adiabatically amplified bioaerosols from the chamber of the bioaerosol amplification unit.

Additionally, embodiments of bioaerosol amplification and detection systems described herein can further comprise adiabatic amplification by adiabatic cooling. In certain embodiments, adiabatic cooling can further comprise swirling, mixing, or both, of air containing bioaerosols.

In certain embodiments, bioaerosol amplification and detection systems as described herein, can further comprise a bioaerosol analysis platform, wherein the bioaerosol analysis platform is configured to receive adiabatically amplified bioaerosols collected in the biosampler and configured to detect the adiabatically amplified bioaerosols by one or more bioaerosol detection assays. In certain embodiments, the bioaerosol analysis platform can be a microfluidic device comprising one or more bioaerosol detection assays configured to detect the adiabatically amplified bioaerosols.

In embodiments, the bioaerosols are coronavirus particles or influenza particles. In embodiments, the coronavirus particles are SARS-CoV-2 viral particles. In embodiments, the influenza particles are H1N1 viral particles. The viral particles of the bioaerosols can comprise one or more intact live viral particles.

In certain embodiments, bioaerosol amplification units as described herein can further comprise one or more interior surfaces of the chamber wetted with water having a temperature of about 35° C. to about 65° C., wherein the one or more surfaces is adjacent to the air containing bioaerosols.

In certain embodiments, the chamber further comprises cooled air containing bioaerosols having a temperature of about −40° C. to about 10° C. and steam having a temperature of about 35° C. to about 65° C. In certain embodiments, the chamber further comprises cooled air having a flow rate of about 0.1 Liters/min to about 10 Liters/min and steam having a flow rate of about 1 Liters/min to about 50 Liters/min.

In certain embodiments, the air containing bioaerosols can be cooled by a temperature drop within the chamber of the bioaerosol amplification unit, wherein the temperature drop is controlled by the ratio of the pressure of the air containing bioaerosols after adiabatic expansion to the pressure of the air containing bioaerosols before adiabatic expansion.

In certain embodiments, microfluidic devices of systems as described herein can be paper-based or laminated paper-based. In certain embodiments, one or more detection assays of systems described herein can comprise an immunoassay or a nucleic acid amplification assay, individually or in combination. In certain embodiments, bioaerosol amplification and detection systems as described herein can be configured to detect viruses.

Also described herein are methods of detecting amplified bioaerosols. Methods as described herein can comprise the steps of: providing a bioaerosol amplification and detection system comprising a bioaerosol amplification unit, a biosampler, and a bioaerosol analysis platform; delivering air containing bioaerosols to the bioaerosol amplification unit, wherein the bioaerosol amplification unit is configured to adiabatically amplify bioaerosols; adiabatically amplifying bioaerosols with the bioaerosol amplification unit; delivering amplified bioaerosols from the bioaerosol amplification unit to the biosampler; precipitating, concentrating, or both the amplified bioaerosols into a collection reservoir of the biosampler; delivering the collected amplified bioaerosols from the collection reservoir of the biosampler to a bioaerosol analysis platform, wherein the bioaerosol analysis platform is configured to detect one or more collected amplified bioaerosols or components thereof with one or more detection assays; and detecting collected amplified bioaerosols or bioaerosol components with one or more detection assays. Adiabatic amplification in methods as described herein can be adiabatic cooling, and in certain embodiments can include swirling and mixing of air containing bioaerosols.

In certain embodiments of methods as described herein, one or more detection assays used in the methods can be one or more nucleic acid detection assays or one or more immunoassays, individually or in combination and the assays can be configured to detect one or more viruses. The viruses can be coronaviruses and/or influenza viruses. In embodiments, the coronaviruses are SARS-CoV-2. In embodiments, the influenza viruses are H1N1 flu virus.

In certain embodiments of methods as described herein the biosampler can further comprise a collection media. In certain embodiments of methods described herein, the air containing bioaerosols is cooled by a temperature drop within the bioaerosol amplification unit, wherein the temperature drop is controlled by the ratio of the pressure of the air containing bioaerosols after adiabatic expansion to the pressure of the air containing bioaerosols before adiabatic expansion.

In certain embodiments of methods as described herein the air containing bioaerosols can be cooled within a chamber of the bioaerosol amplification unit, wherein the chamber of the bioaerosol amplification unit has one or more interior surfaces adjacent to the air containing bioaerosols, wherein the one or more surfaces are wetted with warm water.

In certain embodiments of methods as described herein the chamber can be configured so that the volume of the chamber can be reduced by compression and expanded by decompression.

In certain embodiments of methods as described herein the biosampler can be functionally integrated into the chamber of the bioaerosol amplification unit and the chamber is configured for collection of amplified bioaerosols.

In embodiments, the coronavirus particles are SARs-COV-2 particles. In embodiments, the influenza particles are H1N1 particles. In embodiments, the nucleic detection assay is real-time reverse-transcriptase polymerase chain reaction or reverse transcription loop-mediated isothermal amplification.

BRIEF DESCRIPTION OF THE DRAWINGS

Many aspects of the disclosed devices and methods can be better understood with reference to the following drawings. The components in the drawings are not necessarily to scale, emphasis instead being placed upon clearly illustrating the relevant principles. Moreover, in the drawings, like reference numerals designate corresponding parts throughout the several views.

FIGS. 1(a)-(b) illustrates traditional bioaerosol capture principles.

FIG. 2 shows collection efficiency of traditional bioaerosol samplers as a function of particle diameter.

FIGS. 3(a)-(e) demonstrates a fabrication process for a Laminated Paper-based Analytical Device (LPAD).

FIGS. 4(a)-(b) illustrate: a) a diagram of a bioaerosol amplification unit (BAU) together as described herein in fluid communication with b) a biosampler as described herein.

FIGS. 13(a)-(g) shows an embodiment of a paper-based microfluidic device according to the present disclosure and a method of fabrication.

FIGS. 14(a)-(b) demonstrates an embodiment of device preparation and a chemiluminescence-based immunoassay protocol for sample detection according to the present disclosure.

FIGS. 16(a)-(d) shows typical flu virus reverse transcription loop-meditated isothermal amplification (RT-LAMP) reactions and colorimetric detection thereof.

FIG. 21(a) shows layers and construction of a device and FIG. 21(b) is a photograph depicting an embodiment of a device.

FIGS. 23(a)-(d) demonstrate an embodiment of in-device colorimetric H1N1 flu virus detection using phenol red and SYBR Green I DYE and the device of FIG. 21. "+" marks sample[s] positive for H1N1 and "−" marks samples negative for H1N1. FIG. 23(a) is a photograph showing two devices with phenol red RT-LAMP buffer before incubation. FIG. 23(b) shows the devices of FIG. 23(a) after incubation, positive sample device turns to orange (left) from pink (right). FIG. 23(c) shows the RT-LAMP buffer incubated in the device of FIGS. 23(a) and 23(b) under ambient light after adding SYBR Green I dye. FIG. 23(d) shows the two samples of FIG. 23(c) observed under a blue LED flashlight. The positive sample (left) has a green fluorescence.

FIGS. 24(a)-(d) show a schematic diagram of an embodiment of a BADS (a Batch Adiabatic-expansion for Size Intensification by Condensation, or BASIC), sampler, its operation, and the experimental system setup.

FIG. 25. shows Particle size distribution of aerosol from BASIC in comparison with source aerosol, without adiabatic expansion and with adiabatic expansion at different compression pressures.

FIGS. 26(a)-(b) illustrate a comparison of particle number concentration and CMD of supermicron particles under different compression pressure levels.

DETAILED DESCRIPTION

Figures 5A, 5B:
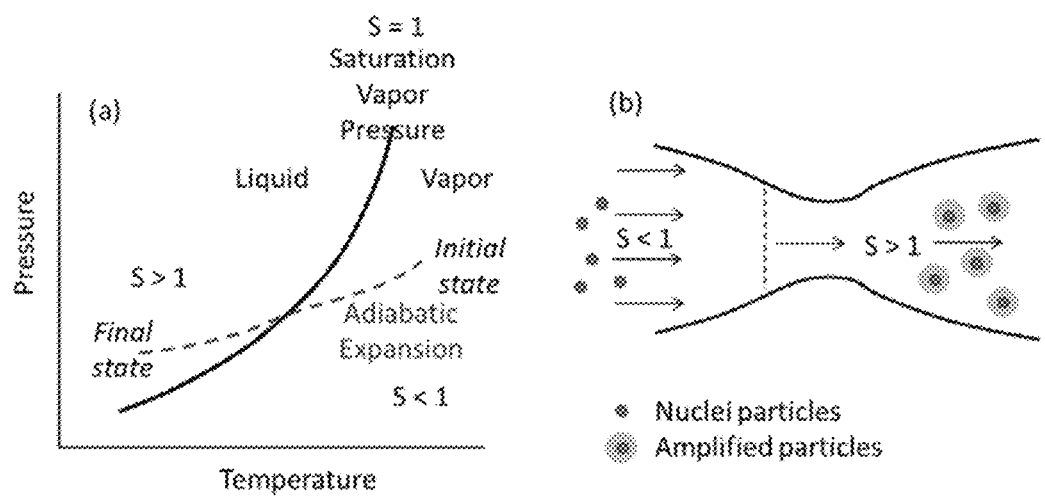
FIGS. 5(a)-(b) shows how adiabatic cooling can be used to create supersaturation.

Before the present disclosure is described in greater detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit (unless the context clearly dictates otherwise), between the upper and lower limits of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, inorganic chemistry, material science, and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is in atmosphere. Standard temperature and pressure are defined as 25° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

Discussion

Embodiments of the present disclosure provide for bioaerosol amplification and detection systems, bioaerosol analysis platforms, methods of using bioaerosol analysis platforms, bioaerosol amplification units, methods of using bioaerosol amplification units, biosamplers, methods of using biosamplers, method of detecting amplified aerosols, and the like. Embodiments of the present disclosure provide for highly efficient and rapid bioaerosol (e.g., viral bioaerosol) detection, or detection of bioaerosol components (e.g., nucleic acids, proteins, lipids, carbohydrates, or other surface or non-surface antigens).

Monitoring and detection of airborne bioaerosols is of great importance. There is especially a need for unattended monitoring of airborne viruses in the ambient air and in-situ assessment of contaminated locations all call for development of a rapid bioaerosol detection instrument that is capable of functioning effectively outside the controlled laboratory conditions. Such a capability will be instrumental in protecting the health and security of humans in military camps, public areas, schools, hospitals, airports, conflict zones and so on.

Embodiments of the present disclosure can have applications in public health, environmental health and medicine studies. It will facilitate real-time indoor air quality sampling in critical environments such as hospitals, clinics, emergency and clean rooms. It will also help diagnosing viral aerosol existing inside the exhaled breath.

Traditional air sampling and monitoring systems and methods can be inefficient, inaccurate, and unsuitable when it comes to detecting and analyzing small bioaerosols on the nano-meter scale. There is a need for improved devices and methodology.

In general, embodiments of the present disclosure are directed to a bioaerosol amplification and detection system (BADS). BADS of the present disclosure can comprise one or more modules, for example a bioaerosol amplification unit (BAU), a biosampler, and/or a bioaerosol analysis platform (BAP). In certain embodiments, a BADS can comprise a BAU and a biosampler. In certain embodiments, a BADS can comprise a BAU, a biosampler, and a BAP. In certain embodiments, two or more modules can be integrated into a single module, for example a module can be present which is comprised of an integrated BAU and biosampler.

One skilled in the art will recognize that the modular systems described herein can be realized through various combinations and configurations of modules, and that modules with different functions can be integrated, and embodiments of BADS as described herein should not be construed as limited to configurations only as described herein. Further, although much discussion is directed towards bioaerosols, it will be readily apparent to one skilled in the art that devices and methods as described herein can be applied to the amplification and detection of non-biological, organic or inorganic aerosols as well.

An embodiment of the present amplified bioaerosol detection system uses a BAU that can utilize adiabatic cooling/expansion, swirling/mixing, and wetted walls in combination to amplify bioaerosols. Swirling, mixing, or both can be optional and may not be necessary for efficient adiabatic amplification by adiabatic cooling/expansion. Swirling/mixing may improve amplification efficiency in certain embodiments. Wetted walls can also be an optional feature of systems described herein. In certain embodiments, adiabatic cooling/expansion can be accomplished with compression/decompression of air containing bioaerosols.

In an embodiment of the present BADS, air containing bioaerosols can be drawn into the BAU and then amplified. After amplification by the BAU within the amplified aerosol detection system, bioaerosols can be sent to a collection reservoir in a biosampler that collects amplified bioaerosol particles. The collection reservoir within the biosampler of the BADS can contain a collection media/medium that can preserve bioaerosols, amplified bioaerosols, or components thereof suitable for detection and/or analysis. The BADS or components thereof can be modified to improve concentration of collected bioaerosols if needed. A device, such as an impinger or electrostatic precipitator for example, can be used to aid collection if necessary, within the biosampler of the BADS.

Bioaerosols as described herein can be a fungi, bacteria, mycotoxin, or virus or groupings thereof. A bioaerosol can be a fungal cell such as a spore, mold, and/or yeast, and can be active or inactive. A bioaerosol can be a gram-positive or gram-negative bacteria and can be a rod-, sphere-, or spiral-shaped prokaryote. A bacterial bioaerosol can be a small bacteria of sub-micrometer size such as a bacteria of the genus *Mycoplasma* or an otherwise ultramicrobacteria.

In an embodiment, the bioaerosol can be a virus. A viral bioaerosol can be a DNA or an RNA virus, and can have a genome, a capsid, and optionally an envelope. The genome can include a single stranded RNA or DNA or double stranded RNA or DNA. The genome can be positive sense or negative sense if it is single stranded. A bioaerosol can be an MS2 bacteriophage or an influenza virus. A viral bioaerosol can have a variety of shapes, and the shape of the viral bioaerosol should be construed as limiting with regards to the discussion herein. In embodiments according to the present disclosure, a bioaerosol is a coronavirus. In embodiments according to the present disclosure, a bioaerosol is a SARs-CoV-2 coronavirus. A bioaerosol can be particles of or can otherwise comprise middle east respiratory syndrome coronavirus (MERS-CoV), and four other human coronaviruses (HCoVs) including HCoV-229E, HCoV-OC43, HCoV-NL63, and HCoV-HKU1. In embodiments according to the present disclosure, an influenza virus is a H1N1 influenza virus. An influenza virus can be one of four types of influenza viruses (A, B, C, and D). A bioaerosol can be particles of or can otherwise comprise one type or subtype of these viruses, or a combination of these viruses.

Bioaerosol structure and function can be conveyed with components such as proteins, nucleic acids, lipids, and/or carbohydrates for example. These components can be detected by detection assays. Components of bioaerosols that can be detected can be present on the bioaerosol surface, linked to the surface, in the interior of a bioaerosol (inside a capsid, wall, or membrane), in an envelope, or can be a constituent of a capsid, cell wall, envelope or membrane for example. Bioaerosol lysis can be used to detect interior bioaerosol components that reside within a capsid, cell wall, membrane, or envelope. Air containing bioaerosols may contain non-biological aerosols, which may be amplified by the present system.

After amplified bioaerosols are collected in the biosampler of the BADS, the BADS can use a BAP to detect bioaerosols or components thereof. Embodiments of the BAP incorporate nucleic acid detection assays and/or immunoassays into the BADS to detect bioaerosols, such as viruses, or bioaerosol components (proteins, nucleic acids, etc). Embodiments of the BAP of the BADS can use a device for bioaerosol detection. The device can be a microfluidic device, which are excellent platforms for detection and/or analysis in part because of the low sample volumes they require. Paper-based microfluidic devices are especially useful because they are inexpensive and easy to construct. Embodiments of the present BADS use a paper-based microfluidic device within the BAP for bioaerosol detection. A lamination procedure can be used to laminate the paper-based microfluidic device in the system to improve mechanical strength of the device, and in an embodiment the BAP of the BADS uses a laminated paper-based analytical device (LPAD) or laminated paper-based microfluidic device for bioaerosol detection. An LPAD can be a laminated paper-based microfluidic device. Any number of detection methods can be coupled to the microfluidic device of the BAP in the present BADS to detect amplified bioaerosols, and one skilled in the art would recognize which detection methods are suitable for detection and/or analysis depending on the desired application.

In an embodiment the system can contain a bioaerosol amplification unit (BAU). The bioaerosol amplification unit can have a chamber in which air containing bioaerosols is drawn into. In certain embodiments, the chamber can be compressible. The chamber can have one or more walls that can be covered with a wick and wetted with a liquid, such as water. The liquid used to the wet the wick on the chamber wall[s] can be water having a temperature of about 35° C. to about 65° C. The wick can be porous and hydrophilic. Water can spread throughout the wick using capillary action and/or gravity. Excess water on the walls of the chamber and/or wick can be drained with a drain. A filter can be placed on the drain. In an embodiment, the liquid on the chamber wall is warm and can be water. In an embodiment, the liquid throughout the wick is warm and can be water. The wick can stay wet by pumping liquid to the wick with a pump.

In an embodiment, air to be sampled can be drawn into the chamber of the BAU with a vacuum pump. The air can contain aerosols, especially bioaerosols. Viral particles (also described herein as viral aerosols or viral bioaerosols) can be among the bioaerosols in the air. The bioaerosol-containing air can be cooled. In an embodiment, the bioaerosol-containing air is cooled with adiabatic cooling within the BAU. The cool bioaerosol-containing air can be mixed with warm steam to induce swirling-mixing. In an embodiment, the mixing ratio (warm steam flow rate/cold aerosol flow rate) can be varied to control swirling-mixing behavior of the aerosol and the warm steam. In an embodiment, the mixing ratio (warm steam flow rate/cold aerosol flow rate) is high. In an embodiment, the mixing ratio can be controlled with a controller. In an embodiment, a temperature gradient exists between the wetted walls of the chamber and the warm steam. In an embodiment, the chamber of the BAU can be configured to produce or accommodate a temperature drop, and the temperature drop can be controlled by the ratio of the pressure of the air within the chamber after expansion to the ratio of the air within the chamber before expansion. The air can optionally be compressed within the chamber to aid in amplification. The bioaerosol-containing air can be mixed with swirling-mixing. In an embodiment, swirling-mixing is induced by mixing cooled bioaerosol-containing air with warm steam. The bioaerosols in the air can be amplified in combination with water vapor condensation. In an embodiment, water vapor condenses on the bioaerosols in the air to amplify particle size. In an embodiment, the air contains viral particles or bioaerosols or aerosols that are amplified by the BAU. Viral particles can be amplified or enlarged from nanometer-sized to micrometer-sized. In an embodiment, the BAU is a viral amplification unit (VAU) that amplifies viral aerosols.

The bioaerosol containing air within the BAU can have a temperature of about −40° C. to about 10° C., about −30° C. to about 0° C., or about −20° C. to about −10° C. Bioaerosol-containing air within the BAU can have a flow rate of about 1 Liters/min to about 10 Liters/min, about 2 Liters/min to about 9 Liters/min, about 3 Liters/min to about 8, about 4 Liters/min to about 7 Liters/min Liters/min, or about 5 Liters/min to about 6 Liters/min. The BAU can contain steam, and the steam can have a temperature of about 35° C. to about 65° C., about 40° C. to about 60° C., about 45° C. to about 55° C., or about 50° C. The BAU can contain steam that has a flow rate of about 0.1 Liters/min to about 50 Liters/min, about 1 Liters/min to about 50 Liters/min, about 10 Liters/min to about 50 Liters/min, about 20 Liters/min to about 40 Liters/min, about 0.2 Liters/min to about 0.9 Liters/min, about 1.1 Liters/min to about 9 Liters/min or about 30 Liters/min.

In order to amplify viral aerosols for suitable detection, the steam may be warm but not so hot as to inactivate the viral aerosols. For other living bioaerosols, it may be necessary to adjust the steam temperature so as to not kill the organisms. Air with or without bioaerosols in the BAU may also contain non-biological aerosols (sand particles, etc). If it is desired to amplify non-biological aerosols, steam temperatures higher than 65° C. may be used within the system. It would be apparent to one skilled in the art to adjust the steam temperature accordingly depending on the application and the desired aerosol one wishes to amplify.

In an embodiment, the BADS contains a biosampler. The biosampler can comprise a collection vessel containing a collection reservoir (and optionally a collection medium) and can be in fluid connection with the chamber of BAU. Amplified bioaerosols can be drawn into the collection vessel of the biosampler from the BAU and collected within the collection reservoir, in the collection medium within (if present). The biosampler can contain an impinger to aid in collecting amplified bioaerosols for analysis. In an embodiment, amplified bioaerosols can be drawn into the collection vessel of the biosampler and driven by an inertia-based collection method or device into a collection medium in the collection reservoir. In an embodiment, the inertia-based collection device can be an electrostatic precipitator. In an embodiment, the collection reservoir can contain a collection media, and the collection medium can be a fluid. In an embodiment, the collection reservoir lacks a fluid collection media. In an embodiment, the collection media is the liquid that is condensed on the bioaerosols during bioaerosol amplification. The fluid of the collection medium can be culture media. The fluid of the collection media can be water or otherwise have the properties similar to water. The collection media can contain a component (for example an enzyme with a lysis function) and/or buffer that breaks parts of the viral particles down and preserves only certain components of viral particles, such as intact nucleic acids and/or proteins or fragments thereof. In an embodiment, amplified viral aerosols are drawn from the chamber of the BAU into the collection vessel of the biosampler, where they are driven into the collection medium of the collection reservoir by electrostatic precipitation.

In an embodiment, the amplified bioaerosols collected in the biosampler of the BADS are delivered to a bioaerosol analysis platform (BAP). The biosampler can be in fluid connection with the BAP. The amplified bioaerosols can be delivered from the biosampler to the BAP with a pump, such as a peristaltic pump. The BAP can detect viral aerosols. The BAP can contain a bioaerosol detection assay. The BAP can contain a microfluidic device to analyze bioaerosols and amplified bioaerosols. In an embodiment, the BAP uses one or more microfluidic devices to analyze and/or detect bioaerosols or components thereof. In an embodiment, the BAP uses one or more microfluidic devices to analyze amplified viral aerosols. In certain embodiments, the BAP can receive bioaerosols delivered manually by the user, by a device such as a micropipette or other suitable pipetting device.

The BAP of the BADS can include one or more bioaerosol detection assays, such as a nucleic acid detection assay or an immunoassay. A bioaerosol detection assay can detect or analyze bioaerosols and/or components thereof. A detection assay could also include a purification method such as high-pressure liquid chromatography (HPLC), optical detection method, or any other conventionally used detection method to detect bioaerosols or bioaerosol components such as, but not limited to, proteins, nucleic acids, lipids, and/or carbohydrates. A bioaerosol detection assay can use a molecular beacon and generate a chemiluminescent or fluorescent signal in response to the presence of a bioaerosol or components thereof. The nucleic acid detection assay can be an isothermal ribonucleic acid detection assay, such as nucleic acid sequence-based amplification (NASBA) or reverse-transcription loop-mediated isothermal amplification (RT-LAMP). The nucleic detection assay can be real-time reverse-transcriptase polymerase chain reaction (RT-PCR, also known as real-time PCR or quantitative real-time PCR (qRT-PCR)). The nucleic acid assay can utilize molecular beacons and detect amplicons by generating a fluorescent or colorimetric signal. An immunoassay can be configured to detect bioaerosol components, such as nucleic acids, proteins, and/or molecules on virus surfaces. Bioaerosol components can be nucleic acids, proteins, lipids, carbohydrates, or any other constituent that constitutes structure and/or function of the bioaerosol. The immunoassay can be an enzyme-linked immunosorbent assay. The immunoassay can generate a colorimetric signal. The nucleic acid detection assay or immunoassay can be carried out with the assistance of magnetic beads. The nucleic acid detection assay can have lysis, wash, and detection steps. The nucleic acid detection assay can be carried out in thin-walled polymerase chain reaction (PCR) tubes or centrifugal tubes. The immunoassay can be performed with an immiscible phase separation device as described herein or other formats known in the field. The bioaerosol detection assay can be performed on or within a microfluidic device, a paper-based microfluidic device, or a laminated paper-based microfluidic device.

In embodiments of detection assays as described herein, a detection assay can be configured to detect a coronavirus or an influenza virus. In embodiments of detection assays as described herein, a detection assay can be configured to detect a SARs-CoV-2 coronavirus or a H1N1 influenza virus. Nucleic acid sequences of these viruses against which detection assays can be designed to detect (or otherwise configured to detect) are known in the art (for example, National Center for Biotechnology Information (NCBI) Genbank Accession numbers MT668716 and MT670008 for SARS-CoV-2). Examples of primers that can be conjugated to detection assays and/or systems or otherwise used with detection assays and systems as described herein are presented in the examples below, although the skilled artisan would recognize that other primer sequences can be design and used according to methods as known in the art.

A microfluidic device of the BAP within the present BADS can be constructed from plastic, glass, or paper substrates, or other suitable substrates. In an embodiment, the microfluidic device substrate is paper. A paper-based microfluidic device can be constructed by impregnating a hydrophobic photoresist into a paper substrate followed by patterning via photolithography to create hydrophobic boundaries. A paper-based microfluidic device can also be constructed by creating hydrophobic boundaries in hydrophilic paper by printing a pattern of wax and heating the wax so it is impregnated into the paper substrate. Physical boundaries for fluid flow can be mechanically, chemically, or otherwise etched into the substrate of microfluidic device with a suitable etcher and/or etchant. Physical boundaries for fluid flow on a microfluidic substrate can also be created with printed plastic or polymer composition. Hydrophobic and/or physical boundaries are designed to restrict the flow of fluid in a certain direction.

In an embodiment, the microfluidic device substrate is paper. The paper can be a chromatography paper and can be a porous paper and/or hydrophilic paper. The paper-based microfluidic device can be cut from a sheet or roll of paper with a cutting device, such as a craft cutter. The sheet or roll of paper can be affixed to a carrier sheet in order to increase rigidity during cutting. A sacrificial polymer film can be placed on the paper during cutting/fabrication to reduce tearing. In an embodiment, the microfluidic paper device can optionally be laminated with a laminate to improve mechanical strength. In an embodiment, the laminate is a polyester or other polymer film. The area of the laminate can be slightly smaller than the area of the paper substrate to allow for un-laminated areas of paper substrate where reagents or samples for analysis can be applied. Laminating can be accomplished through a device such as a heated roll laminator or a common clothes iron. The spacing between the rollers of a roll laminator can be adjusted to adjust the compression and effective pore size of the paper and therefore the flow rate of fluids within the device. The microfluidic device of the BAP can be a paper-based analytical device, a paper-based microfluidic device, a laminated paper-based analytical device (LPAD), or a laminated paper-based microfluidic device.

The microfluidic device of the BAP of the present BADS can have a sample inlet and/or outlet. The sample inlet can receive amplified bioaerosol samples from the collection medium of the collection reservoir. The sample inlet can be in fluid communication with the collection reservoir. The sample inlet can be a small area of un-laminated paper substrate and can be a sample pad. The sample outlet can pass bioaerosol samples in collection medium to another microfluidic device. The sample inlet and sample outlet can be in fluid communication via a channel or other means. In an embodiment, the microfluidic device optionally has more than one channel in parallel between the collection reservoir and sample inlet to improve sample throughput. In an embodiment, amplified viral aerosols in the collection medium of the collection reservoir are drawn into a channel of the microfluidic aerosol analysis device through the sample inlet. In an embodiment, amplified viral aerosols are drawn into several channels connected in parallel of the microfluidic aerosol analysis device through the inlet. In an embodiment, the microfluidic device and BAP together can comprise a paper-based microfluidic virus platform (MVP).

A microfluidic device of the BAP of the present BADS can contain a sample pad to which a microliter-scale volume of collection medium containing amplified bioaerosols and/or components of amplified bioaerosols from the collection reservoir is delivered. The sample pad can be an area of un-laminated paper substrate. Collection medium can be delivered to the sample pad via a micropipette or a syringe. Collection medium can be delivered to the sample pad through an automated fluid delivery means, such as a tube in fluid communication with the collection reservoir and a pump that delivers fluid from the collection reservoir to the sample pad.

The microfluidic device of the BAP of the present BADS can contain one or more detection zones in fluid communication with the sample pad through one or more channels in the microfluidic device. In an embodiment, the microfluidic device can contain sample pad and a detection zone for a negative control. In an embodiment, the microfluidic device can contain a sample pad, a detection zone for a negative control, and one or more detection zones for positive controls. In an embodiment, a positive control can be bovine serum albumin (BSA). In an embodiment, a positive control can be glucose. In an embodiment, the microfluidic device can contain a sample pad, a detection zone for BSA, a detection zone for glucose, a detection zone for a negative control. In an embodiment, the microfluidic device can have a sample pad, a detection zone for a negative control, and one or more aerosol detection zones. In an embodiment, the microfluidic device can have a sample pad, a detection zone for a negative control, and one or more virus detection zones. The detection zones can detect viruses. The detection zones can detect viral components, such as nucleic acids or proteins. If more than one virus detection zone is present, the detection zones can detect different viruses and/or viral components respectively, or the same virus and/or viral components. If more than one virus detection zone is present, the detection zones can be functionally linked to different detection assays. The sample pad and detection zones can be of any geometric shape. In an embodiment, the microfluidic device is an LPAD or laminated paper-based microfluidic device with an un-laminated sample pad, a detection zone for a negative control, and one or more detection zones for viruses and/or viral components.

The sample pad and/or detection zone[s] of the microfluidic device of the BAP can be functionally coupled to one or more bioaerosol detection methods or assays. A bioaerosol detection method can be a protein assay. A bioaerosol detection method can be an immunoassay to detect protein. In an embodiment, a detection zone of a paper microfluidic device can be coupled to a protein assay that can include dried citric acid buffer and dried tetrabromophenol blue. The dried citric acid buffer can be of pH about 1.8. The bioaerosol detection method can be chemiluminescent assay. In an embodiment, the detection zone of a paper microfluidic device is coated with chitosan, followed by cross-linking using an amine-reactive bifunctional molecule (for example glutaraldehyde). The bioaerosol detection method coupled to a detection zone can be an immunoassay. The bioaerosol detection method can be a non-competitive or competitive immunoassay, homogenous or heterogeneous. An immunoassay on a detection zone can use a variety of probes, for example peptide or nucleic acid. The probe in an immunoassay can be coupled to an electrically charged electrode. An immunoassay on a detection zone can employ one or more reporting methods, including but not limited to enzyme-linked reporting, radio-isotope decay reporting, DNA reporters, flourogenic reporters, electrochemiluminescent reporters, or a label-less reporter method (such as a surface plasmon resonance or measuring change in electrical resistance upon antigen binding to an electrode). Bioaerosols can be detected from the detection zone of a microfluidic device using luminol and horseradish peroxidase (HRP). The immunoassay coupled to a detection zone can detect protein. The immunoassay can be configured to detect viral protein. Detection methods or assays may need optimization by varying parameters such as reagent concentration or incubation time, for example, for optimal performance.

In an embodiment, the bioaerosol detection method coupled to a detection zone of a microfluidic device of the BAP is a nucleic acid detection method. In an embodiment, the nucleic acid detection method coupled to a detection zone is an isothermal amplification reaction for the detection of ribonucleic acid (RNA), such as nucleic acid sequence-based amplification (NASBA) or RT-LAMP. Embodiments of sequences of primers that can be used in conjunction with such nucleic acid detection assays (and that can be conjugated to detection zones by methods known in the art) are provided in the examples below, although it is understood that other primers can be designed and used according to known reference sequences (examples of which are also provided herein).

In an embodiment, a detection zone is coupled to an immunoassay that detects viral protein. In an embodiment, a detection zone is coupled to an immunoassay that is configured to detect viral nucleic acid. Multiple microfluidic devices can be in fluid communication with one another and functionally coupled within a bioaerosol analysis platform in an array to increase detection throughput.

The detection assays of the detection zones of the microfluidic device[s] of the BAP can generate an amplified bioaerosol detection signal. The detection signal can optionally be broadcast through a wired (fiber or GigE for example) or wireless (cellular, bluetooth, and/or WiFi for example) means to a device configured to detect, receive, and/or process the detection signal. The signal can be detected and analyzed by an optical device, for example a smartphone with lens, imaging sensor, and an application configured to receive and process data from the imaging sensor, and a display configured to display data from the application.

Herein described is a method for detecting bioaerosols. The method can comprise the steps of: providing an BADS; delivering air containing bioaerosols to the amplified aerosol detection system; adiabatically cooling the air containing bioaerosols in the bioaerosol amplification unit of the BADS, wherein the air containing aerosols is cooled within a chamber of the bioaerosol amplification unit, wherein the chamber of the bioaerosol amplification unit has one or more interior surfaces adjacent to the air containing bioaerosols, wherein the one or more surfaces are wetted with warm water; mixing cooled air containing aerosols with warm steam in the chamber of the bioaerosol amplification unit; delivering air containing amplified bioaerosols from the bioaerosol amplification unit to a biosampler of the BADS, wherein the biosampler is configured to receive the air containing amplified bioaerosols through a sample inlet and collect amplified bioaerosols in a collection reservoir; precipitating, concentrating, or both the amplified bioaerosols into the collection reservoir of the biosampler; delivering the collected bioaerosols from the collection reservoir of the biosampler to a bioaerosol analysis platform, wherein the bioaerosol analysis platform is functionally coupled to one or more bioaerosol detection assays; and detecting bioaerosols with one or more detection assays. The bioaerosol detection assay can be nucleic acid detection assays, such as NASBA or RT-LAMP, or an immunoassay, such as an ELISA, that is configured to detect one or more bioaerosols or components thereof. The detection assays can further be configured to detect viruses. The bioaerosol amplification unit of the method can be a cylinder with an interior chamber. The cylinder can have a sample inlet and sample outlet, and the walls of the chamber can be covered in a wick that is wetted with warm water. The chamber can also have a drain to drain excess water from the wick. The chamber can be connected to a vacuum pump to draw in air containing bioaerosols and can be in fluid communication with a steam inlet, which provides warm steam to the chamber to mix with the adiabatically cooled air containing bioaerosols. It is important that the steam not be too hot so that bioaerosols are not inactivated. There can also be collection media in the collection reservoir of the biosampler which amplified bioaerosols are collected into. The collection media can contain a bioaerosol stabilization component and/or can contain a bioaerosol lysis component. The collection media can preserve components of bioaerosols for detection, such as proteins and/or nucleic acids. The collection media can be a culture media.

EXAMPLES

Now having described the embodiments of the disclosure, in general, the examples describe some additional embodiments. While embodiments of the present disclosure are described in connection with the example and the corresponding text and figures, there is no intent to limit embodiments of the disclosure to these descriptions. On the contrary, the intent is to cover all alternatives, modifications, and equivalents included within the spirit and scope of embodiments of the present disclosure.

Example 1

Viruses are small entities, typically ranging from 20-300 nm, which can replicate only inside living cells (Prescott et al. 2006). Many viruses can be transmitted through airborne routes, and airborne viruses are responsible for various diseases in humans, animals and plants, such as chickenpox (by Varicella-zoster Virus, VZV), common cold (by coronavirus), influenza of humans and animals, rinderpest of cattle and large ungulates (by morbillivirus), bovine respiratory disease (by Bovine Respiratory Syncytial Virus, BRSV), and some plant viruses that get aerosolized from soil. The seasonal influenza alone causes 3,000-49,000 deaths (Thompson et al. 2003), 3.1 million hospitalized days, 31.4 million outpatient visits, direct medical costs of $10.4 billion, and lost earnings due to illness and loss of life amounting to $16.3 billion per year in US (Molinari et al. 2007). In 1918, pandemic influenza caused 20 million deaths globally. Many deadly viruses have also been weaponized and intended for offensive use in the form of aerosols. Hence, sampling and detection of airborne viruses is critically important for agriculture, animal husbandry, biodefense, conservation, epidemiology, public health, and in general, for developing better protection and prevention strategies for animal and human health, public safety and welfare.

Limitations of Current Sampling Techniques for Viral Aerosols

Figures 1A, 1B, 2:
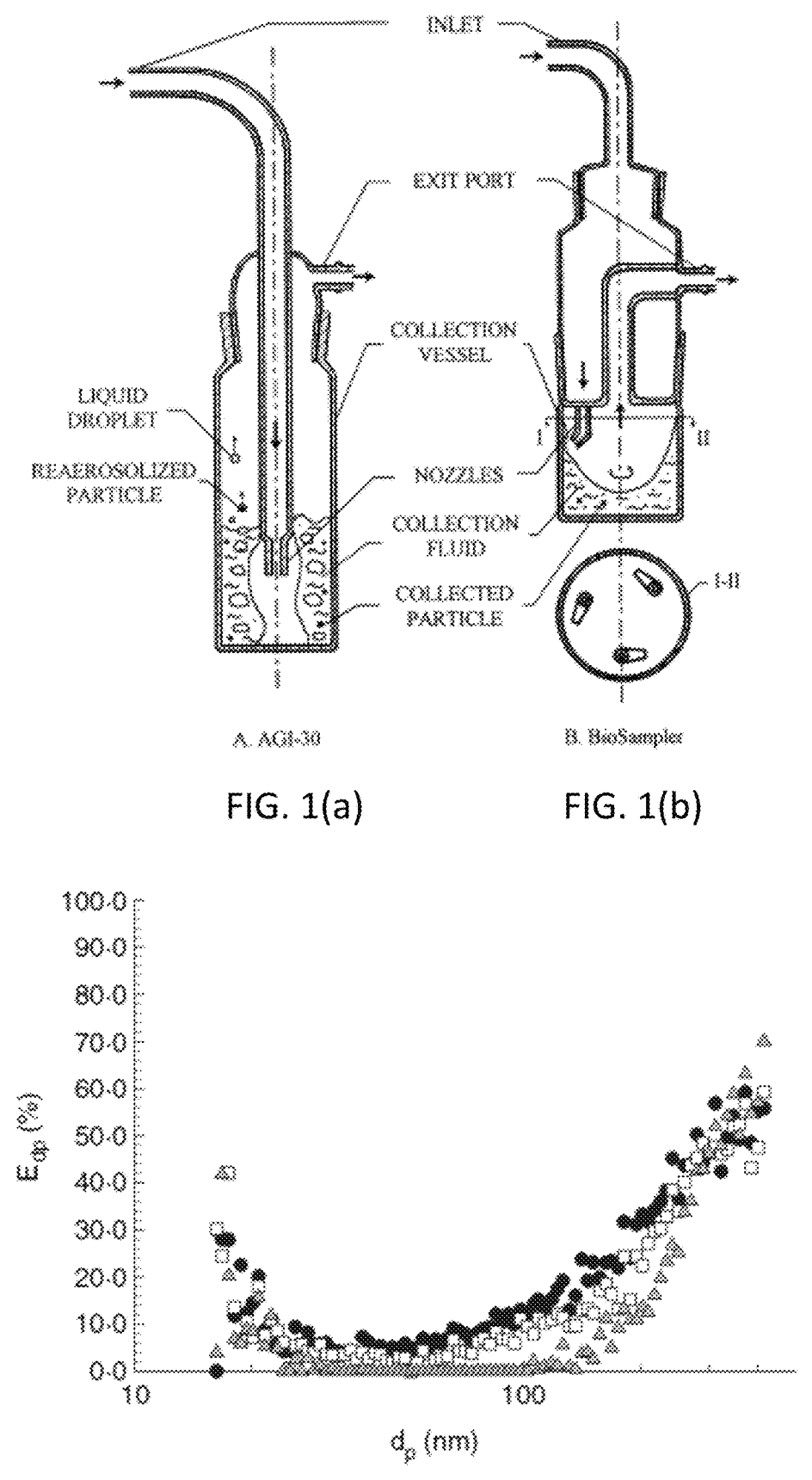

Bioaerosol sampling is typically performed using an impingement method, i.e. directing an air jet containing biological particles to impact on an aqueous collection medium. Because the collection mechanism is inertia based, sampling devices in this category such as All-Glass Impinger (AGI) and the BioSampler® are effective in collecting supermicron (>1 µm) particles but are less so for particles in the nanometer range. FIG. 1 displays a schematic diagram illustrating the collection mechanism of an AGI and a BioSampler. Hogan et al. (2005) conducted experiments using bacteriophages MS2 (dia=27.5 nm) and T3 (dia=45 nm) to characterize their collection efficiency in the AGI-30, the BioSampler and a frit bubbler. FIG. 2 displays the results. As shown, the efficiency is terribly low (5-10%) in the 20-100 nm range, which coincides with many viruses. Woo et al. (2012) later also verified such a trend and developed a "correction factor" for estimating the actual value. However, such a factor is subject to large uncertainty since the actual efficiency is close to noise level. These studies clearly show the limit of impingement methods for collecting viral aerosols in the nanometer range.

Other common bioaerosol sampling methods also have their limitations for viral aerosols. Electrostatic collectors have a poor charging probability for nanometer particles (Hogan et al. 2004), e.g. 5.2% for 20 nm particles. In addition, the production of ozone at high electrical field intensity can damage viruses (Cox 1987). Filters have high physical collection efficiency. However, they cause more structural damages than other methods. Their extraction is often inefficient because nanometer entities adhere strongly on surfaces (Tseng and Li 2005; Verreault et al. 2008). An Ultraviolet Aerodynamic Particle Sizer (UV-APS) is a real-time bioaerosol sampling instrument which measures fluorescence from fluorophores (i.e. nicotinamide adenine dinucleotide phosphate (NADPH) and riboflavin in a live microorganism) excited by pulsed-UV laser to determine viable bioaerosols (Agranovski et al. 2003; Agranovski and Ristovski 2005). Many researchers have considered using the UV-APS for viral aerosols, but none has been able to correlate the data reads with the presence of agent. Furthermore, sensitivity of detection by the UV-APS is a big issue for virus aerosols because of their nanometer particle size, and lack of fluorophores. Recently, a silicon nanowire sensor functionalized using antibodies was developed for monitoring airborne virus by utilizing the change in conductance in the presence of a virus particle (Shen et al. 2011). While successful detection of influenza virus was demonstrated, the system is still plagued by the low charging efficiency of an electrostatic system for nanometer particles. In short, all the above known devices are inefficient for viral aerosol sampling. Hence, the development of a device capable of efficient viral aerosol sampling is greatly needed.

To overcome the inertia limitation for viral aerosols, one possible solution is to amplify nanometer virus particles to much larger supermicron particles, which would then be efficiently collected by an inertia-based method. Particle size enlargement by condensation of alcohol vapor has been realized for non-biological aerosols for decades (Agarwal and Sem 1980). The commercial instrument, i.e. condensation particle counter (CPC), adopting this principle has one heating chamber for vaporizing alcohol from an alcohol reservoir to saturate the sample air, followed by one cooling chamber to create a supersaturation condition (S=actual vapor pressure/saturation vapor pressure>1) that would allow condensation of alcohol on aerosols. As alcohol inactivates viruses, using an alternative condensing material such as water is desired for viruses. However, simply replacing alcohol by water using the same design as the conventional CPC does not work. This is because the higher molecular diffusivity of water vapor compared to the thermal diffusivity of air coupled with the temperature gradient in the condensation chamber limit particle growth by causing condensation to occur predominantly at the colder chamber wall rather than on particles (Hering et al. 2005). This explains why the system built by Milton and coworkers (McDevitt et al. 2013; Milton et al. 2013) had a performance "comparable" to the BioSamplers when they used water vapor for collecting infectious influenza aerosols from exhaled breath from patients. Oh et al. (2010) observed the same problem when they used the cooling principle for collecting 28 nm MS2 viral particles in a laboratory setting, but they successfully improved collection by switching to a "mixing" chamber (mixing of a cold aerosol flow with a hot moist air flow) to create a proper supersaturation environment that activated condensation on particles (Kousaka et al. 1982; Wu et al. 2013).

Conventional Methods for Identifying and Quantifying Viruses

Once sampled, several techniques are available for identifying the virus and quantifying the amount. Conventional methods for quantifying virus are plaque assay and 50% tissue culture infectious dose ($TCID_{50}$), which require culturing of the host cells first followed by infecting the host. They are important tools for measuring viral infectivity, but are rather time-consuming. Other virus detection methods include enzyme-linked immunosorbent assay (ELISA) and polymerase chain reaction (PCR). ELISA relies on a specific antibody and a color change to identify a virus. Briefly, a specific antibody attached to an enzyme binds to its target on the virus. The enzyme reacts with a color substrate resulting in a visible signal. PCR is a biochemical technique wherein a DNA template is "amplified" through repetitive copying cycles by a DNA polymerase. Unfortunately, many airborne viruses contain RNA genomes. If RNA is the template, a preliminary step referred to as "reverse transcription" is necessary to produce a DNA template for PCR. Standard ELISA and PCR do not require viable (infectious) viruses, but these procedures are still complex and slow, and therefore cannot be used for rapid detection in field investigation. If they can be modified to perform like the rapid influenza diagnostic testing based on lateral flow immunochromatographic assays, a form of ELISA, they will be powerful tools for virus detection in the field.

Microfluidics Technology

Reaction kinetics is controlled by concentration and volume. Hence, by confining the reagents in a smaller volume, it is then possible to enable faster processing. Microfluidics can be a perfect platform to achieve this goal. Microfluidics technology has been used to construct miniaturized analytical instruments called "Lab-on-a-chip" devices. The principles of microfabrication and microfluidics, as well as their current and potential applications, have been reviewed in the literature (Arora et al. 2010; Whitesides 2006). Common analytical assays, including PCR, protein analysis, DNA separations, and cell manipulations have been reduced in size and fabricated in a centimeter-scale chip. The size reduction of an analytical instrument has many advantages including high speed of analysis, minimization of required sample and reagents, and ability to operate in a high-throughput format. Most microfluidic devices can be made from silicon, glass, or plastics, as reviewed by Manz's group (Arora et al. 2010). A variety of glass, plastic, and paper devices can be fabricated for various applications including: DNA analyses (Boone et al. 2002; Fan et al. 1999), protein separation (Das and Fan 2006; Das et al. 2007; Tan et al. 2002), bacterial and toxin detection (Koh et al. 2003; Mei et al. 2005; Mei et al. 2006), and protein expression (Khnouf et al. 2009; Mei et al. 2010; Mei et al. 2008). Plastics can be used because of (1) biocompatibility of plastics (evidenced by plastic labwares); and (2) processes in manufacturing low-cost, high-volume plastic parts with micro-scale features (e.g., compact disc, a two-layer structure containing micron-scale features). The fabrication process of plastic microfluidic devices has been described previously (Boone et al. 2002; Fredrickson et al. 2006). In addition, microfluidic devices can be fabricated in and/or on a paper substrate. From litmus papers to over-the-counter pregnancy test-kits, paper can be used as an analytical platform. Over the past few years, paper has garnered increasing interest as an option for producing microfluidic devices. This growing interest in paper-based microfluidics is driven by several factors. First, paper as a substrate can simplify a microfluidic system because it is a porous media capable of pumping aqueous solutions through capillary action. Thus, accessories such as a pump may not be needed. Second, paper as an industrial product can be inexpensive, widely available, and derived from renewable resources (Martinez et al. 2007). Paper devices can be fabricated by at least two methods (Li et al. 2012; Yetisen et al. 2013). The first method can pattern and manipulate the hydrophilic property of the paper substrate by impregnating a hydrophobic photoresist (SU-8) into paper, followed by patterning via photolithography (Martinez et al. 2007; Martinez et al. 2008). An alternative approach to create the hydrophobic boundaries in hydrophilic paper can be to print a pattern of wax, followed by heating to allow wax to penetrate into paper (Lu et al. 2009; Lu et al. 2010). The second method can be to form physical boundaries by cutting paper using a laser, knife cutter or plotter to form physical channels (Fenton et al. 2008; Yu et al. 2011). In these devices, either hydrophobic boundaries or physical boundaries can restrict the flow of a fluid in a certain direction.

Paper-based microfluidic devices can be laminated to increase mechanical strength and durability of the devices (Cassano and Fan 2013). In a way similar to making an identification (ID) card as shown in an embodiment in FIGS. 3(a)-(e), a digital craft cutter can be used to create chromatography paper strips based on the designed pattern. The paper strips, cover film, and bottom sheet can be aligned and assembled together as shown in FIG. 3a. The cover film can have a cutout that is slightly smaller than the paper strip so that the paper strip can be accessed for reagent dispensing and sample applications. The assembly can be passed through a heated laminator (FIG. 3b). As the polyester films are heated, they can conform to the outline of the paper strip (FIG. 3c). Both cover and bottom films can be made from polyester, providing mechanical backing to the paper device. A picture of an exemplary LPAD is shown in FIGS. 3d and 3e. By encapsulating the paper strip between layers of thermally bonded polymer films, low-cost and rugged devices can be produced.

Need for a Novel Viral Aerosol Detection System

Because of the poor sampling efficiency and complicated laboratory systems required for conventional analysis, current knowledge of viral aerosol is rather limited (Xu et al. 2011). For example, how influenza is transmitted is still hotly debated even after decades of research. Thus, a system that can enable highly efficient sampling and fast detection of viral aerosols will bring great benefits to our society. The present disclosure is directed to a Highly Efficient and Rapid BioAerosol Detection System (HERBADS) that can combine particle size amplification through condensation of water vapor and rapid analysis through microfluidic units. This system can be a suitable system to fulfill the goal and need of rapid, efficient, and precise analysis of viral aerosols.

The HERBADS is a system that can include a BioAerosol Amplification Unit (BAU) for enhanced sampling efficiency and a paper-based Microfluidic Aerosol Analysis Platform (MAAP) for rapid detection. Each unit can be a useful device itself for improved collection and detection, respectively. Each unit can be combined and integrated. When combined, the integrated system can offer a suitable tool for field investigation.

BioAerosol Amplification Unit (BAU)

Figures 4A, 4B:
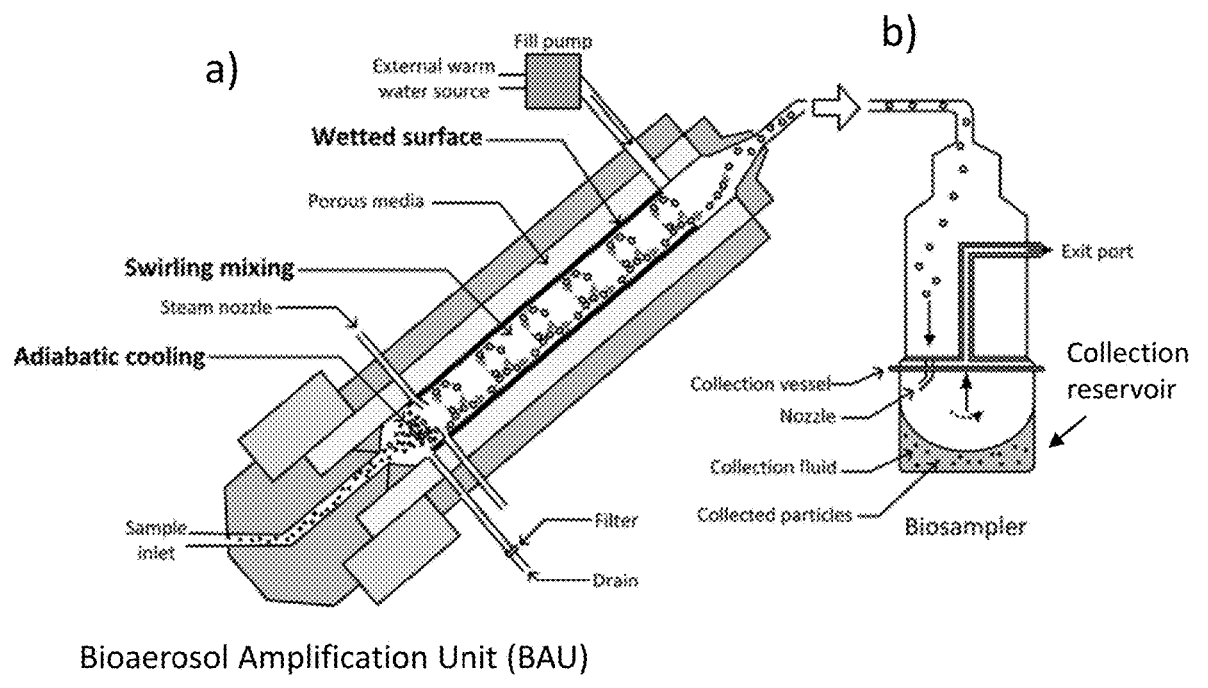

The BAU can be based on the principle of water vapor condensation as described in our recent patent (Wu et al. 2013) which has been successfully proven for increasing MS2 bacteriophage capture efficiency as reported in Oh et al. (2010). To significantly improve its effectiveness and to compact the size, three new features can be incorporated into the BAU: adiabatic cooling, swirling mixing, and/or wetted walls. FIG. 4 displays an embodiment of the system. The bioaerosol stream, which can be a viral aerosol stream, can first be adiabatically cooled to start the initial condensation. The particle size amplification can further be accelerated by swirling mixing with warm steam. The wetted wall can supply more water vapor and can prevent aerosol deposit onto the chamber wall. The amplified aerosols can then be efficiently collected by a collection apparatus, for example an inertia-based apparatus downstream such as a BioSampler. The details of each feature are further discussed in the following subsections.

Adiabatic Cooling

Supersaturation can be a necessary condition for suitable condensation. Herein, adiabatic cooling can be a suitable method to create supersaturation. When an air stream expands adiabatically, its temperature decreases (FIG. 5a) according to the following relationship in equation 1 (Friedlander 2000):

$$\frac{P_{final}}{P_{initial}} = \left(\frac{T_{final}}{T_{initial}}\right)^{\frac{\gamma}{\gamma-1}} \quad \text{(eq. 1)}$$

where p and T are pressure and temperature, $\gamma$ is the ratio of specific heats (1.4 for dry air and 1.33 for water vapor). Since saturation vapor pressure decreases with temperature decrease, air becomes more saturated and condensation is initiated when saturation ratio (S) exceeds 1 (FIG. 5a). FIG. 5b conceptually illustrates the process in an expansion nozzle to be adopted for the new design. In the BAU, the bioaerosols in the supersaturated stream can act as the nuclei for water vapor condensation that yields size amplification. This process is similar to cloud formation in the atmosphere. As shown in Eq. (1), the temperature drop is controlled by the pressure ratio (after vs. before expansion), which is an operating parameter in the BAU.

Swirling Mixing

Figures 6A, 6B:
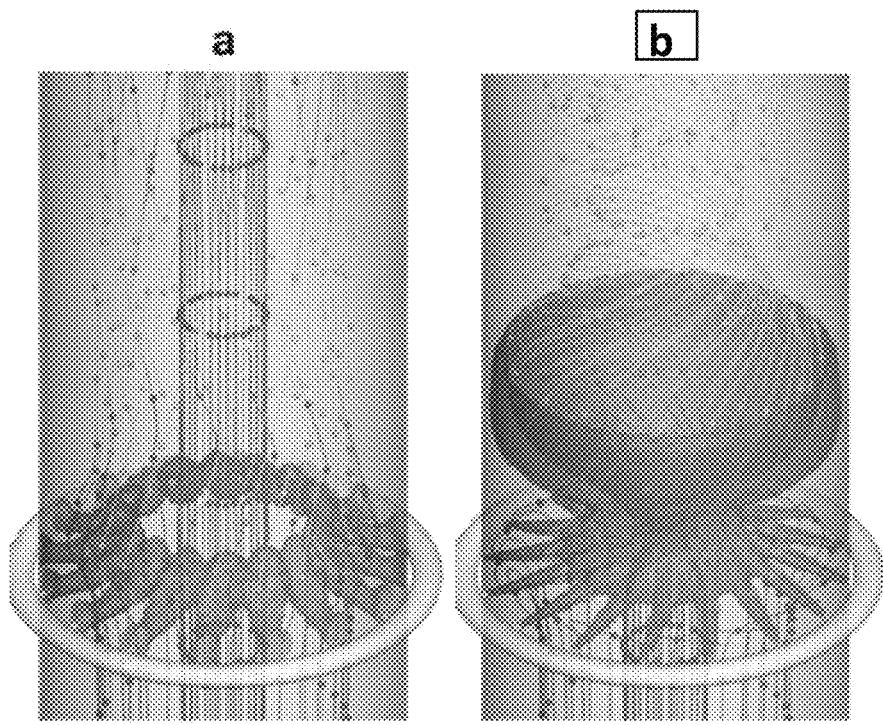
FIGS. 6(a)-(b) show different mixing ratios between aerosol flow and steam.

Close contact between the aerosol and the condensing vapor can be of seminal importance in the condensation process and the degree of closeness can dictate the particle growth rate. Conventional wisdom relying on molecular diffusion in a laminar flow can work, but the growth rate is constrained by the molecular diffusion rate. In the BAU, a swirling mixing process, for example as proposed by Buesser and Pratsinis (2011) (for coating a silica layer onto host titania particles in their work), can be implemented in order to significantly enhance the mixing in the BAU. The cold aerosol stream from the adiabatic cooling can enter the chamber from the center, while warm steam (not overly hot to avoid virus deactivation) can enter from the side with an angle (see FIG. 4(a)). Such a configuration can induce a swirling aerosol motion in the mixing zone. FIGS. 6(a)-(b) displays the flow streamlines in an example configuration. The mixing ratio (warm steam flow rate/cold aerosol flow rate), as inferred, can be a key operating parameter. At a low mixing ratio (FIG. 6a) the exchange between the aerosol flow and the steam can be rather slow. In contrast, a high mixing ratio (FIG. 6b) can yield improved mixing through the swirling action. In other words, the water vapor can better reach the reactor center and this can lead to better exposure of all core aerosol streamlines to the steam. One additional advantage of such a configuration is its high temperature gradient between the warm steam and cold aerosol that can further drive the condensation of water vapor onto the cold aerosol surface. By improving the effectiveness of mixing, the length of the mixing chamber can be reduced, thus enabling a more compact design.

Wetted Wall

A cold surface can induce water vapor condensation due to a temperature gradient between the warm steam and the cold wall, thus depleting the available vapor needed for amplifying the aerosol size. This can be a reason why the cooling chamber design does not work for water condensation (Hering et al. 2005). The temperature gradient can also undesirably drive the amplified aerosols depositing onto the wall. A wetted wall saturated with warm water can overcome this barrier. By providing a higher surface temperature, a "reverse" temperature gradient can be created that "pushes" away approaching aerosols. Furthermore, the warm water released from the wall can replenish the vapor supply, which can further enlarge the aerosol size. The wetted surface can be created by using a porous and hydrophilic wick (FIG. 4(a)). It can maintain constant wetting by means of a small pump that injects water into the wick at the upper end of the growth chamber. Water can spread by capillary action and by gravity down the wick, and the excess can drain out the chamber at the bottom (FIG. 4(a)). To ensure the drain does not become a safety concern, a filter can optionally be used to capture viruses running off in the drain. Nonetheless, the temperature gradient of the wetted wall design can be suitable to minimize such a need.

Incorporating and integrating all the above designs into the system can be complex. To efficiently determine the optimal configuration and operating conditions, computational fluid dynamic simulation coupled with aerosol dynamic modeling can be conducted. The modeling can be carried out, for example, using FLUENT (ANSYS) for fluid dynamics coupled with Fine Particle Model (FPM by Chimera) for aerosol dynamics in parallel on a workstation. FLUENT is a widely used software package that uses numerical methods and algorithms to solve and analyze the interaction of fluid with surface defined by boundary conditions for fluid, heat transfer, and reaction. FPM is designed to model aerosol dynamics including particle formation, growth and transport. The FPM user interface is tightly integrated with the ANSYS FLUENT thus allowing easy setup of standard particle dynamics simulations. First the flow at each time step is determined by FLUENT; the data can then be used as input in the FPM to determine the interaction between aerosols and water vapor. Sensitivity analyses can be carried out for various important operating parameters, including pressure ratio across the nozzle, mixing ratio of the warm stream to aerosol flow, temperature of the wetted surface. A BAU can then be built according to the optimal configuration determined by the modeling.

Figures 7A, 7B:
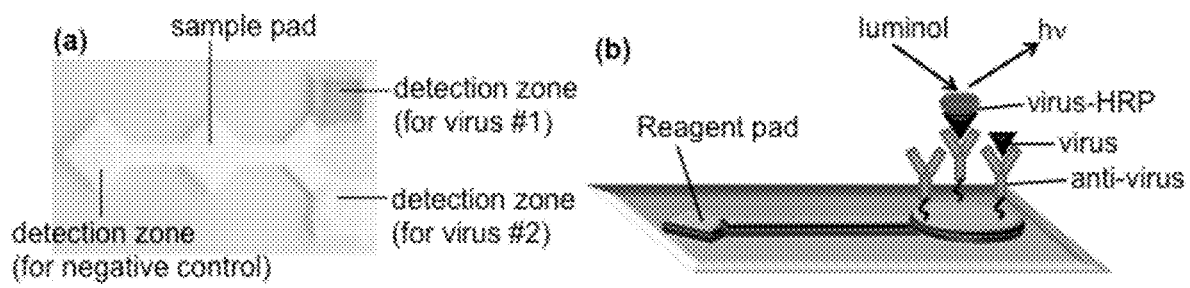
FIGS. 7(a)-(b) demonstrates a representative design of a paper-based analytical device.

Amplified Bioaerosol Detection Platform and Paper-Based Microfluidic Devices for Bioaerosol Detection Device Design Amplified bioaerosols can be detected by a bioaerosol analysis platform (BAP). Microfluidic devices can be used within a BAP for bioaerosol detection, such as viral detection, as shown in FIGS. 7(a) and (b). These layouts show the versatility of the platform, and different designs can be adapted if different assay and detection schemes are required for the intended use. FIG. 7a shows colorimetric assays for simultaneous detection of two viruses. The microfluidic device can include a sample pad, detection zones for virus #1 and virus #2, and a negative control. Reagents can be applied to the detection zone after lamination. For instance, the detection zone can be deposited with citric acid buffer at pH 1.8, followed by drying. It is then spotted with tetrabromophenol blue and allowed to dry again. When a virus sample flows into the detection zone, protein on virus surfaces would make the detection area to turn brownish color (if there are enough proteins).

FIG. 7b shows an alternative embodiment of a microfluidic device design based on chemiluminescence detection. Among many detection methods, chemiluminescence can be one of the more sensitive methods due primarily to little or no background signal. As a result, chemiluminescence can be used for bioaerosol detection, especially for viral aerosol detection. The protocol for implementing the assay can be as follows. First, the detection zone of a paper device can be coated with chitosan, followed by cross-linking using an amine-reactive bifunctional molecule (glutaraldehyde) in a way similar to those reported in the literature (Wang et al. 2012). Chitosan adheres to paper due to electrostatic interactions between positively charged chitosan and negatively charged cellulose in the wet condition. Glutaraldehyde is immobilized onto the surface through amino groups of chitosan. It can also bind covalently with a virus antibody (anti-virus).

The embodiment illustrated in FIG. 7b is a competitive immunoassay in case a tiny virus does not have multiple epitopes for both capture antibody and detection antibody. Otherwise sandwich immunoassay format can be easily adapted. For competitive immunoassays, a sample solution containing virus and a known amount of horseradish peroxidase (HRP) conjugated virus (virus-HRP) can be applied to the detection zone. Both sample virus and virus-HRP can compete with each other for the fixed amount of anti-virus immobilized in the detection zone. After washing, a solution of luminol and hydrogen peroxide can be dispensed to the reagent pad, and flow into the detection zone. The resultant chemiluminescent signal can then be detected, and it can correlate with the amount of the viruses in the sample.

Array Detection

The bioaerosol in FIG. 7b can be easily replaced with proteins expressed by a bioaerosol particle, such as a virus, or other biomarkers related to bioaerosols, such as hemagglutinins and neuraminidase of influenza viruses for example. An array of microfluidic devices, such as paper-based microfluidic devices, can be made in the same amplified bioaerosol detection platform so that a pattern can be generated to address the possible cross-reactivity of antibodies for a range of bioaerosols, such as influenza viruses. The fluidic format of a protein array reported in the literature can be possible for profiling various types of bioaerosols, such as the influenza virus (Koopmans et al. 2012). Array-based detection in this sense can be more accurate than commercially available lateral flow assay kits for bioaerosols, such as the influenza virus or other viruses or bioaerosols that are based on one protein. The pattern-recognition from an array using a number of biomarkers can reduce or eliminate false-positives and false-negatives that are often encountered from an assay using a single biomarker.

Low Sample Volume

Figure 8:
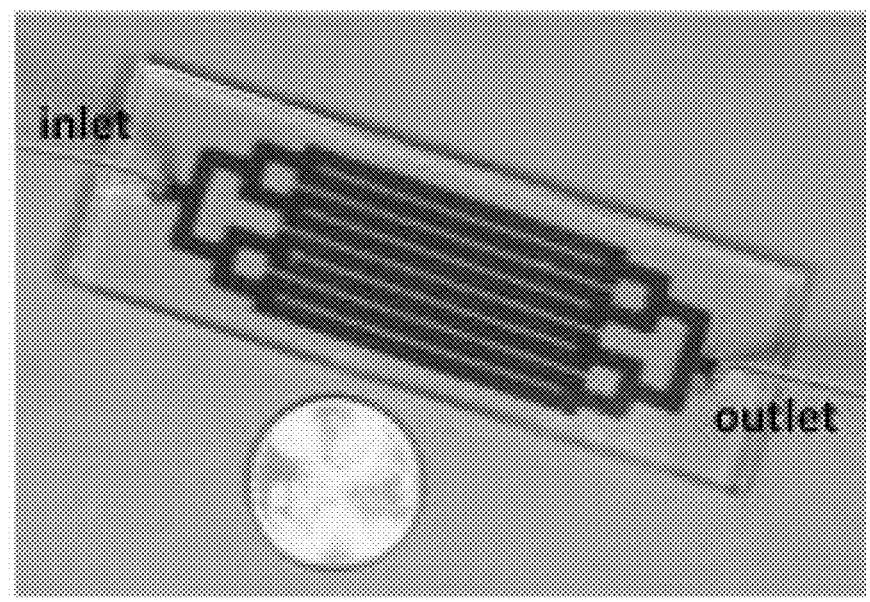
FIG. 8 shows a microfluidic device for improving throughput volume.

One common concern about microfluidics-based method is the sample volume. Sometimes sample volume or collection media can be low, and there can be a potential issue regarding the sampling accuracy. For example, when the virus concentration in a sample solution is 10 virus particles/mL, processing 100 μL of the sample solution should detect 1 virus particle on average, but with a possibility of zero virus detected. As a result, at least 300 to 500 μL of the sample solution should be processed to ensure accurate sampling. If sample bioaerosol volume in the present system is low, device throughput can be increased in the amplified bioaerosol detection platform with the addition of parallel microfluidic channels. FIG. 8 shows the picture of an embodiment of one glass device including 8 channels that are connected through bifurcations. A device such as this can process 2 μL/s blood samples for example, and can be designed to capture rare circulating tumor cells in peripheral blood (Sheng et al. 2012). Typically, the number of tumor cells in cancer patients can be about 10 tumor cells/mL, thus 1 mL of blood must be processed to ensure sampling accuracy. In this device, one mL of blood takes 8.3 minutes to pass. A device such as this can be incorporated into the presently described BADS to improve bioaerosol throughput and ensure accurate detection and sampling of low concentrations of bioaerosols. Devices can be constructed incorporating parallel channels out of a thermoplastic substrate and incorporated into the presently described system. Both colorimetric and immunoassay detections discussed in FIGS. 7(a)-(b) can be incorporated into the device and system as a whole.

System Integration

As amplified bioaerosols, such as viral particles, can be efficiently collected by inertia-based methods, impingement devices such as a BioSampler can be used to collect the viruses and serve as a reservoir. A sample can then be easily retrieved and delivered to the amplified bioaerosol detection platform by a simple peristaltic pump with tubing connecting the reservoir and the amplified bioaerosol detection platform. Hence, one embodiment of integration will be to demonstrate the capability of this BAU-BioSampler-BAP design.

However, for cases where virus concentration is low, the required volume of collection media in the reservoir (20 mL for the BioSampler) can possibly dilute the concentration down to below the detection limit of the BAP. Hence, an alternative delivery method such as an electrostatic precipitation (ESP) method can be used (Cheng et al. 1981; Hogan et al. 2004) to accomplish the goal. While the charging efficiency for nanosized particles can be low as discussed earlier, supermicron particles such as the amplified particles can be charged very efficiently (~100%). Furthermore, the water content of the amplified particles can shield the viruses from the damaging effect of ozone, a byproduct of corona charging well known to be deleterious to naked viruses. Thus, electrostatic collection can serve as a useful tool. In some instances, viral aerosol concentration can be sufficiently high and aerosols sufficiently amplified that impingers or other collection methods may not be required. In cases such as this, collection can simply rely on gravity or other passive method for amplified aerosols to be collected in the collection media.

Figure 9:
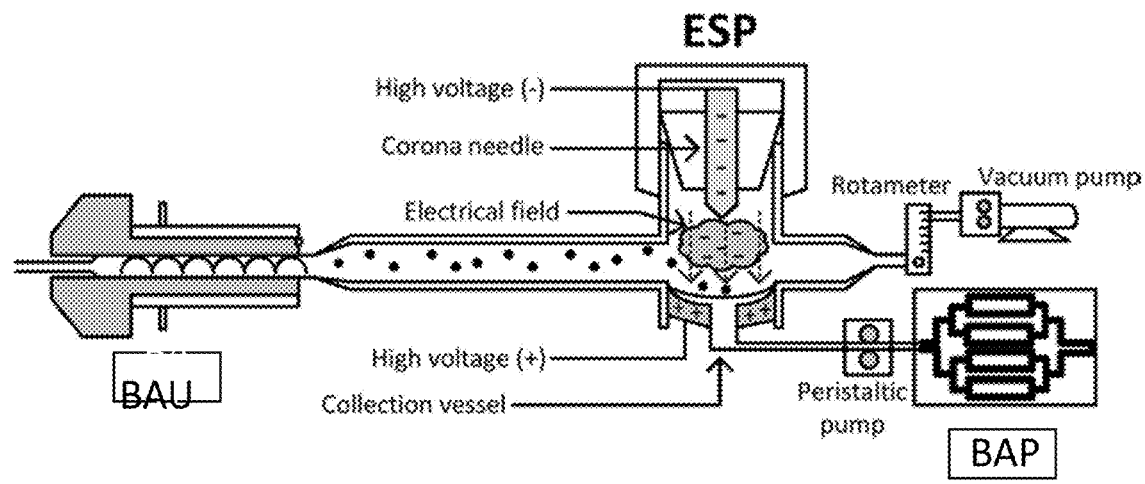
FIG. 9 illustrates an integrated system for the collection of low concentration viral aerosols.

FIG. 9 conceptually illustrates an embodiment of a design of a BADS as described herein. Drawn by a vacuum pump, amplified bioaerosols from the BAU will be directed to an ESP unit where the needle electrode generates corona (crowd of electrons) to charge the amplified bioaerosol particles. Amplified bioaerosols in this embodiment can be viral aerosols. The charged amplified particles can be subsequently attracted by the downward electrical field to the collection vessel at the bottom. The curve of the vessel can allow the collected particles to settle at the bottom. Since this method requires no liquid collection medium like the BioSampler does and only the amplified particles are collected, the virus concentration in the collection should be higher (i.e. more concentrated) than the impingement method. Once sufficient volume of liquid sample is collected, a peristaltic pump will deliver a minute sample to the BAP. The presence of target bioaerosol, such as a virus, can then be detected statically or as a function of time as controlled by the sampling rate.

Performance Testing

Individual Unit Testing

BAU embodiments can be tested and their performance measured using polystyrene latex (PSL) particles of known sizes (30, 50, 100 and 300 nm covering the common size range of viruses). As PSL particles come with a uniform size, the amplification effect can be examined by monitoring the aerosol size and concentration. Another important reason for such a test using non-biological particles is that it can require much less time than testing involving assaying, and can provide a quick but accurate physical characterization.

Figure 10A:
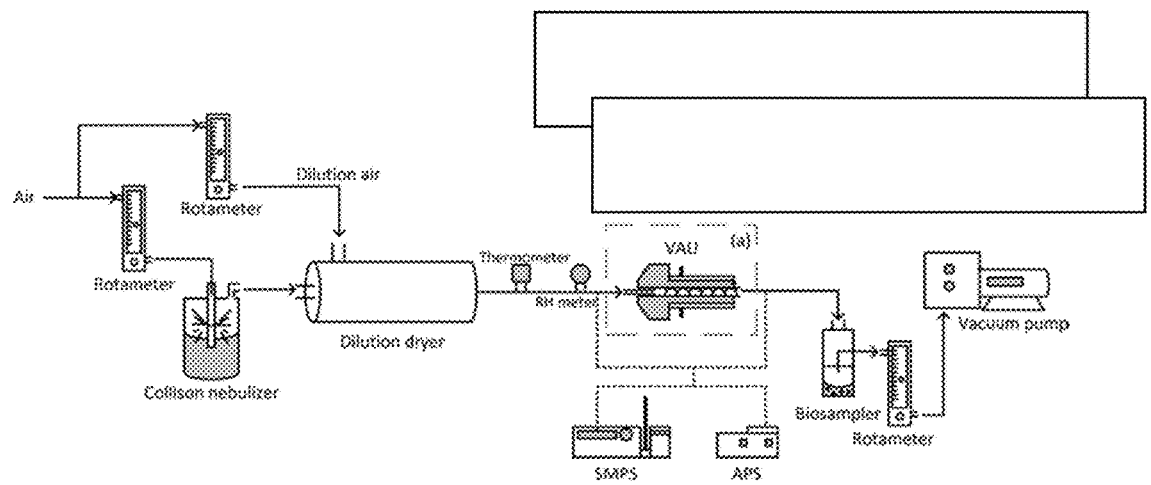
FIGS. 10(a)-(b) demonstrates an embodiment of an experimental system that can be used for testing the effectiveness of the BAU and an entire integrated system.

An embodiment of an experimental system for testing is shown in FIG. 10a. PSL aerosols can be produced by nebulizing a PSL particle suspension (Oh et al. 2010). The nebulized particles can first be conditioned by dry dilution air to vaporize the water content. The aerosols can be monitored for size and concentration by a Scanning Mobility Particle Sizer (SMPS) for the nanometer to lower submicron range (<0.5 μm) and by an Aerodynamic Particle Sizer (APS) for the upper submicron to supermicron range (>0.5 μm). The aerosols going through the system with the BAU off (i.e. no adiabatic cooling, steam and wetted wall) can serve as the baseline for comparison. The comparison of the particle sizes and concentrations with the BAU on and off can reveal the effectiveness of the BAU in amplifying aerosol size.

BAU performance can also be tested with other bioaerosols, such as viral aerosols. MS2 bacteriophage (ATCC 15597-B1) can be a candidate virus for this phase because MS2 only replicates in male $E.$ $coli$ bacteria and is safe to work with in a biosafety level 1 (BSL-1) laboratory. With a diameter of approximately 28 nm, MS2 is a single-stranded RNA icosahedral virus that is commonly used in viral aerosol testing (Grinshpun et al. 2010; Rengasamy et al. 2010; Tseng and Li 2005) because of its similarity to human enterovirus and picornavirus (Aranha-Creado and Brandwein 1999).

The experimental system can be similar to that used for the PSL particles, except that the aerosols can also be collected by a BioSampler downstream (FIG. 10a). The collected samples in the BioSampler can be subjected to standard plaque assay[s] (Adams 1959) using E. coli as host bacterium for infectious count as well as reverse transcript-polymeric chain reaction (RT-PCR) to determine the total virus count. Again, the comparison of the virus counts (plaque assay and RT-PCR) with the BAU on and off can measure the performance of the BAU. In addition, the liquid drained from BAU can be collected and sampled to examine if bioaerosols such as viruses escape through the drain, and the loss through the drain can be quantified. If escape is confirmed, a filter can be installed to increase safety of the device.

Regarding the testing of the BAP, different detection methods such as colorimetric and chemiluminescence detection can be used as discussed above. Known amounts of viruses can be fed to the BAP unit through a syringe or other suitable method, such as a micropipette. The colorimetric method can be simple to implement without a need of an instrument, while chemiluminescence methods can require a photon counter or photomultiplier tube to measure the light generated. For the former, a colorimetric chemistry similar to those in Quidel QuickVue Influenza A+B Test (Quidel, San Diego, CA, USA) can be implemented in paper-based analytical devices. Chemiluminescence detection can be carried out as illustrated in FIG. 7b and discussed in the related text above. Different titers of virus can be used to establish a calibration curve and determine the limit of detection.

System Testing

Information learned by using MS2 bacteriophage cannot be used to generalize about the bioaerosol amplification and detection device described herein for collection efficacy for virus aerosols because viruses have different physical, chemical, and biological properties. For example, MS2 bacteriophages are not covered by a lipid membrane, and are uniform in size, whereas influenza viruses are larger viruses that are pleomorphic, meaning they are non-uniform in shape and can occur in spherical to filamentous forms. Moreover, influenza viruses are covered ("enveloped") by a lipid membrane. The stability of enveloped and non-enveloped viruses in aerosols can be affected by their biochemical makeup, and by temperature and relative humidity. In general, lipid-containing viruses are usually more stable in aerosols than lipid-free viruses, but less stable in moist air than in dry air (Akers 1973).

From on-going work (Fennelly et al. 2011), ultrafine aerosols (mass median aerodynamic diameter ~0.8 µm) of wild-type influenza virus A/Mexico/4108/2009 (H1N1), the H1N1 strain of the 2009 influenza pandemic, can be generated with minimal loss of viral infectivity using a Collison nebulizer. This can be a candidate to be used in device testing methodological verification. Viral stocks can be prepared in serum-free Madin-Darby canine kidney (MDCK) epithelial cells in the presence of trypsin using a low-passage virus isolate (obtained from the CDC). A process that conserves the genotype and produces relatively few defective particles (WHO 2002) can be used for virus production. Virus identity can be confirmed by PCR and sequencing before device testing.

Figure 10B:
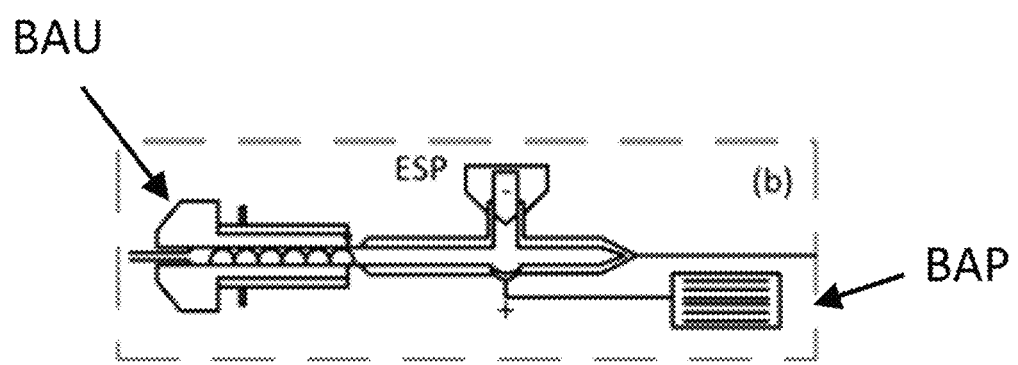

System testing with influenza virus can be performed in a USDA inspected and approved BSL2-enhanced laboratory using a testing system similar to that illustrated in FIG. 10b. Since influenza virus aerosols in field conditions typically are in low concentration, emphasis can be placed on detecting low-concentration virus aerosols, i.e. using the BAU-ESP-BAP design. Influenza virus aerosols can be produced by nebulizing the virus stock, and a targeted volume of air can be sampled. Knowing the titer and liquid volume nebulized, the quantity of influenza viruses within the volume of sampled air, $N_{SampledAir}$, can be determined. The collection efficiency of the bioaerosol amplification and detection device, or highly efficient and rapid BioAerosol detection system (HERBADS) as used in this example, for influenza virus aerosols over a concentration range can then be evaluated according to the following Equation 2:

$$\eta(\%) = \frac{N_{HERBADS}}{N_{SampledAir}} \times 100 \qquad (eq.\ 2)$$

where $N_{HERBADS}$ is the quantity of influenza viruses collected by the HERBADS embodiment in the sampled air. Eq. 2 can be used to evaluate collection efficiency of other bioaerosol amplification detection system embodiments and methods. Viral infectivity can be determined using a TCID50 assay (Hamilton et al. 2011; Lednicky et al. 2010), and the Reed-Muench method can be used to calculate TCID50 values (Reed and Muench 1938). A comparison can be made between viral aerosols through the HERBADS with BAU on and off. The corresponding threshold concentration for detecting influenza viruses by the BAP will be determined.

In parallel, the BAU can also be connected to a BioSampler for testing, which can serve as a baseline for investigating the performance of the electrostatic method. The liquid sampling medium can include phosphate-buffered saline containing 0.5% purified bovine serum albumin fraction V, which can be suitable for the collection of influenza virus aerosols (Lednicky et al. 2010). Ongoing work (Fennelly et al. 2011) and previous projects (Anwar et al. 2010), show that the Biosampler can be operated at a flow rate lower than the manufacturer's recommended sampling rate of 12.5 L/min. Lower flow rates can improve performance for original viruses (i.e. non-amplified). Therefore, the Bio-Sampler can be operated at different flow rates for testing purposes (12.5 and 8 L/min, for example) to explore how different collection characteristics of embodiments of the herein described system[s]. For completion, a quantitative PCR assay can also be used to evaluate the total number of virus particles captured by the bioaerosol amplification and detection device, which can verify whether the steam condensation process inactivates influenza virus particles.

Figure 11:
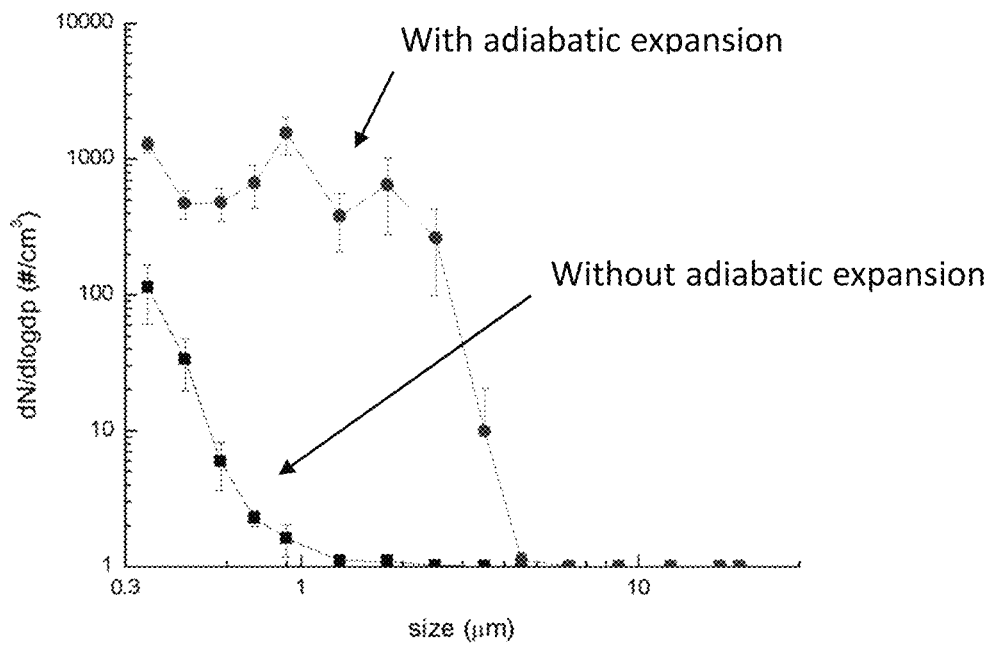
FIG. 11 shows MS2 aerosol particle size distribution with and without adiabatic expansion as described herein.

FIG. 11 shows particle size distribution of MS2 aerosol with and without adiabatic expansion as can be obtained by a BAU described herein. MS2 is a bacteriophage (virus that infects bacteria) that is commonly used as a surrogate for pathogenic viruses. The measurements of aerosol size distribution were made by a device that has a lower detection limit of around 0.3 µm. As shown, without adiabatic expansion, only a small fraction of the particles is larger than 1 µm. With adiabatic expansion, many particles are physically amplified to larger than 1 µm that can be collected efficiently.

Figure 12:
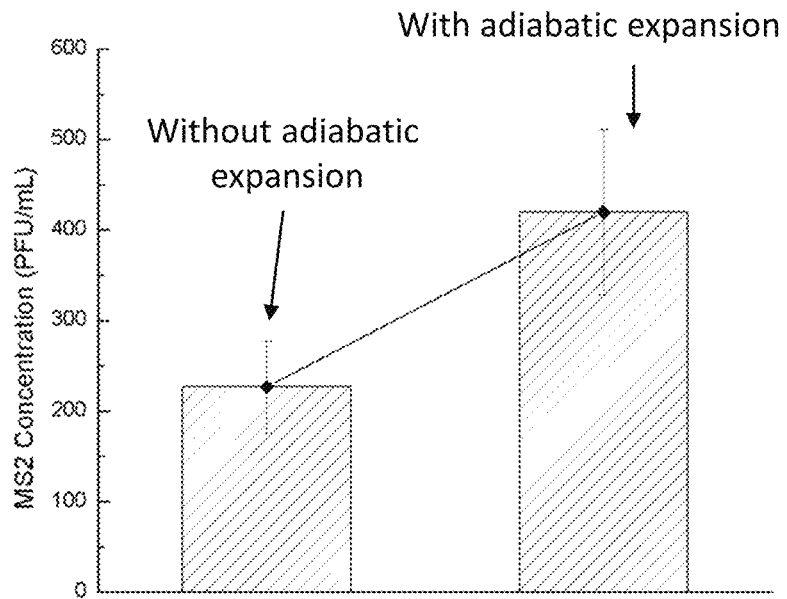
FIG. 12 illustrates concentration of viable MS2 viruses collected with and without adiabatic expansion as described herein.
Figure 13A:
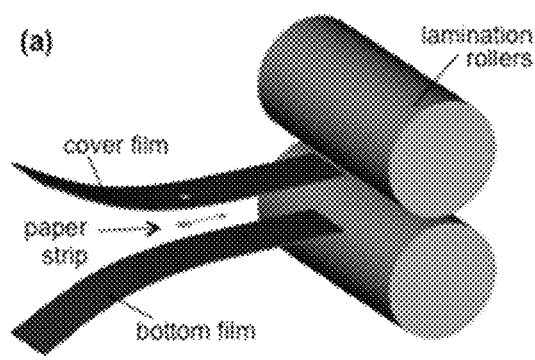
Figure 13B:
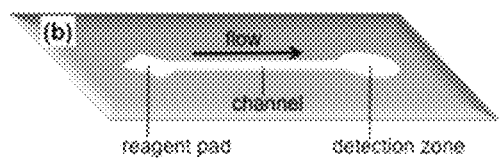
Figure 13C:
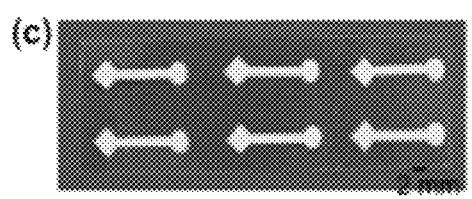
Figure 13D:
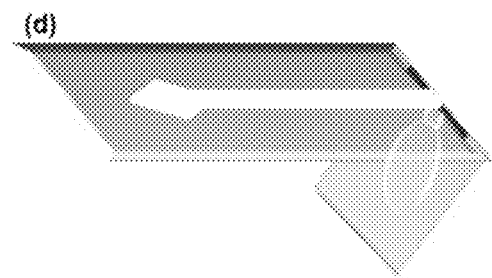
Figure 13E:
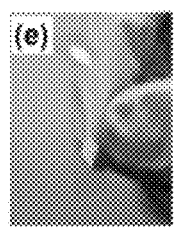
Figure 13F:
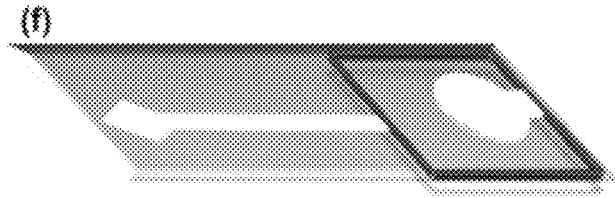
Figure 15A:
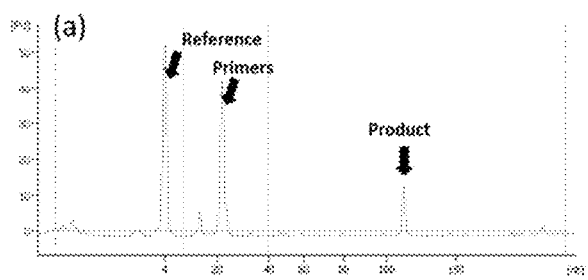
FIGS. 15(a)-(d) show bioanalyzer results of a typical nucleic acid sequence-based amplification (NASBA) reaction showing MS2 and flu viral amplicons.
Figure 15C:
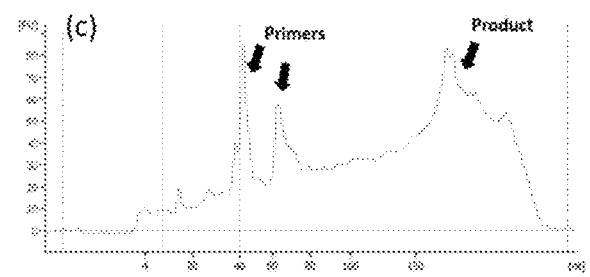
Figure 15B:
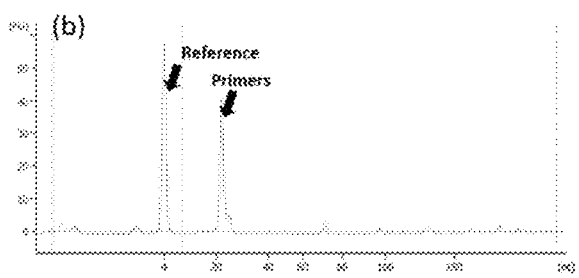
Figure 15D:
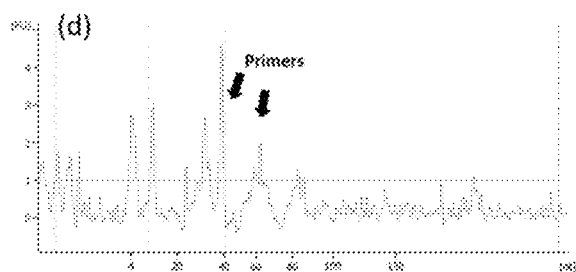

FIG. 12 shows viable MS2 concentration without adiabatic expansion vs. with adiabatic expansion as can be obtained with a BAU and collection reservoir of the present disclosure. As shown, with amplification through the adiabatic expansion, more viable MS2 viruses are collected due to the higher efficiency for larger particles without losing their viability. FIGS. 11 and 12 together demonstrate the system described here within can suitably amplify bioaerosol particles, specifically viral aerosols, and subsequently can allow for more efficient collection.

REFERENCES

Adams, M. H. (1959). *Bacteriophages*, Interscience Publishers, New York. Agarwal, J. K., and Sem, G. J. (1980). "Continuous Flow, Single-Particle-Counting Condensation Nucleus Counter." *J. Aerosol Sci.*, 11(4), 343-357.

Agranovski, V., Ristovski, Z., Hargreaves, M., Blackall, P. J., and Morawska, L. (2003). "Performance Evaluation of the UVAPS: Influence of Physiological Age of Airborne Bacteria and Bacterial Stress." *J. Aerosol Sci.*, 34(12), 1711-1727.

Agranovski, V., and Ristovski, Z. D. (2005). "Real-Time Monitoring of Viable Bioaerosols: Capability of the UVAPS to Predict the Amount of Individual Microorganisms in Aerosol Particles." *J. Aerosol Sci.*, 36(5-6), 665-676.

Akers, T. G. (1973). "Some Aspects of the Airborne Inactivation of Viruses." *Airborne Transmission and Airborne Infection*, J. F. P. Hers, and K. C. Winkler, eds., John Wiley & Sons, New York, 73-81.

Anwar, D., Oh, S., and Wu, C. Y. (2010). "Virus Collection Efficiency of Biosampler Versus Impinger with Variable Time and Flow Rate." BS, University of Florida, Gainesville, FL Aranha-Creado, H., and Brandwein, H. (1999). "Application of Bacteriophages as Surrogates for Mammalian Viruses: A Case for Use in Filter Validation Based on Precedents and Current Practices in Medical and Environmental Virology." *PDA J. Pharm. Sci. Technol.*, 53, 75-82.

Arora, A., Simone, G., Salieb-Beugelaar, G. B., Kim, J. T., and Manz, A. (2010). "Latest developments in micro total analysis systems." *Analytical chemistry*, 82(12), 4830-4847.

Boone, T. D., Fan, Z. H., Hooper, H. H., Ricco, A. J., Tan, H., and Williams, S. J. (2002). "Plastic advances microfluidic devices." *Analytical chemistry*, 74(3), 78A-86A.

Buesser, B., and Pratsinis, S. E. (2011). "Design of Gas-Phase Synthesis of Core-Shell Particles by Computational Fluid-Aerosol Dynamics." *AIChE J.*, 57(11), 3132-3142.

Cassano, C. L., and Fan, Z. H. (2013). "Laminated Paper-based Analytical Devices (LPAD): Fabrication, Characterization, and Assays." *Microfluidics and nanofluidics*, 14, DOI 10.1007/s10404-10013-11140-x.

Cheng, Y. S., Yeh, H. C., and Kanapilly, G. M. (1981). "Collection Efficiencies of a Point-to-Plane Electrostatic Precipitator." *Am. Ind. Hyg. Assoc. J.*, 42(8), 605-610.

Cox, C. S. (1987). The Aerobiological Pathway of Microorganisms, Wiley, Chichester New York Das, C., and Fan, Z. H. (2006). "Effects of separation length and voltage on isoelectric focusing in a plastic microfluidic device." *Electrophoresis*, 27(18), 3619-3626.

Das, C., Zhang, J., Denslow, N. D., and Fan, Z. H. (2007). "Integration of Isoelectric Focusing with Multi-channel Gel Electrophoresis by Using Microfluidic Pseudo-valves." *Lab on a chip*, 7, 1806-1812.

Fan, Z. H., Mangru, S., Granzow, R., Heaney, P., Ho, W., Dong, Q., and Kumar, R. (1999). "Dynamic DNA hybridization on a chip using paramagnetic beads." *Analytical chemistry*, 71(21), 4851-4859.

Fennelly, K., Gray, G., Wu, C. Y., and Lednicky, J. (2011). "Preventing Aerosol Transmission of Influenza." VA-CO-HIC.

Fenton, E. M., Mascarenas, M. R., López, G. P., and Sibbett, S. S. (2008). "Multiplex Lateral-Flow Test Strips Fabricated by Two-Dimensional Shaping." *Acs Applied Materials & Interfaces*, 1(1), 124-129.

Fredrickson, C. K., Xia, Z., Das, C., Ferguson, R., Tavares, F. T., and Fan, Z. H. (2006). "Effects of Fabrication Process Parameters on the Properties of Cyclic Olefin Copolymer Microfluidic Devices." *J Microelectromech S*, 15(5), 1060-1068.

Friedlander, S. L. (2000). 21i Smoke, Dust and Haze: Fundamentals of Aerosol Dynamics, Oxford University Press, New York, NY Grinshpun, S. A., Adhikari, A., Li, C. L., Yermakov, M., Reponen, L., Johansson, E., and Trunov, M. (2010). "Inactivation of Aerosolized Viruses in Continuous Air Flow with Axial Heating." *Aerosol Sci. Technol.*, 44(11), 1042-1048.

Hamilton, S., Wyatt, D., Wahlgren, B., O'Dowd, M., Morrissey, J., Daniels, D., and Lednicky, J. (2011). "Higher Titers of Some H5N1 and Recent Human H1N1 and H3N2 Influenza Viruses in Mv1 Lu vs. MDCK cells." *Virol. J.*, 8(1), 1-9.

Hering, S. V., Stolzenburg, M. R., Quant, F. R., Oberreit, D. R., and Keady, P. B. (2005). "A Laminar-Flow, Water-Based Condensation Particle Counter (WCPC)." *Aerosol Sci. Technol.*, 39(7), 659-672.

Hogan, C. J. J., Kettleson, E. M., Lee, M. H., Ramaswami, B., Angenent, L. T., and Biswas, P. (2005). "Sampling Methodologies and Dosage Assessment Techniques for Submicrometer and Ultrafine Virus Aerosol Particles." *J. Appl. Microb.*, 99, 1422-1434.

Hogan, C. J. J., Lee, M. H., and Biswas, P. (2004). "Capture of Viral Particles in Soft X-Ray-Enhanced Corona Systems: Charge Distribution and Transport Characteristics % J Aerosol Sci. Technol." 38, 475-486.

IOM (2009). "Respiratory Protection for Healthcare Workers in the Workplace Against Novel H1N1 Influenza A: A Letter Report.", C. T. Liverman, T. A. Harris, B. Rogers, and K. I. Shine, eds., National Research Council, Washington, DC Khnouf, R., Beebe, D. J., and Fan, Z. H. (2009). "Cell-Free Protein Expression in a Microchannel Array with Passive Pumping." *Lab on a chip*, 9, 56-61.

Koh, C. G., Tan, W., Zhao, M. Q., Ricco, A. J., and Fan, Z. H. (2003). "Integrating polymerase chain reaction, valving, and electrophoresis in a plastic device for bacterial detection." *Analytical chemistry*, 75(17), 4591-4598.

Koopmans, M., de Bruin, E., Godeke, G. J., Friesema, I., van Gageldonk, R., Schipper, M., Meijer, A., van Binnendijk, R., Rimmelzwaan, G. F., de Jong, M. D., Buisman, A., van Beek, J., van de Vijver, D., and Reimerink, J. (2012). "Profiling of Humoral Immune Responses to Influenza Viruses by Using Protein Microarray." *Clin. Microb. Infect.*, 18(8), 797-807.

Kousaka, Y., Niida, T., Okuyama, K., and Tanaka, H. (1982). "Development of a Mixing Type Condensation Nucleus Counter." *J. Aerosol Sci.*, 13(3), 231-240.

Lednicky, J. A., Hamilton, S. B., Tuttle, R. S., Sosna, W. A., Daniels, D. E., and Swayne, D. E. (2010). "Ferrets Develop Fatal Influenza after Inhaling Small Particle Aerosols of Highly Pathogenic Avian Influenza Virus A/Vietnam/1203/2004 (H5N1)." *Virol. J.*, 7, 15.

Li, X., Ballerini, D. R., and Shen, W. (2012). "A perspective on paper-based microfluidics: Current status and future trends." *Biomicrofluidics*, 6(1), 11301-1130113.

Lin, X., Reponen, T. A., Willeke, K., Grinshpun, S. A., Foarde, K. K., and Ensor, D. S. (1999). "Long-term Sampling of Airborne Bacteria and Fungi into a Non-Evaporating Liquid." *Atmos. Environ.*, 33(26), 4291-4298.

Lu, Y., Shi, W., Jiang, L., Qin, J., and Lin, B. (2009). "Rapid prototyping of paper-based microfluidics with wax for low-cost, portable bioassay." *Electrophoresis*, 30(9), 1497-1500.

Lu, Y., Shi, W., Qin, J., and Lin, B. (2010). "Fabrication and characterization of paper-based microfluidics prepared in nitrocellulose membrane by wax printing." *Analytical chemistry*, 82(1), 329-335.

Martinez, A. W., Phillips, S. T., Butte, M. J., and Whitesides, G. M. (2007). "Patterned paper as a platform for inexpensive, low-volume, portable bioassays." *Angew Chem Int Ed Engl*, 46(8), 1318-1320.

Martinez, A. W., Phillips, S. T., and Whitesides, G. M. (2008). "Three-dimensional microfluidic devices fabricated in layered paper and tape." *Proceedings of the National Academy of Sciences*, 105(50), 19606-19611.

McDevitt, J. J., Koutrakis, P., Ferguson, S. T., Wolfson, J. M., Fabian, M. P., Martins, M., Pantelic, J., and Milton, D. K. (2013). "Development and Performance Evaluation of an Exhaled-Breath Bioaerosol Collector for Influenza Virus." *Aerosol Sci. Technol.*, 47(4), 444-451.

Mei, Q., Fredrickson, C. K., Jin, S., and Fan, Z. H. (2005). "Toxin detection by a miniaturized in vitro protein expression array." *Analytical chemistry*, 77(17), 5494-5500.

Mei, Q., Fredrickson, C. K., Lian, W., Jin, S., and Fan, Z. H. (2006). "Ricin Detection by Biological Signal Amplification in a Well-in-a-Well Device." *Analytical chemistry*, 78(22), 7659-7664.

Mei, Q., Khnouf, R., Simon, A., and Fan, Z. H. (2010). "Protein Synthesis in a Device with Nanoporous Membranes and Microchannels." *Lab on a chip*, 10, 2541-2545.

Mei, Q., Xia, Z., Xu, F., Soper, S. A., and Fan, Z. H. (2008). "Fabrication of Microfluidic Reactors and Mixing Studies for Luciferase Detection." *Analytical chemistry*, 80, 6045-6050.

Milton, D. K., Fabian, M. P., Cowling, B. J., Grantham, M. L., and McDevitt, J. J. (2013). "Influenza Virus Aerosols in Human Exhaled Breath: Particle Size, Culturability, and Effect of Surgical Masks." *PLoS Pathog*, 9(3), e1003205.

Molinari, N. A., Ortega-Sanchez, I. R., Messonnier, M. L., Thompson, W. W., Wortley, P. M., Weintraub, E., and Bridges, C. B. (2007). "The Annual Impact of Seasonal Influenza in the US: Measuring Disease Burden and Costs." *Vaccine*, 25(27), 5086-5096.

Oh, S., Anwar, D., Theodore, A., Lee, J. H., Wu, C. Y., and Wander, J. (2010). "Development and Evaluation of a Novel Bioaerosol Amplification Unit (BAU) for Improved Viral Aerosol Collection." *J. Aerosol Sci.*, 41(9), 889-894.

Prescott, L. M., Harley, J. P., and Klein, D. A. (2006). *Microbiology*, McGraw Hill Companies, Inc., New York, NY Reed, L. J., and Muench, H. (1938). "A Simple Method for Estimating Fifty Percent Endpoints." *Am. J. Hyg.*, 27, 493-497.

Rengasamy, S., Fisher, E., and Shaffer, R. E. (2010). "Evaluation of the Survivability of MS2 Viral Aerosols Deposited on Filtering Face Piece Respirator Samples Incorporating Antimicrobial Technologies." *Am. J. Infect. Control*, 38(1), 9-17.

Shen, F., Tan, M., Wang, Z., Yao, M., Xu, Z., Wu, Y., Wang, J., Guo, X., and Zhu, T. (2011). "Integrating Silicon Nanowire Field Effect Transistor, Microfluidics and Air Sampling Techniques For Real-Time Monitoring Biological Aerosols." *Environ. Sci. Technol.*, 45(17), 7473-7480.

Sheng, W., Chen, T., Kamath, R., Xiong, X., Tan, W., and Fan, Z. H. (2012). "Aptamer-Enabled Efficient Isolation of Cancer Cells from Whole Blood Using a Microfluidic Device." *Anal. Chem.*, 84(9), 4199-4206.

Tan, W., Fan, Z. H., Qiu, C. X., Ricco, A. J., and Gibbons, I. (2002). "Miniaturized capillary isoelectric focusing in plastic microfluidic devices." *Electrophoresis*, 23(20), 3638-3645.

Thompson, W. W., Shay, D. K., Weintraub, E., Brammer, L., Cox, N., Anderson, L., and Fukuda, K. (2003). "Mortality Associated with Influenza and Respiratory Syncytial Virus in the United States." *JAMA*, 289(2), 179-186.

Tseng, C. C., and Li, C. S. (2005). "Collection Efficiencies of Aerosol Samplers for Virus-Containing Aerosols." *J. Aerosol Sci.*, 36(5-6), 593-607.

Verreault, D., Moineau, S., and Duchaine, C. (2008). "Methods for Sampling of Airborne Viruses." *Microb. Molec. Biol. Rev.*, 72(3), 413-444.

Wang, S., Ge, L., Song, X., Yu, J., Ge, S., Huang, J., and Zeng, F. (2012). "Paper-Based Chemiluminescence ELISA: Lab-on-Paper Based on Chitosan Modified Paper Device and Wax-Screen-Printing." *Biosens. Bioelectron.*, 31(1), 212-218.

Whitesides, G. M. (2006). "The origins and the future of microfluidics." *Nature*, 442(7101), 368-373.

WHO (2002). "WHO Manual on Animal Influenza Diagnosis and Surveillance", <http://www.who.int/vaccine_research/diseases/influenza/WHO_manual_on_animaldiagnosis_and_surveillance_2002_5.pdf>. (Jul. 23, 2013).

Woo, M. H. (2012). *Improving Protection against Viral Aerosols through Development of Novel Decontamination Methods and Characterization of Viral Aerosols*, University of Florida, [Gainesville, FL Wu, C. Y., Theodore, A., Lee, J. W., and Riemenschneider, L. (2013). "A High-Efficiency Viable Sampler for Ultrafine Bioaerosols." U.P.a.T. Office, ed., University of Florida Research Foundation, Inc., USA.

Xu, Z. Q., Wu, Y., Shen, F. X., Chen, Q., Tan, M. M., and Yao, M. S. (2011). "Bioaerosol Science, Technology, and Engineering: Past, Present, and Future." *Aerosol Sci. Technol.*, 45(11), 1337-1349.

Yetisen, A. K., Akram, M. S., and Lowe, C. R. (2013). "Paper-based microfluidic point-of-care diagnostic devices." *Lab on a chip*, 13(12), 2210-2251.

Yu, J., Wang, S., Ge, L., and Ge, S. (2011). "A novel chemiluminescence paper microfluidic biosensor based on enzymatic reaction for uric acid determination." *Biosensors and Bioelectronics*, 26(7), 3284-3289.

Example 2

After the viruses are collected in the collector, one way to detect them is based on their unique nucleic acid sequences. An amplification method is typically used in combination with a molecular beacon. The purpose of the amplification in this example is to increase the copy number of nucleic acids contained in the collected viruses and then allow them to be detected reliably above a threshold or noise floor. The amplification methods can include polymerase chain reactions (PCR) and variations thereof, a number of linear amplification methods, and other signal amplification methods. Several examples are discussed below.

In-Tube NASBA with Molecular Beacon

Figure 17:
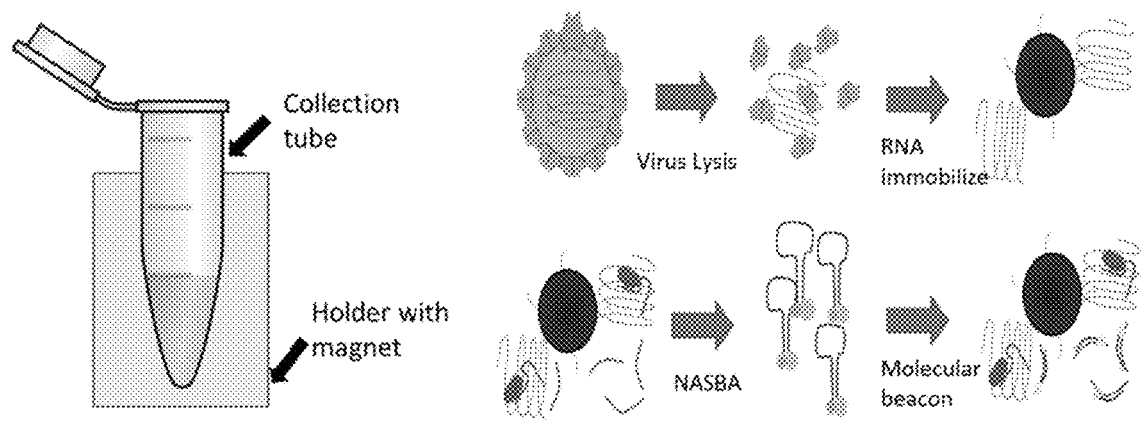
FIG. 17 demonstrates an exemplary scheme for viral detection using NASBA. The NASBA reaction can be carried out in a centrifugal collection tube with the assistance of magnetic beads and a magnetic collection tube holder.

This detection scheme can detect the fluorescence signal of molecular beacons generated from NASBA amplicons. An exemplary scheme is shown in FIG. 17. After the virus particles are collected in the collector tube, a concentrated virus lysis solution can be added along with magnetic silica beads. The beads with an appropriate coating can capture nucleic acid[s] (e.g., RNA from MS2 or flu viruses) released by the viral lysis step. Then, a device such as a magnetic holder can be used to attract the beads to the bottom or the side of the collection tube, which can allow the supernatant to be removed and allow for subsequent simple wash steps and/or reagent addition[s]. With the same method, required washing steps can be performed before the NASBA reaction mix and molecular beacons being added to the tube. NASBA can then be performed by heating the closed collection tube. If the target virus is present, the molecular beacons can generate fluorescence signal which could be detected and analyzed by an optical device, for example a smartphone with lens, imaging sensor, and an application configured to receive and process data from the imaging sensor, and a display configured to display data from the application.

Amplification of Virus RNA with NASBA

Nucleic acid sequence-based amplification (NASBA) can been used to amplify RNA extracted from viruses, such as MS2 and influenza viruses. RNA from MS2 and flu viruses can be extracted using a commercially available kit, for example the QIAamp® RNA mini kit (QUIAGEN). The NASBA reaction mix cab be prepared in house with reagents from a commercial vendor such as Fisher Scientific®. The primers involved can be designed based on sequences of interest found in databases, such as NCBI (GenBank: NC_001417.2 can be used for MS2, GenBank: AY139081.1 can be used for flu), and reaction can be carried out at 42° C. for 2 hours. The resulting amplicon of interest can be confirmed by electrophoresis using an Agilent 2100 Bioanalyzer Instrument. The results of a typical NASBA reaction showing MS2 and flu viral amplicons are shown in FIGS. 15(a)-(d).

Example 3

In-Tube Amplification of Flu Virus RNA with Colorimetric Reverse Transcription Loop-Mediated Isothermal Amplification (RT-LAMP)

Reverse transcription loop-meditated isothermal amplification (RT-LAMP) can be used to amplify flu virus RNA. Colorimetric detection can be achieved by using SYBR Green I under UV light and phenol red under ambient light. The preparation of flu virus RNA can be done as described in the section above. RT-LAMP mixture can be prepared in house with commercially available reagents from vendors such as Fisher Scientific® and New England BioLabs®. The RT-LAMP reaction can be carried out at 63.5° C. for 1 hour. The amplicon can be confirmed both by eye and agarose gel electrophoresis. An example of the result of flu virus RT-LAMP is shown in FIGS. 16(a)-(b). With RT-LAMP method, about 10 $TCID_{50}$ flu virus RNA copies can be detected in a 25 µL PCR tube.

Example 4

ELISA-Based Detection with an Immiscible Phase Separation Device

Figure 18A:
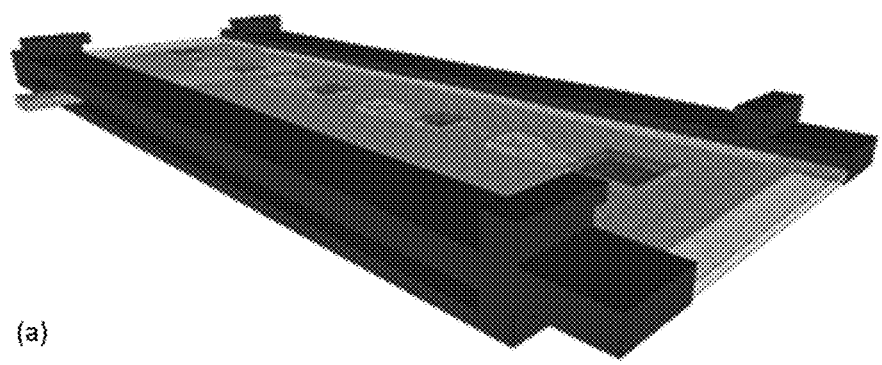
FIG. 18(a)-(b) illustrates an embodiment of an immiscible phase separation device that can be used to carry out detection assays such as an enzyme-linked immunosorbent assay (ELISA) in a point-of-care format.
Figure 18B:
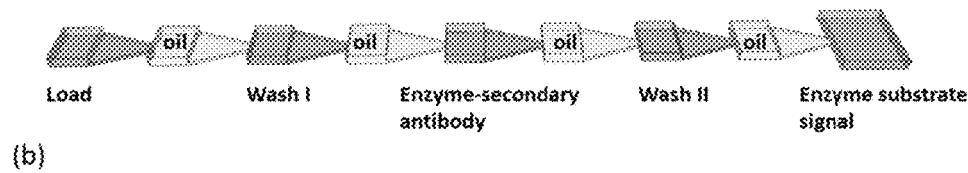
Figure 19A:
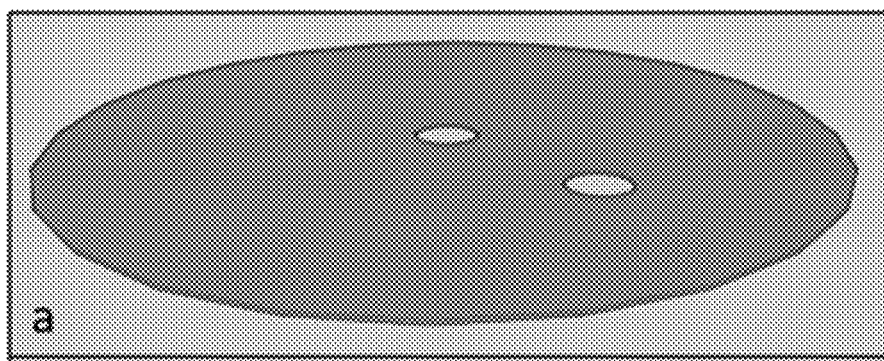
FIGS. 19(a)-(f) demonstrates an embodiment of an LPAD, which can be designed and configured to perform virus lysis, RNA extraction, and RT-LAMP detection all together in one device.
Figure 19B:
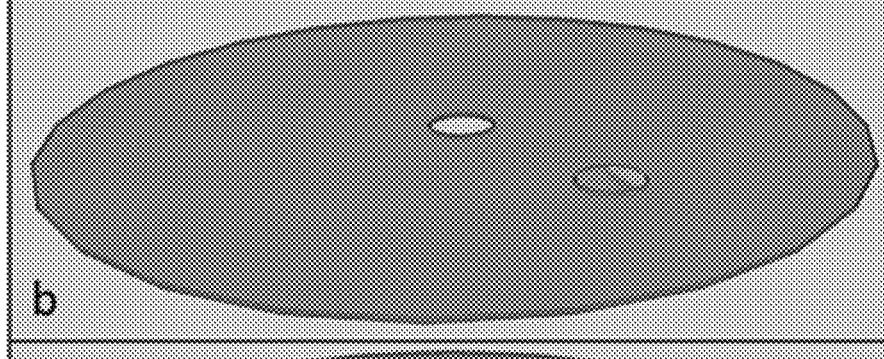
Figure 19C:
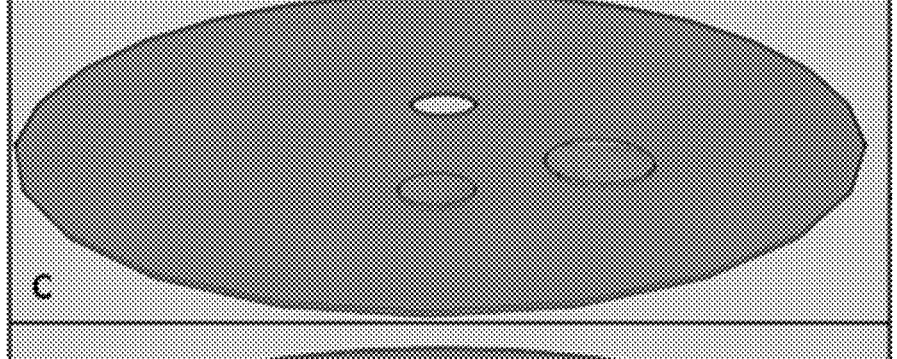
Figure 19D:
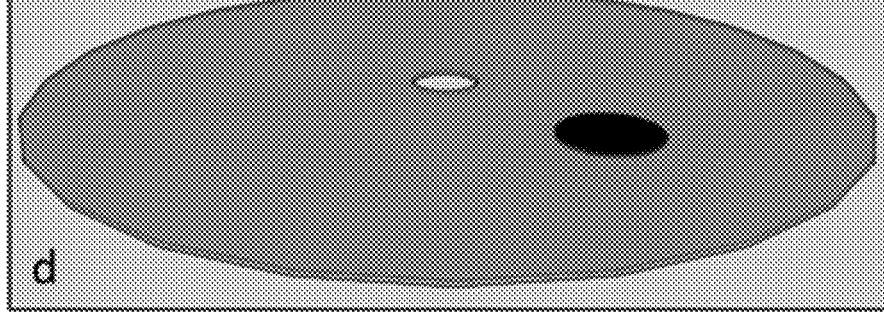
Figures 19E, 19F:
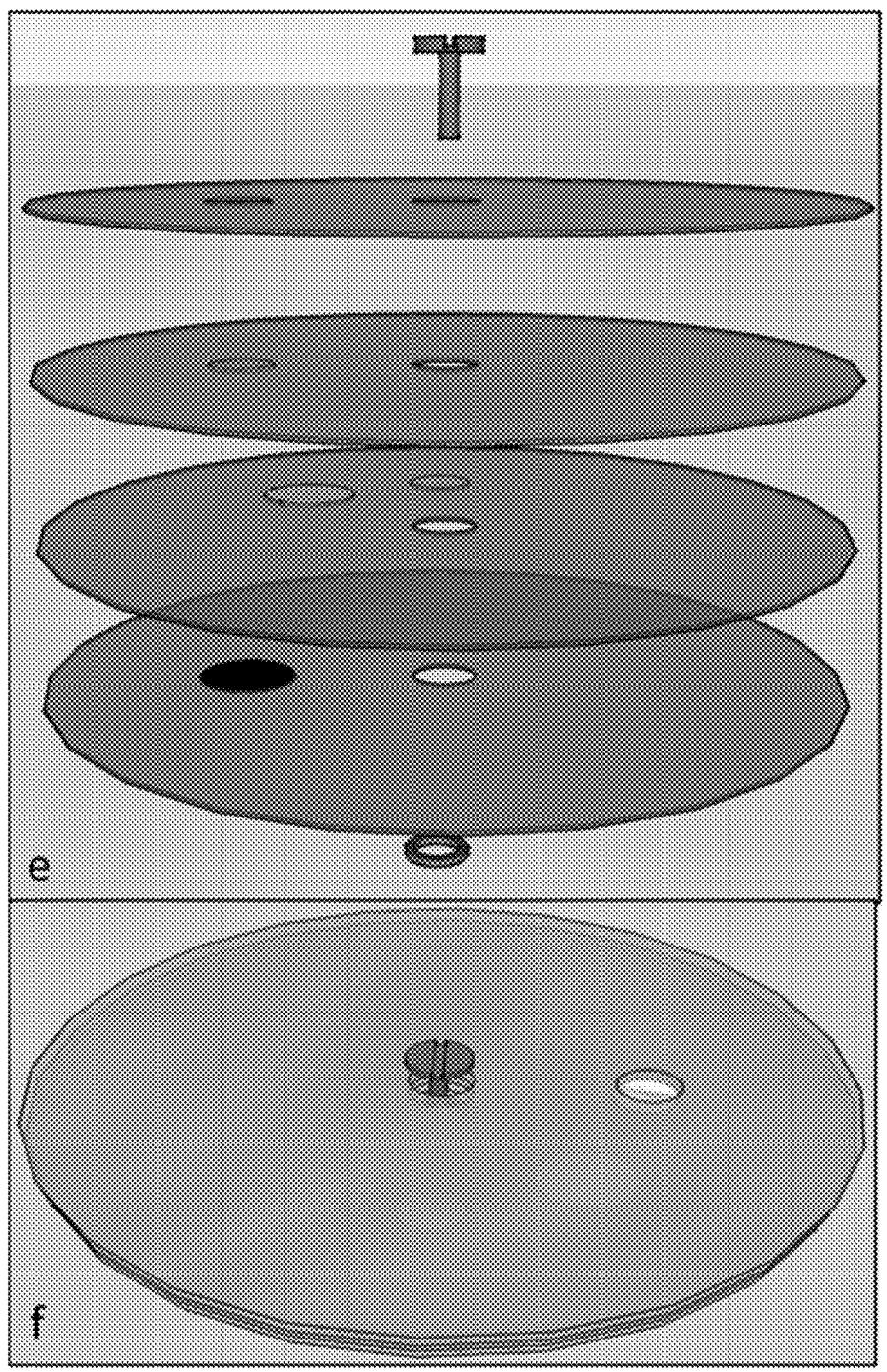

Another example of a detection scheme is based on immunoassays like enzyme-linked immunosorbent assay (ELISA). To perform ELISA in a point-of-care format, an immiscible phase separation device as shown in FIGS. 18(a)-(b) can be used. As shown in FIG. 18(a) this device can have connected aqueous phase chambers separated by oil plugs. The oil plugs would prevent the aqueous phases from mixing with each other while allowing magnetic beads to pass by (guided by moving a magnet along). To perform the detection, magnet beads conjugated with antibodies can be loaded into the collection tube, and then transferred into the first chamber of the device as described in the previous section. After these magnetic beads interact with target viruses, a user can simply pull the magnet placed beneath the device to move the beads through the oil phase to next chamber. Different chambers for washing and other steps are required as needed and shown in FIG. 18b. If the target viruses are present in the collection tube, a colorimetric, fluorescent, or luminescent signal would be generated at the last chamber of the device, as practiced in the last step in traditional ELISA. The immunoassay in this example can be configured to detect viral components, such as proteins and/or nucleic acid[s].

Example 5

Colorimetric RT-LAMP on Paper-Based Lamination Disc Device

Figure 20A:
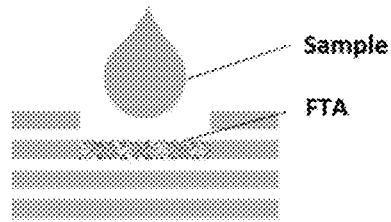
FIGS. 20(a)-(d) show an exemplary scheme for RT-LAMP and colorimetric detection based on the embodiment of the LPAD of FIGS. 19(a)-(f).
Figure 20A:
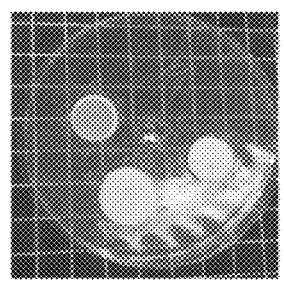
Figure 20B:
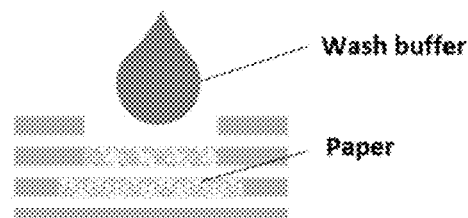
Figure 20B:
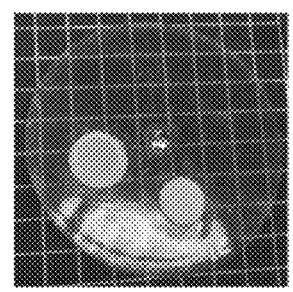
Figure 20C:
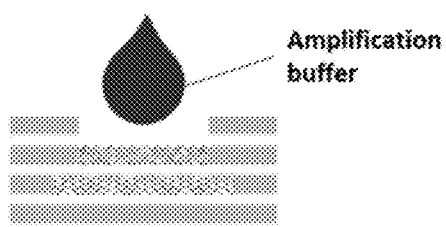
Figure 20C:
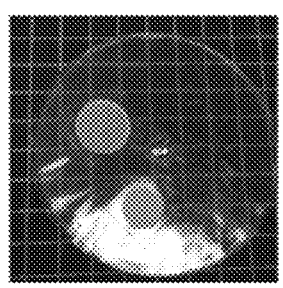
Figure 20D:
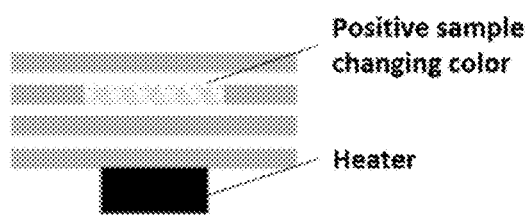
Figure 20D:
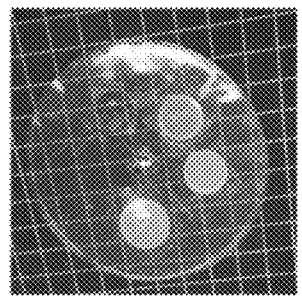

This detection scheme is based on colorimetric RT-LAMP mentioned previously. In this scheme, an LPAD is described which can be designed and configured to perform virus lysis, RNA extraction, and RT-LAMP detection all together in one device. As shown in the example in FIGS. 19(a)-(f), this device can include four layers, all of which can be fabricated with heat lamination with thermoplastic film and PDMS coating. The first layer can include a sample loading port. The second layer can include an RNA extraction unit made of a paper that can capture and store nucleic acids, such as a commercially available Whatman® FTA card, chromatography paper, or glass-fiber-based paper. The third layer can include multiple cellulose paper discs and can provide the capillary forces necessary for washing. The fourth layer can include a small heater. These four layers can be integrated together with a device, such as a screw through the hole in the middle of each layer, or other means. To perform the detection, a user can rotate the layers to the place shown in FIG. 20(a). Then, the sample can be loaded through the loading port to the FTA card, allowing the sample to dry at room temperature or standard conditions. In the second step, the user can rotate the layers to the place shown in FIG. 20(b). Then, the washing buffer could be added, and the wash step can be performed by the capillary forces provided by the paper disc in the third layer. The third step can comprise adding RT-LAMP buffer or an amplification buffer in a way similar to the second step as shown in FIG. 20(c). In the final step, the layers can be rotated as shown in FIG. 20(d), and then the heater can be turned on to induce DNA amplification. If the target virus is present in the collection solution, RT-LAMP colorimetric mix can change color after the final step as shown in FIG. 16(b).

Example 6

LPAD Virus Detection Device Design and Fabrication

Figure 21A:
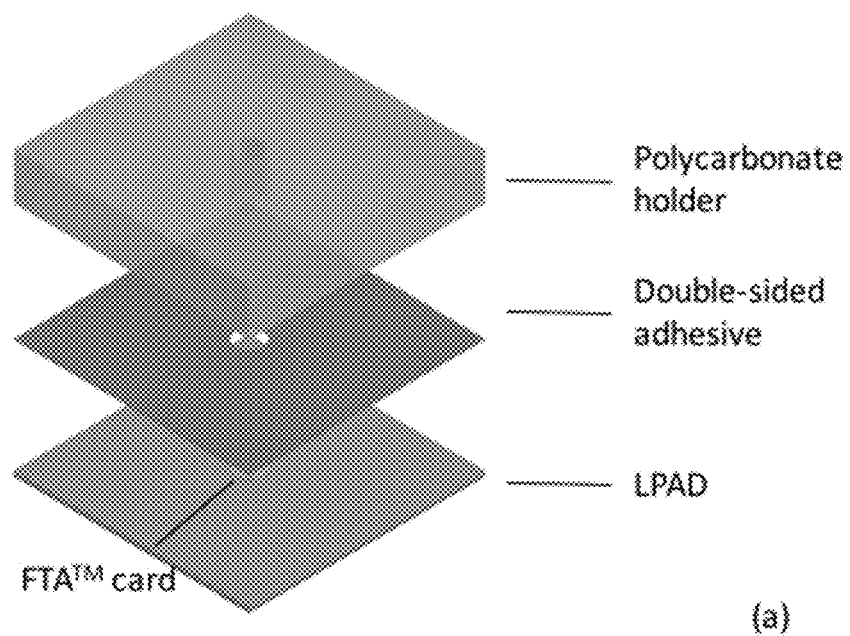
FIGS. 21(a)-(b) illustrate an embodiment of an LPAD device for virus detection, such as nucleic acid virus detection.
Figure 21B:
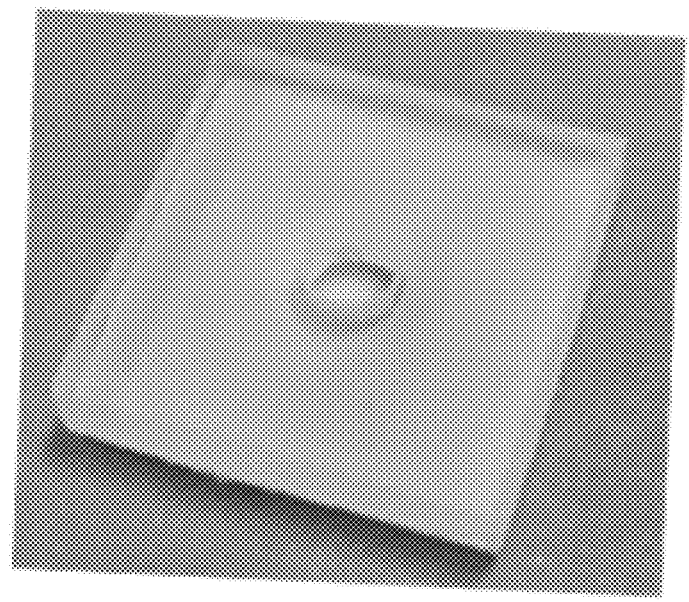

An LPAD virus detection device can comprise a laminated paper-based RNA purification pad, a double-sided adhesive layer, and a polycarbonate (PC) holder, as shown in FIG. 21(a). FIGS. 21(a)-(b) show an embodiment of an LPAD device which can be used for virus detection, nucleic acid-based virus detection for example. FIG. 21(a) shows an embodiment of construction of a device and FIG. 21(b) shows a photograph of a device. The laminated paper-based RNA purification pad can be made by laminating a punch of FTA™ card (Whatman) or other paper between two layers of thermo-lamination film. The whole device can be assembled by aligning the holes shaped within the double-sided adhesive layer and the PC holder with the FTA™ punch, and pressed together to bond (FIG. 21(B)).

Testing the Detection Limit Using H1N1 Flu Virus

To operate the device, in an embodiment, virus-containing liquid sample can first be mixed with lysis buffer and ethanol to obtain RNA from virus capsids, then loaded to the laminated paper-based RNA purification pad (LPAD) through the device center hole. A paper pad can be pressed against the bottom of the device to provide capillary force to filter the sample solution through the FTA™ punch. Meanwhile, the RNA in the sample can be immobilized onto the FTA™ punch, and then purified by washing with wash buffers in the same manner. The purified RNA was dried for 20 minutes in room temperature before RT-LAMP. After drying, the bottom of the device was sealed with a piece of transparent tape or PCR-tape. RT-LAMP buffer was then added into the device, followed by sealing the top of the device with another piece of transparent tape or PCR-tape. Incubation was done by a 40-minute-65° C.-water bath, a microheater, or other means. The amplicons could then be verified with either colorimetric methods, traditional gel electrophoresis, or other amplicon detection methods.

Figure 22A:
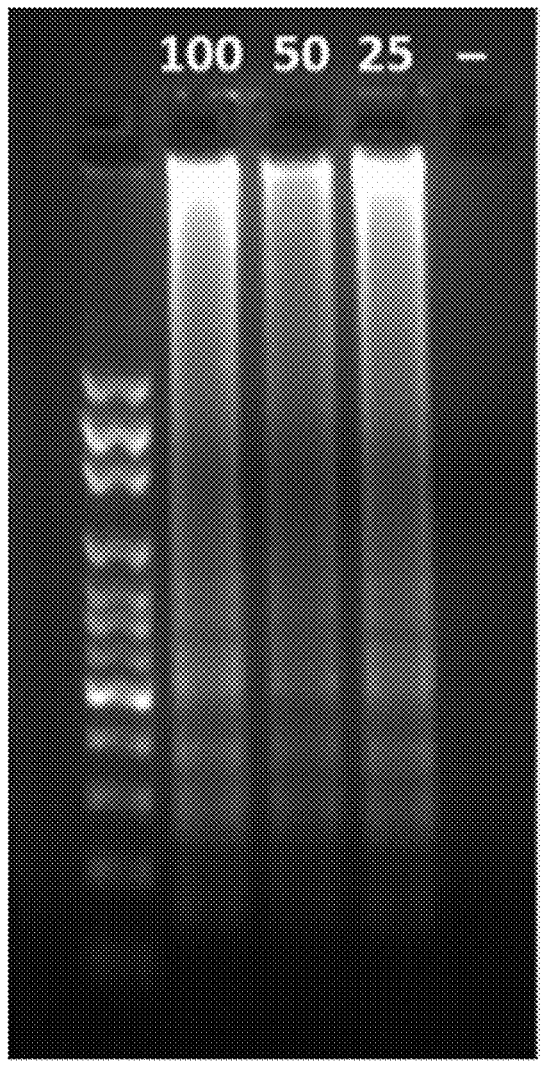
FIGS. 22(a)-(b) shows an embodiment of detection of H1N1 flu virus RNA using the device of FIG. 21 verified by agarose gel staining. The labels above the lanes mark the TCID50 number of flu virus tested in the device, and the "−" marks the negative control.
Figure 22B:
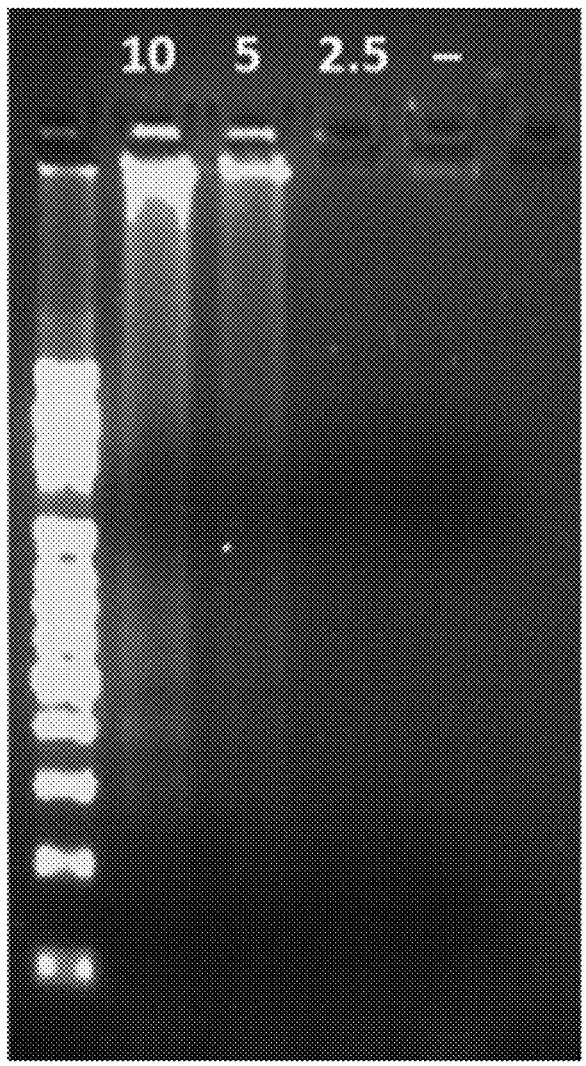

FIGS. 22(a)-(b) show an embodiment of detection of H1N1 flu virus RNA using an embodiment of the device verified by agarose gel electrophoresis stained with ethidium bromide. The left lane of each image is a 100 bp DNA ladder. The TCID50 number of flu viruses put in a device is marked above each lane, with the "−" marks the negative control. The detection limit was obtained by testing with 100, 50, 25, 10, 5, 2.5, and 0 (as negative controls) TCID$_{50}$ H1N1 flu viruses in each device. As shown in FIGS. 22(a)-(b), gel electrophoresis and ethidium bromide staining confirmed that this device could detect down to 5 TCID$_{50}$ H1N1 flu viruses.

Demonstration of in-Device Colorimetric Detection

Both pH-sensitive dye (using phenol red) and DNA-intercalating dye (using SYBR Green I) were tested to demonstrate colorimetric detection. In pH-sensitive dye based method, a buffer-free RT-LAMP solution was prepared in house to allow pH changes during nucleic acid amplification. FIGS. 23(a)-(d) is a demonstration of an embodiment of in-device colorimetric H1N1 flu virus detection using phenol red and SYBR Green I dye. "+" marks a positive sample while "−" marks the negative control. FIG. 23(a) shows embodiments of two devices with phenol red RT-LAMP buffer before incubation. FIG. 23(b) shows the two devices after incubation, positive sample device turns to orange from pink. FIG. 23(c) shows RT-LAMP buffer incubated in the device observed under ambient light after adding SYBR Green I dye. The positive sample shows a light yellow color while the negative sample shows a darker yellow color. FIG. 23(d) show the two samples observed under a blue LED flashlight. The positive sample (left) has a green fluorescence.

As shown in FIG. 3(a), the RT-LAMP solution had a pinkish color from the pre-added phenol red before incubation. After incubation, the RT-LAMP solution from the positive device (containing the target virus) turned yellow as the pH decreased, while the negative control remained pink (FIG. 3(b)).

In DNA-intercalating dye method, SYBR Green I dye was added post-incubation. The RT-LAMP solutions between the positive device and negative control have a slight color difference observed under ambient light (FIG. 3(c)). Using a common blue LED flashlight, a strong green fluorescence was observed in the positive device (FIG. 3(d)), guaranteeing effortless result reading.

Example 7

An Efficient Virus Sampler Enabled by Adiabatic Expansion

Adiabatic expansion, includes an instant volume expansion whereby there is no heat transfer between the contained volume and its surroundings (Bailyn, 1994). For a system with a certain volume, the temperature, volume and pressure of the system before and after the adiabatic-expansion are related as follows:

$$P_0 V_0^\gamma = P_f V_f^\gamma \tag{1}$$

$$T_0 V_0^{\gamma-1} = T_f V_f^{\gamma-1} \tag{2}$$

where P, V, T are pressure, volume and temperature, respectively, subscripts 0 and f refer to before and after adiabatic expansion, respectively, and γ is the ratio of specific heat of relevant gas at a constant pressure over that at a constant volume (Strey et al., 1986). Aitken (1888) implemented this principle to create supersaturation by lowering temperature of the surrounding air of target dust aerosol. Pollak and O'Connor (1955) applied this principle in their photoelectric condensation nucleus counter (CNC), wherein a photoelectric sensor was used to count the number of enlarged mist particles. Pollak and Metnieks (1960) investigated the performance of the CNC under different volume expansion ratios $$\left(\text{i.e., } \frac{P_f}{P_o}\right)$$

and achieved a high saturation ratio of 3.50 under a compression ratio of 1.21, which exceeded the required Kelvin ratio for ultrafine particles (Miller & Bodhaine, 1982b). In their research, the CNC successfully amplified particles as small as 20 nm (Miller & Bodhaine, 1982a). Compared to the mixing and cooling approaches, the adiabatic expansion approach can result in an extremely high supersaturation ratio instantly, which activates the growth of particles in a very short time. This high supersaturation ratio played a key role in activating amplification of ultrafine particles as small as 13 nm (Liu et al., 1984). While there have been a handful of studies on size enlargement of particles using adiabatic expansion as discussed, there is no study regarding size enlargement of virus aerosol by this approach yet.

The present example was embarked to apply the adiabatic expansion principle to engineer a highly efficient size amplification device to address limitations associated with previously mentioned methods. On this ground, a prototype of Batch Adiabatic-expansion for Size Intensification by Condensation (BASIC) sampler was designed and fabricated. The BASIC sampler described herein is an embodiment of a BADS as described previously. Performance of the BASIC in regard to size amplification was evaluated. Since collection of viable virus aerosol was a major purpose for the new device, experiments were conducted to evaluate its ability in collecting viable viruses. To optimize the BASIC's operation, sensitivity analyses on key parameters were conducted, including compression pressure, number of compression/expansion cycles (C/E cycles), temperature of the condensing water, and dwell time after the expansion.

Materials and Methods

Design of the Basic

The BASIC consisted of an expansion bag in a chamber. The bag contained the aerosol sample while the chamber was used for providing a room for exertion of compression to and subsequent expansion of the bag (see FIGS. 24(a)-24(c)). Certain amount of de-ionized (DI) water was placed inside the expansion bag as the source for volatile vapor for later condensation on the aerosol sample trapped inside the bag. The DI water also served as the medium for collecting the amplified viruses. The BASIC device can be about 21 inches high and about 4 inches in diameter.

Experimental Setup

Figures 24A, 24B, 24C, 24D:
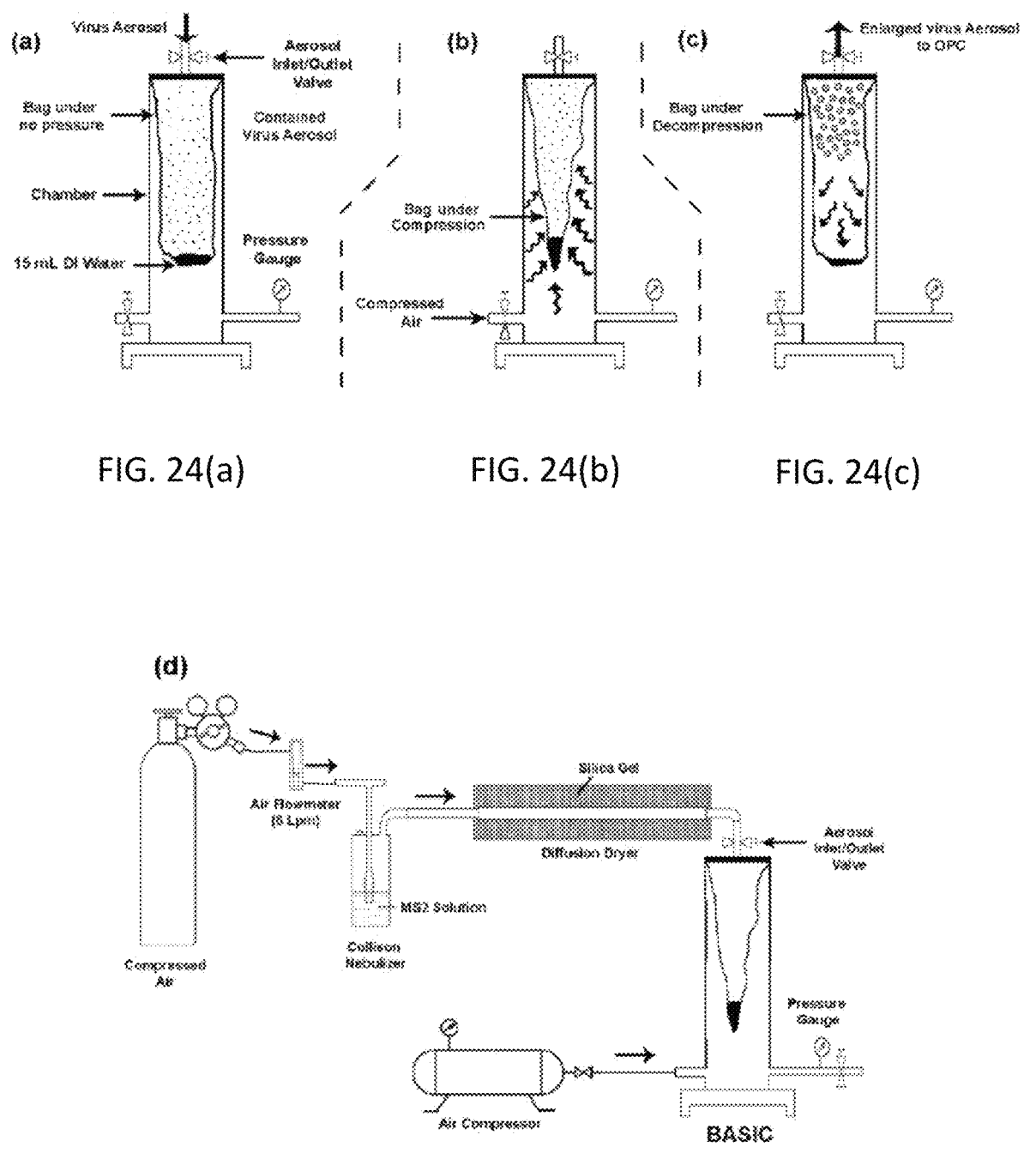

A schematic diagram of the experimental set-up is shown in FIG. 24(d). First, compressed air was directed to a 6-jet Collison nebulizer (Model CN25; BGI Inc., Waltham, MA, USA) at a controlled flow rate of 6 Lpm to generate the aerosol flow. A diffusion dryer was positioned at the outlet of the nebulizer to remove the water content of the aerosol. Before the aerosol was directed into the BASIC, the expansion bag was deflated by filling the chamber with compressed air. Then, the sample aerosol flow was directed into the expansion bag from the aerosol inlet port to fill the bag (FIG. 24(a)) while the air discharge valve was open to release the air in the chamber. Once the bag was fully filled, aerosol introduction was stopped and compressed air was fed to the chamber instead to increase the chamber pressure. After reaching the targeted compression pressure, the air discharge valve was opened rapidly to swiftly drop the chamber's pressure down to the atmospheric pressure level. Thus, the bag expanded instantly, and supersaturation condition was realized inside the expansion bag. This process enabled the particles contained inside the bag to be amplified by water condensation as temperature rapidly decreased due to the swift pressure decrease.

Experimental Procedure

Physical Size Amplification

Performance evaluation of the BASIC was split into two phases. In Phase 1, the physical size amplification was investigated. Amplified aerosol inside the expansion bag was discharged and directed to an Optical Particle Counter (OPC Model 1.108, Grimm® Technologies Inc., Douglasville, GA, USA; size range 0.3-20 μm) for measurements of total number concentration and count median diameter (CMD) of the supermicron particles (i.e., $d_p \geq 1$ μm). The CMD was determined using a log-probability plot of the measured size distribution for locating the corresponding diameter of 50% cut-off point of the accumulative number concentration (Hinds, 1999). Control groups were also included by simply introducing the same sample aerosol into the expansion bag without application of any C/E cycle.

Viability Preservation

Due to its harmless characteristic to humans and robust survivability, MS2 (a bacteriophage that only parasitizes male *Escherichia coli* (*E. coli*) bacteria (Davis et al., 1961) and has an approximate particle size of 28 nm) is widely used as a surrogate in research of small airborne viruses and enteric viruses (Dawson et al., 2005; Zuo et al., 2014). In Phase 2 of this study, MS2 (#15597-B1, ATCC®, Manassas, VA, USA) was used as the challenge virus aerosol. The viability of MS2 bacteriophage in the BASIC was studied by shaking the bag to collect the amplified virus aerosol into the water medium in the expansion bag. A single-layer virus plaque assay (VPA) technique was applied to the collected medium following the standard operating procedures provided by US Environmental Protection Agency (USEPA, 1984).

Lyophilized MS2 bacteriophage was diluted in 100 mL DI water to make a stock suspension with a titer of around $10^{11}$ PFU/mL and stored in a refrigerator under 4° C. Prior to use, 1 mL MS2 stock suspension was pipetted and diluted into 100 mL DI water to create a titer of $10^9$ PFU/mL. *E. coli* (#15597, ATCC®, Manassas, VA, USA) was used in VPA as the indicator host cells for MS2 bacteriophage. *E. coli* powder was aseptically inoculated onto a tryptone yeast extract agar (TYA) plate overnight, and then a single uniform colony on the plate was aseptically picked and inoculated into sterile tryptone yeast extract broth-1 (TYB-1), and incubated overnight to create an *E. coli* stock suspension. Prior to each experiment, 1 mL *E. coli* stock suspension was cultivated in 30 mL TYB-1 for 6 h to obtain log phase cells of an appropriate concentration. All incubations were held at 37° C.

In the single-layer VPA method, TYA was adopted as the plaque assay medium. TYA contained 1.0 g tryptone, 0.1 g yeast extract, 0.1 g glucose, 0.8 g sodium chloride (NaCl), and 0.022 g calcium chloride ($CaCl_2$) per 100 mL of medium with 1.0 g additional agar. Tryptone yeast extract broth Type 2 (TYB-2) with all ingredients in TYA except agar was made for dilution of the samples. TYB-1 that contained only tryptone, yeast extract and sodium chloride were also used for cultivating *E. coli*, 6 h prior to each experiment.

Proper dilution was conducted for samples collected from the expansion bag. Preliminary tests determined that the dilution factors should be 1 and 10 (i.e., the original and 1/10 factors were adopted for the assays). The agar was kept in a warm water bath at −50° C. to maintain its fluidity. Nine mL TYA, 1 mL serial diluted sample and 0.5 mL *E. coli* TYB-1 solution were mixed, vortexed and then poured into a Petri dish and gently shaken for spreading the agar evenly. Afterwards, the Petri dish was placed bottom-up in an incubator at 37° C. where agar could solidify.

After the overnight incubation, viable virus lysed *E. coli* cells and plaques appeared on the bottom of the Petri dish. Only Petri dishes that contained 10-100 plaques were used for counting plaque forming unit (PFU) in order to provide an accurate count (Cormier & Janes, 2014). By multiplying PFU with the dilution factor, the titer of the viable MS2 $C_{viable}$ (PFU/mL) was determined, using Eq. (3).

$$C_{viable} = \frac{PFU_{onplate} \times DF}{V} \qquad (3)$$

where DF is the dilution factor and V is the volume of the diluted sample.

Sensitivity Analyses

Compression pressure, number of C/E cycles and water temperature were varied for sensitivity analyses of the physical size amplification, while dwell time was also included for evaluation of the viability preservation. Sensitivity analyses were carried out by the experimental design shown in Table 1 (below) with the baseline set of variables being 103.5 kPa of compression pressure, one C/E cycle and 25° C. of DI water temperature in physical size amplification tests. No uniform baseline set of values was set in the viability preservation tests. Instead, each experimental run was paired with a control group (no application of any C/E cycle) and performed on the same day (due to the high variability of the results of VPA test on different days).

TABLE 1

Experimental design of sensitivity analyses on physical size amplification and viability preservation

| Group Number | Compression Pressure (kPa) | Number of C/E Cycles | Water Temperature (° C.) | Dwell time (s) | Purpose |
|---|---|---|---|---|---|
| Control Baseline | No Adiabatic Expansion | | | | |
|  | 103.5 | 1 | 25 | 0 | Physical |
| I | 69.0, 138.0 | 1 | 25 | 0 | Performance |
| II | 103.5 | 3, 5 | 25 | 0 | Evaluation |
| III | 103.5 | 1 | 40 | 0 | |
| Control | No Adiabatic Expansion | | | | |
| IV | 69.0, 103.5, 138.0 | 1 | 25 | 0 | Biological Performance |
| V | 103.5 | 1, 3, 5 | 25 | 0 | Evaluation |
| VI | 103.5 | 1 | 25, 40, 60 | 0 | |
| VII | 103.5 | 1 | 25 | 0, 30, 60, 120 | |

The VPA method was conducted on the samples according to the group wherein the sensitivity analysis was conducted. The viable MS2 titer of each sample was then calculated and compared for viability preservation assessment. In order to monitor the stability of MS2 viability in the Collison nebulizer, the titer of viable MS2 in the nebulizer reservoir was also measured for each group. An additional experiment to estimate the rate of aerosol generation was conducted by monitoring the liquid volume remained in the Collison nebulizer at different times; the consumption rate of MS2 suspension was determined using the slope of the linear regression of the data points. The total count of viable MS2 in the expansion bag fed by the nebulizer reservoir was determined using Eq. (4), assuming no loss while transporting and nebulizing.

$$A_{viable}(\text{nebulizer}) = C_{viable}(\text{nebulizer}) \times CR \times t \quad (4)$$

where $A_{viable}$ is the count of viable MS2 consumed in the reservoir (PFU), CR is the consumption rate (mL/min), $C_{viable}$ (nebulizer) is the titer of viable MS2 in the Collison nebulizer reservoir (PFU/mL), and t is the sampling time (10 s in all experiments).

Quality Control and Data Analysis

Prior to each experiment, the aerosol generation system was stabilized for 15 min to ensure the variations of the flow rate within ±0.1 Lpm. Since aerosol size enlargement is realized through water vapor condensation, relative humidity of the incoming aerosol stream should be minimal. Measurement of relative humidity before and after the diffusion dryer showed the relative humidity averagely decreased from ~80% to ~35%. After each experiment, the bag was rinsed by 70% isopropyl alcohol and DI water. Ten mL of DI water was then poured into the bag as the condensing medium right before the next experiment, and the temperature of the DI water was immediately measured by an Infrared Thermometer (Etekcity® Co. Ltd., Anaheim, CA, USA). The expansion bag was then sealed with a lid and held to the chamber to be vacuumed. In viability evaluation experiments, all test tubes and solutions were autoclaved at 120° C. and 1 atm for at least 30 min after each experimental run.

It should be noted that maintaining the water temperature at the highest tested temperature of 60° C. from the time it was poured into the expansion bag to when the adiabatic expansion was applied, was challenging. Based on our measurements right after application of one C/E cycle, temperature of the DI water dropped from 60° C. to 40° C. (%50) for the experimental run of 60° C., and dropped from 40° C. to 35° C. (%12.5) for the experimental run of 40° C. In other word, due to the temperature decrease of the control volume caused by adiabatic expansion, DI water temperature could not maintain its original value, and the temperature drop was larger at the higher initial temperature.

To assess the statistical validity, each experimental condition was triplicated. To analyze the data obtained from the BASIC, a 2-tailed t-test for unequal variance was implemented for comparing the statistical significances between the baseline group and the control group. One-way analysis of variance (ANOVA) was applied for in-group comparison and a post-hoc test using Bonferroni's method was applied for comparison of two subgroups within a group.

Results and Discussion

Physical Size Amplification

Compression Pressure

Figures 25, 26A:
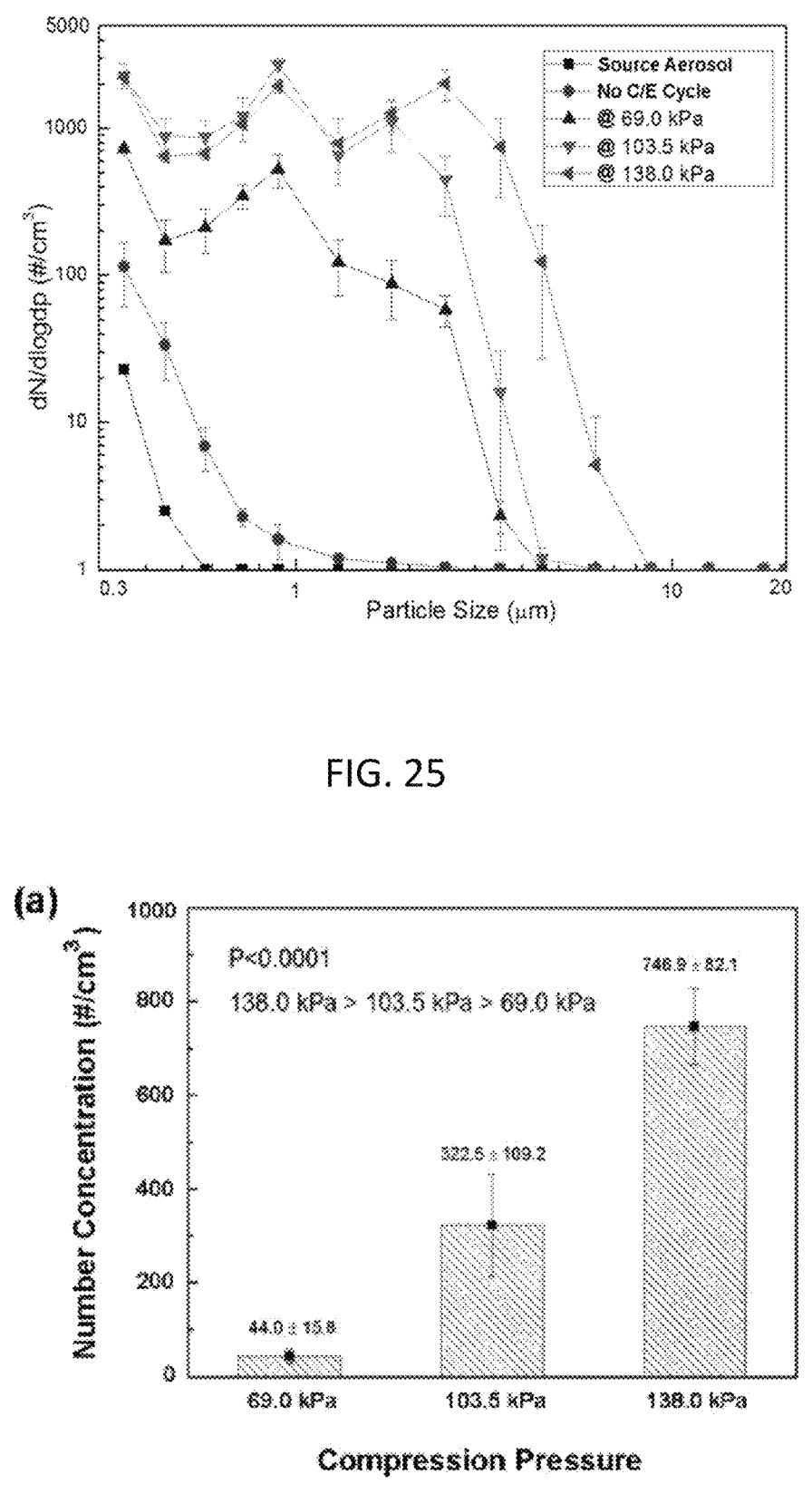

Size distributions of the aerosol with different compression pressures and without adiabatic expansion are displayed in FIG. 25. FIG. 25 shows the physical size distributions of MS2 aerosol (i.e. concentration as a function of particle size) amplified by the adiabatic expansion process. The measurement was done using an Optical Particle Counter that measures sizes of 0.3 μm and above. The source aerosol was mainly smaller than 0.3 μm (hence only a small fraction above 0.3 μm was detected). As the compression pressure for inducing adiabatic expansion increased from 69 kPa to 103.5 kPa to 138 kPa, the number of supermicron (<1 μm) aerosol particles increased. The axes are in log-scale. As shown, a fraction of submicron (0.3-1.0 μm) particles picked up some moisture content and were amplified slightly even in the absence of a C/E cycle. In the baseline group, after application of only one C/E cycle at the compression pressure of 103.5 kPa, anincrease of particles was observed: the largest particle size detected after one C/E cycle was ~4 μm, and the number concentration of supermicron particles compared to the source aerosol was very high (>300 #/cm³). An increase in compression pressure resulted in an improved size amplification performance, and the number concentration increased further. When compression pressure increased from 69.0 kPa to 103.5 kPa, the number concentration increased 4 to 5 times in the submicron size range, and the largest particle size increased from 2.5 μm to >4 μm. At compression pressure of 138.0 kPa, the largest size of amplified particles exceeded 5 μm and a very obvious increase of number concentration in the supermicron range took place.

The t-test results of number concentration of the supermicron particles between groups with (control group) and without adiabatic expansion (baseline group) are displayed in Table 2:

TABLE 2

Number concentration and count median diameter (CMD) of supermicron particles in the air sample from the BASIC, with and without adiabatic expansion

|  | Number concentration (#/cm³) | Count median diameter (μm) |
|---|---|---|
| Without adiabatic expansion (Baseline) | 0.058 ± 0.021 | 1.42 ± 0.05 |
| With adiabatic expansion (Control) | 322.5 ± 109.2 | 1.68 ± 0.04 |
| P value | <0.0001 | 0.0022 |

The results confirmed that there was a difference (P-value<0.0001) between the two groups. T-test on CMD of supermicron particles also proved that adiabatic expansion enlarged particles. Although the fraction of particles larger than 3 μm was negligible, this does not necessarily mean that 3 μm was the upper-limit of the particle enlargement. Due to gravitational settling, larger particles might have settled (on the inner surface of the expansion bag or tubing) before reaching the OPC. In addition, the instant expansion process causes turbulence inside the bag, which is conducive to the deposition of larger particles by impaction (Robertson & Goldreich, 2012). In other words, there may be constraints in the current system for accurate measurement of aerosol particles larger than a few microns.

Figure 26B:
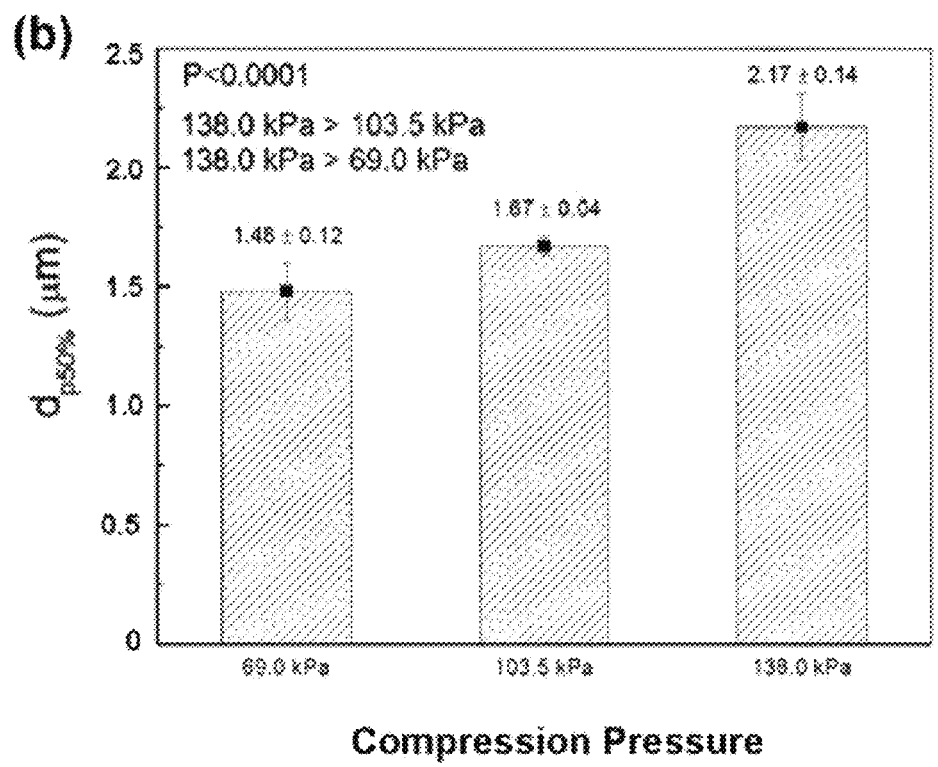

One-way ANOVA results on compression pressures are displayed in FIGS. 26(a)-26(b). An increase in the number concentration of the supermicron particles with an increase in compression pressure was observed. A 10-fold increase in number concentration was achieved by increasing the compression pressure, for example from 69.0 kPa to 138.0 kPa (FIG. 26(a)). CMD also increased from ~1.48 μm to ~2.17 μm (FIG. 26(b)). A higher compression pressure can provide a higher supersaturation ratio, leading to a lower temperature after the C/E cycle. The lower temperature can enable more water vapor condensation onto the particles, thus a higher number of the nanosized particles undergoing the size amplification.

Number of C/E Cycles

Figure 27A:
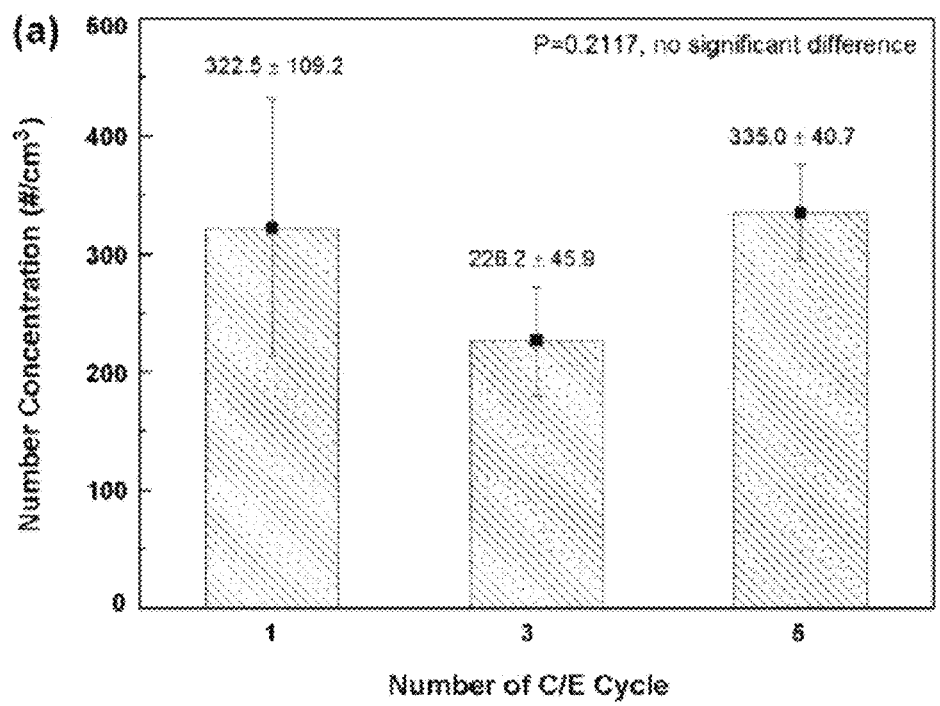
FIGS. 27(a)-(b) illustrate a comparison of particle number concentration and CMD of supermicron particles under 3 numbers of C/E cycles.
Figure 27B:
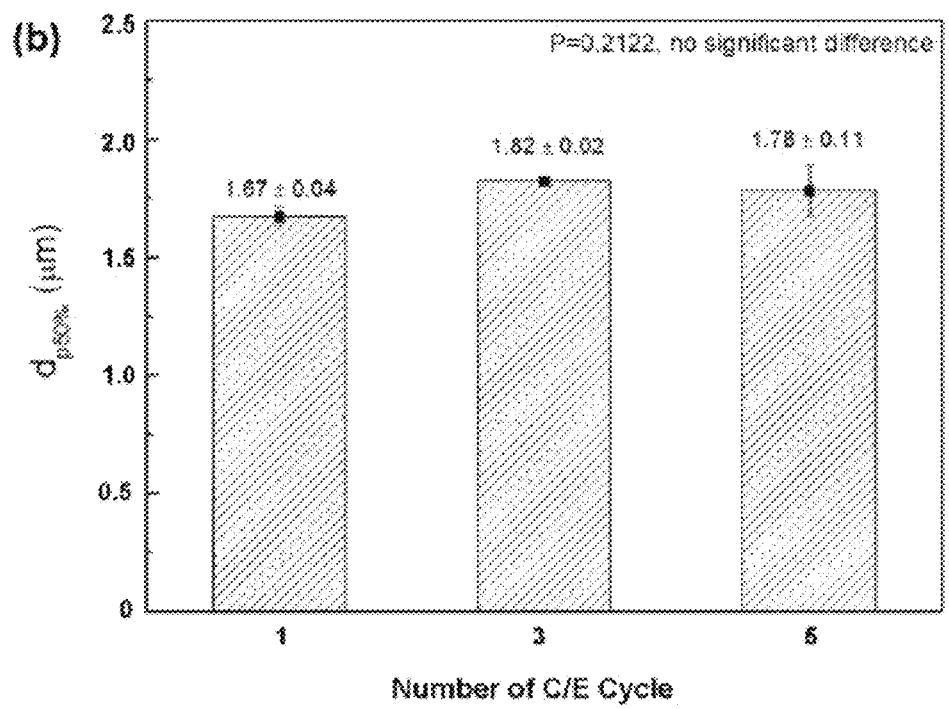

One-Way ANOVA test results as shown in FIGS. 27(a)-27(b) reveal no statistically significant difference in number concentration or CMD within the three groups (p-value ~0.21). After the first C/E cycle, thermodynamic equilibrium inside the bag may have been reached. While more C/E cycles were originally hypothesized to provide more water vapor for size amplification, the experimental results indicate that when the next cycle of compression applied, work was done to the aerosol, causing re-evaporation of the water from the amplified aerosol in the bag. Thus, a higher number of the C/E cycles simply repeated the first cycle and exerted no observed net effect on amplification.

DI Water Temperature

Figure 28A:
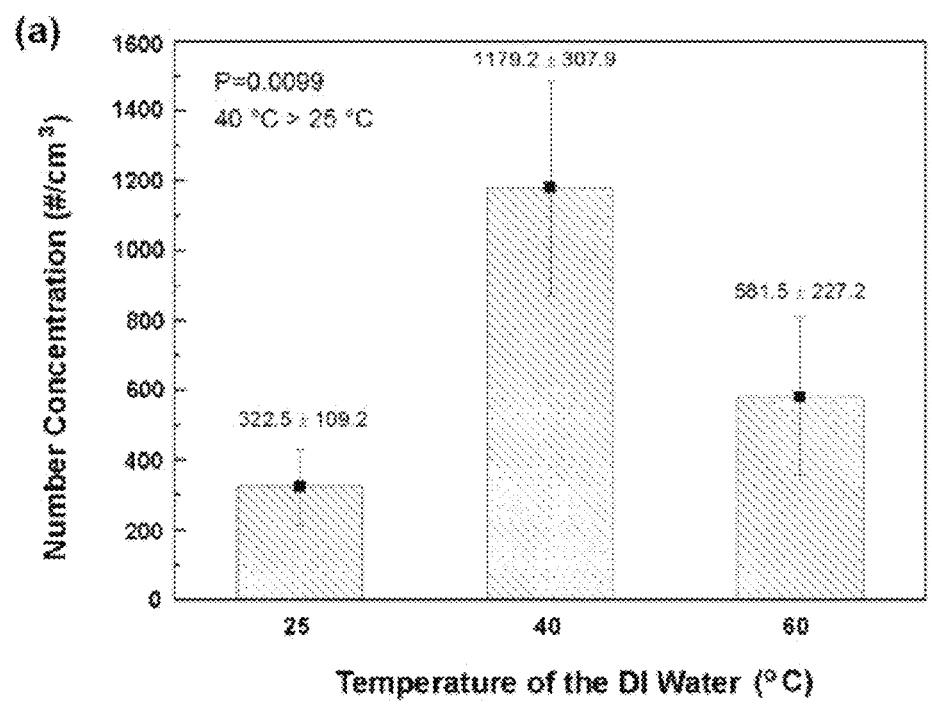
FIGS. 28(a)-(b) show a comparison of particle number concentration and CMD of supermicron particle under 3 water temperature levels.
Figure 28B:
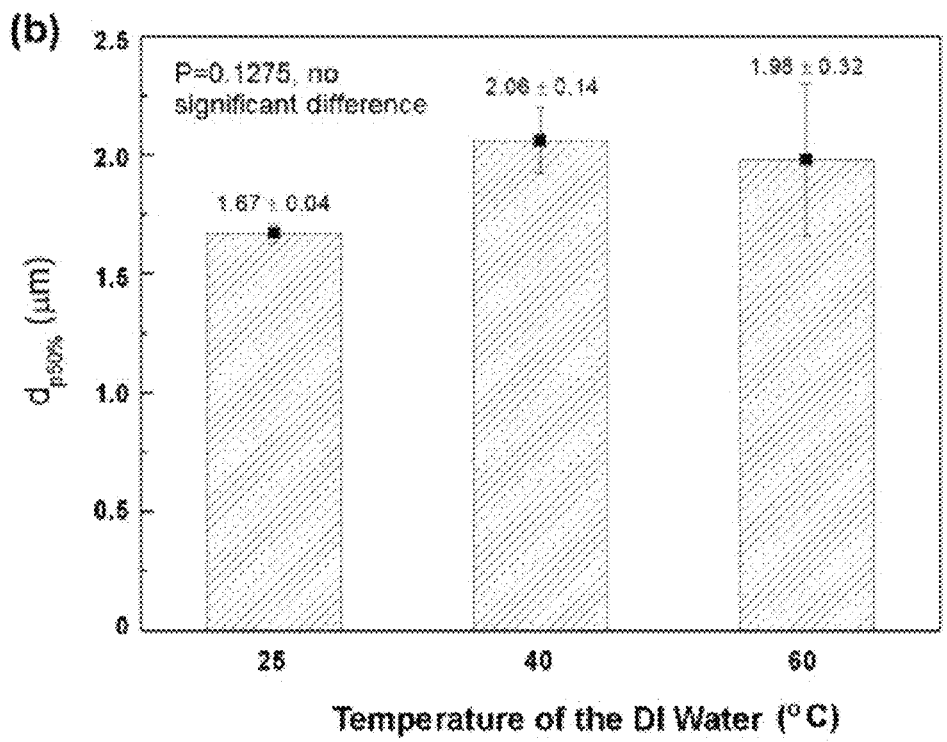

As shown in FIG. 28(a), an increase in the number concentration was observed when the DI water temperature increased from 25° C. to 40° C. However, the number concentration for the size range of study decreased when the DI water temperature increased further to 60° C. The results of 1-Way ANOVA test also confirm that the experiment run at 40° C. had the greatest size amplification potency among these three temperatures. No obvious difference among the CMD of these three groups is seen (FIG. 28(b)). A higher temperature was expected to produce more supermicron particles as it would yield a higher moisture content available for condensation. One possible reason for a lower number concentration at 60° C. is that at this higher temperature, the stability of virus capsid may have reduced, which might have led to the structure alteration of virion protein (a complete virus particle) and finally affected the hydrophobicity for MS2 aerosol (Pinto et al., 2010).

Viability Preservation

The MS2 titer in the Collison nebulizer reservoir was 1.5 (±0.32)×10$^9$ PFU/mL, thereby implying the system supplied a stable size distribution of the aerosol source for different experiments. The consumption rate of MS2 suspension in the Collison nebulizer was about 0.3 mL/min, and the bag filling time was set at 10 s for each experiment. Consequently, the consumed volume of the nebulizer liquid was about 0.05 mL, and accordingly the expected MS2 titer in the sampling air was estimated to be ~7.5×10$^7$ PFU/L of air, assuming no loss due to transport or inactivation by the nebulization process. Detailed results for each system parameter investigated are reported in the following subsections.

Compression Pressure

Figure 29A:
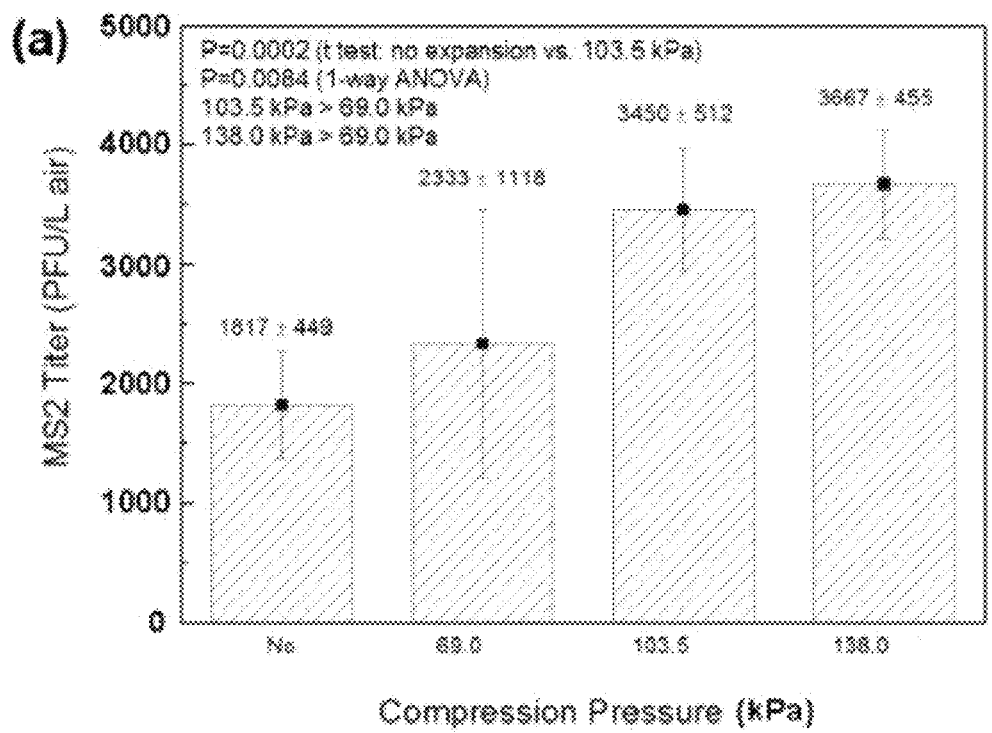
FIGS. 29(a)-(d) demonstrate a comparison of MS2 titer in the BASIC sampler with variation of four factors.

Results of the statistical analyses are displayed in FIG. 29(a), which shows the viable MS2 aerosol collected after going through the adiabatic process for size amplification. FIG. 29(a) displays the viable MS2 titer collected as a function of compression pressure (for inducing adiabatic expansion). As the pressure increased, the viable count increased. FIG. 29(c) illustrates one compression/expansion cycle to be the optimal condition. FIG. 29(c) illustrates that the viable count increased as temperature increased, although at high temperature (60° C.) some MS2 got deactivated. FIG. 29(d) shows that the amplification process was very fast and additional dwell time was not needed to enhance the performance.

FIG. 29(a), shows an increasing trend of collected viable MS2 with an increase in the compression pressure up to 103.5 kPa. Shaking amplified aerosol trapped inside the expansion bag increased the total gain of the aerosol and probability of virus deposition into the DI water. The results indicate the viability was preserved well in the range of compression pressure investigated (69.0-138.0 kPa). Past studies showed that application of a high pressure on a virus-contained suspension can kill noroviruses (Aertsen et al., 2009). However, this concern applies to an extremely high pressure (>60,000 psi) wherein virus capsid protein or lipid envelope may break (Tang et al., 2010). By using MS2 as a surrogate at a high pressure (40,000 psi), Pan (2015) observed that MS2 did not suffer significant viability loss under that pressure held for 3 min. Our statistical analysis results infer that the collection of viable MS2 after adiabatic expansion achieved a statistically significant increase than the case without adiabatic expansion, and the collected amount increased as compression pressure increased up to 103.5 kPa. There was no statistically significant difference between cases with compression pressures of 103.5 kPa and of 138.0 kPa.

Number of C/E Cycles

Figure 29B:
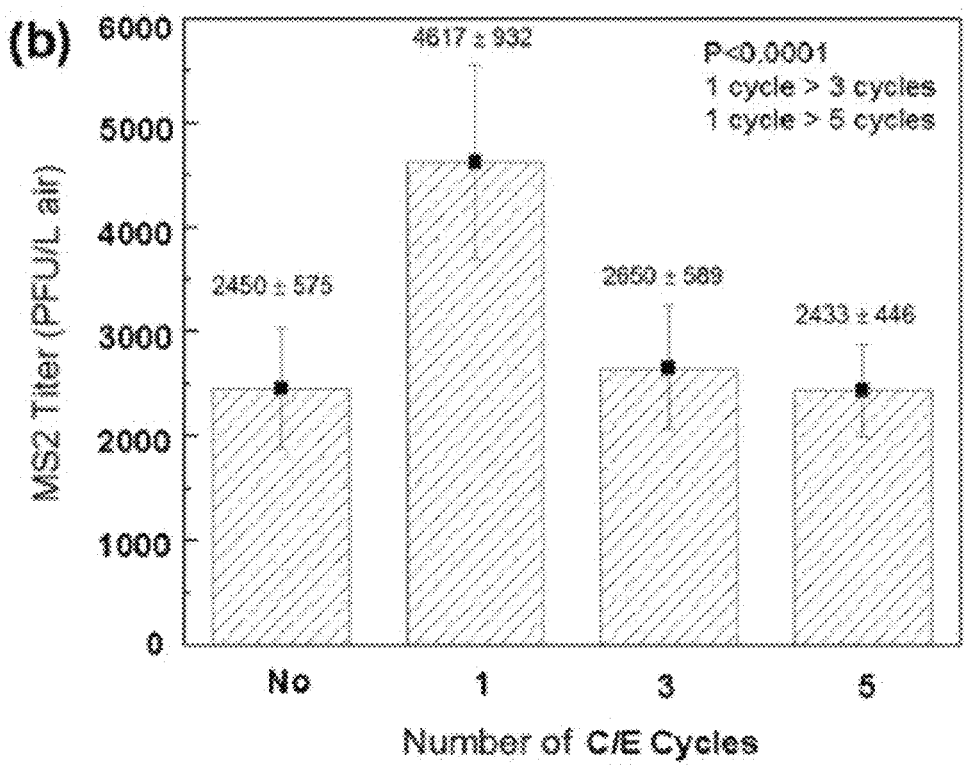
Figure 29C:
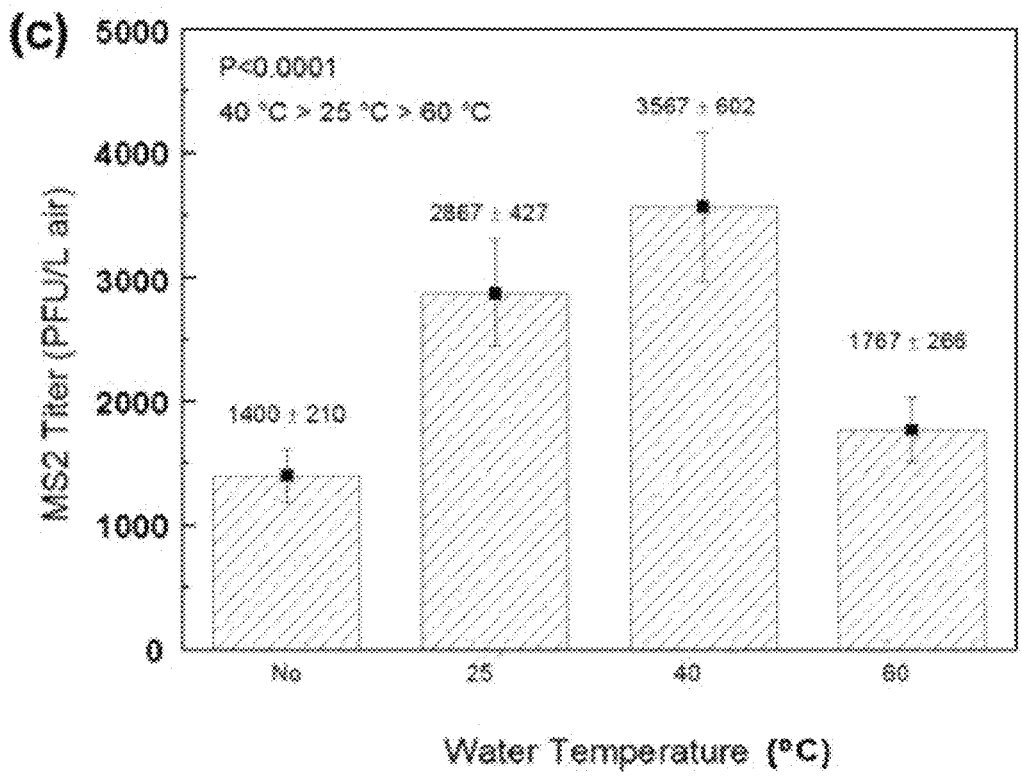
Figure 29D:
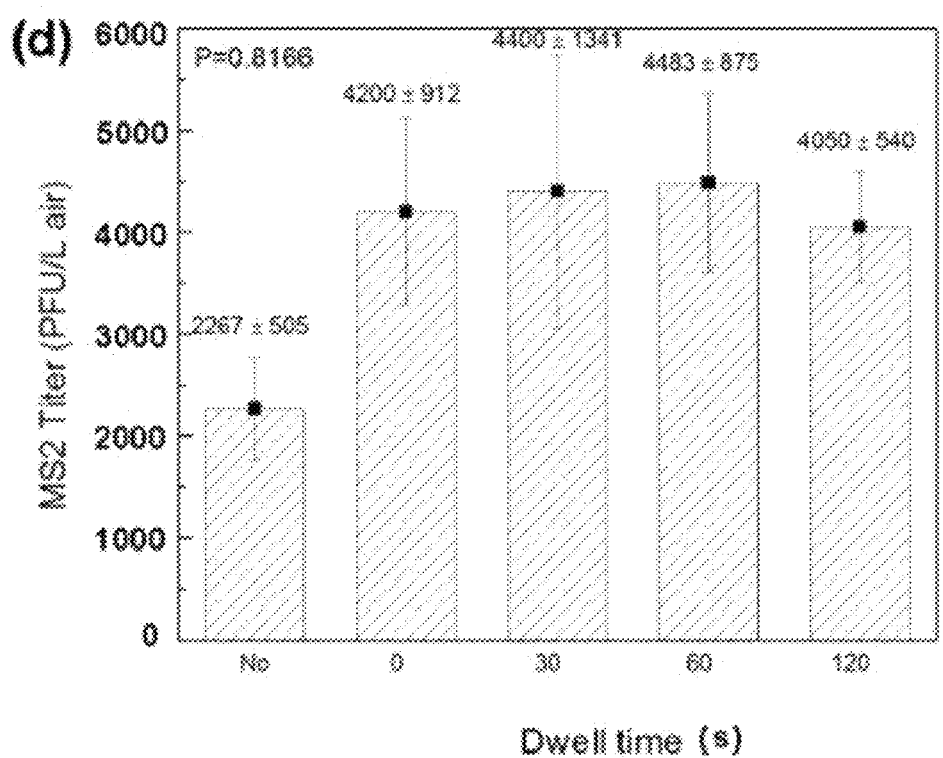

Comparative results of collected viable MS2 under different numbers of C/E cycles are presented in FIG. 29(b). In contrast to the physical size amplification, a higher number of cycles may be inversely related to the viability preservation of MS2. Pollard (1960) reported that gradual exertion of pressure onto viruses leads to an increase of bond stability in virion protein, thus leading to the better stabilization of virus. However, exertion of an instant pressure loss (as in adiabatic expansion) may cause viruses to lose the antigenic surface and break apart. In other words, when the number of C/E cycles increases, viruses may suffer from frequent and instant pressure changes, which can cause virions to expand and break apart. As seen in FIG. 29(b), the highest viable virus titer (4620±930 PFU/L air) was achieved at one C/E cycle, and the difference from other groups (3 cycles, 5 cycles, and no adiabatic expansion) was statistically significant. Taking the results of compression pressure together into consideration, it can be concluded that MS2 may have a high endurance to pressure, yet low resistance to frequent pressure change. Hence, when using the BASIC for collection of viable MS2, one C/E cycle can provide the optimal outcome.

DI Water Temperature

Collected viable MS2 as a function of the temperature of pre-injected water is plotted in FIG. 29(c). In operating the BASIC, DI water was used as a medium for both condensation and collection, although other media may be used.

When applying DI water of 40° C., an increase of viable MS2 collected in water was observed in comparison to the case with DI water of 25° C. However, when the water temperature increased further to 60° C., the titer of viable MS2 collected in water decreased greatly. This was likely due to inactivation of MS2 by hot water beyond the comfort zone of MS2. Previous studies found that temperature can play a vital role in the viability of many viruses (Ausar et al., 2006). Pinto et al. (2010) investigated the effect of temperature on MS2, and reported that high temperatures can cause structural change of virion capsid and therefore virus inactivation. One-way ANOVA results confirm that by applying water temperature of 40° C., the titer of collected viable MS2 was higher than those at 25° C. and 60° C. Different from other key parameters, higher water temperature may exert positive effect on physical size amplification but negative effect on viability preservation. As MS2 shows vulnerability to 60° C., therefore 40° C. is the optimal DI water temperature, considering both physical collection and viability preservation.

Dwell Time

There was no benefit for increasing the dwell time since the viable MS2 titer did not vary much among the four dwell times studied (see FIG. 29(d)). This is confirmed by the 1-Way ANOVA test showing no statistically significant difference among the four dwell time groups. C.-Y. Wu and Biswas (1998) reported that the growth of an aerosol particle in the free molecular regime due to condensation was independent of its original size, and it could achieve 50% of its final size at ~3 characteristic times. When the number concentration of ultrafine particles was above $10^4$ #/cm$^3$, the characteristic time was less than 0.3 s. In other words, in a short period of time (less than 1 s), ultrafine particles could grow to 50% of its final size (calculated as ~10 μm). Hence, a long dwell time for particle growth may not be essential (neither for particle amplification nor for more virus collection in this given system).

Comparison with SKC® BioSampler

The SKC® BioSampler is a commercially available sampler commonly used in bioaerosol studies. Many studies have illustrated its good efficiency for collecting supermicron particles, e.g., bacteria and fungi (Kesavan et al., 2010; Lin et al., 1999; Y. Wu et al., 2010), although its efficiency for virus aerosols below 100 nm is unsatisfactory (<10%) (Hogan, et al., 2005). Fabian et al. (2009) used a titer of $1.9 \times 10^{10}$ FFU (virus focus forming unit)/mL in the original suspension of influenza virus in the nebulizer reservoir and achieved the titer of ~400 FFU/L air in collected sample from the BioSampler. Pan et al. (2016) also used MS2 as test virus aerosol, and obtained a result of only ~10 PFU/L air from the BioSampler by using an original titer of $10^9$ PFU/mL in the Collison nebulizer. Compared to these results, the BASIC has achieved up to >4,000 PFU/L air under the optimal conditions (i.e. compression pressure of 138.0 kPa, 1 C/E cycle and DI water temperature of 40° C.; no additional dwell time applied).

Transport and nebulization can cause a major viability loss of produced MS2 aerosol. (Thompson and Yates (1999)) reported that MS2 suffered a great viability loss when a triple-phase-boundary (TPB, the interface of gas, liquid and solid) existed. The shear force established in the nebulization process can easily damage the viruses in the TPB. As mentioned before, the titer of MS2 in the produced aerosol was estimated to be ~$7.5 \times 10^7$ PFU/L air. Thus, based on the measured MS2 titer in the Collison nebulizer reservoir, the collection efficiency in the BASIC was only ~0.005%. However, it is still much higher when compared with the collection efficiency of the BioSampler (<0.0001%) (Pan, et al., 2016); the BASIC can collect 50 times more under optimal conditions over the BioSampler.

Conclusions

The present example focused on the performance assessment of the BASIC in enabling ultrafine virus aerosol sampling as well as the ability in preserving the viability of airborne virus. MS2 phage was used as the test agent in assessing both amplification effectiveness and viability preservation. Results for physical size amplification tests showed that increasing compression pressure in the range of 69.0-138.0 kPa had a positive effect on the CMD enlargement and increase of aerosol number concentration. This can be attributed to the higher saturation ratio at higher compression pressure. The application of C/E cycles yielded physical size amplification, and 3 cycles can be the optimal condition. Water temperature had a double-edged effect on MS2 aerosol. Increasing water temperature from 25° C. to 40° C. resulted in a positive effect, but it exhibited a negative effect as temperature increased from 40° C. to 60° C. This phenomenon might be due to the structural change of capsid protein of MS2 virion, which reduced MS2's ability to attract water vapor.

In evaluating the performance of viability preservation, the results showed that increasing compression pressure also produced an improvement in the total amount of collected MS2 in DI water, and the range of compression pressure applied in this study reflected a negligible effect on the viability of MS2 virus. Regarding the number of C/E cycles, applying one single cycle was can be optimal for collecting viable virus aerosol in the expansion bag as multiple C/E cycles induced a great virus viability loss. This reflected that MS2 might not be resistant to frequent pressure swing. Similar to the results in the physical size amplification, 40° C. water temperature increased the amount of collected viable MS2 virus, while 60° C. water temperature sampled much less. The results are in agreement with previous research wherein high temperature above a threshold value could alter the structure of virus capsid protein, leading to inactivation of viruses. Increasing dwell time from 0 s to 120 s yielded little to no obvious difference in the titer of viable MS2.

In conclusion, the BASIC system showed its potential in highly efficient sampling of ultrafine virus aerosols. When the BASIC is combined with a rapid airborne virus detection and analysis approaches, the resulting system could be a significantly improved virus aerosol detection and identification system for infection control, agriculture, research, and biodefense applications.

REFERENCES

Aertsen, A., Meersman, F., Hendrickx, M. E., Vogel, R. F., & Michiels, C. W. (2009). Biotechnology under high pressure: applications and implications. *Trends in Biotechnology*, 27, 434-441.

Aitken, J. (1888). On the number of dust particles in the atmosphere. *Nature*, 37, 428-430.

Alonso, C., Raynor, P. C., Davies, P. R., & Torremorell, M. (2015). Concentration, Size Distribution, and Infectivity of Airborne Particles Carrying Swine Viruses. *PLoS One*, 10, e0135675.

Ausar, S. F., Foubert, T. R., Hudson, M. H., Vedvick, T. S., & Middaugh, C. R. (2006). Conformational stability and disassembly of Norwalk virus-like particles effect of pH and temperature. *Journal of Biological Chemistry*, 281, 19478-19488.

Bailyn, M. (1994). *A survey of thermodynamics*. American Institute of Physics.

Brankston, G., Gitterman, L., Hirji, Z., Lemieux, C., & Gardam, M. (2007). Transmission of influenza A in human beings. *The Lancet Infectious Diseases*, 7, 257-265.

Cormier, J., & Janes, M. (2014). A double layer plaque assay using spread plate technique for enumeration of bacteriophage MS2. *Journal of Virological Methods*, 196, 86-92.

Davis, J. E., Sinsheimer, R. L., & Strauss, J. H. (1961). Bacteriophage MS2: another RNA phage. *Science*, 134, 1427.

Dawson, D., Paish, A., Staffell, L., Seymour, I., & Appleton, H. (2005). Survival of viruses on fresh produce, using MS2 as a surrogate for norovirus. *Journal of Applied Microbiology*, 98, 203-209.

Fabian, P., McDevitt, J., Houseman, E., & Milton, D. (2009). Airborne influenza virus detection with four aerosol samplers using molecular and infectivity assays: considerations for a new infectious virus aerosol sampler. *Indoor Air*, 19, 433-441.

Goldmann, D. A. (2000). Transmission of viral respiratory infections in the home. *The Pediatric Infectious Disease Journal*, 19, S97-S102.

Hering, S. V., Spielman, S. R., & Lewis, G. S. (2014). Moderated, Water-Based, Condensational Particle Growth in a Laminar Flow. *Aerosol Science and Technology*, 48, 401-408.

Hering, S. V., & Stolzenburg, M. R. (2005). A method for particle size amplification by water condensation in a laminar, thermally diffusive flow. *Aerosol Science and Technology*, 39, 428-436.

Hogan, C., Kettleson, E., Lee, M. H., Ramaswami, B., Angenent, L., & Biswas, P. (2005). Sampling methodologies and dosage assessment techniques for submicrometre and ultrafine virus aerosol particles. *Journal of Applied Microbiology*, 99, 1422-1434.

Kesavan, J., Schepers, D., & McFarland, A. R. (2010). Sampling and retention efficiencies of batch-type liquid-based bioaerosol samplers. *Aerosol Science and Technology*, 44, 817-829.

Kousaka, Y., Niida, T., Okuyama, K., & Tanaka, H. (1982). Development of a mixing type condensation nucleus counter. *Journal of Aerosol Science*, 13, 231-240.

Lapinsky, S. E. (2010). Epidemic viral pneumonia. *Current Opinion in Infectious Diseases*, 23, 139-144.

Lednicky, J., Pan, M., Loeb, J., Hsieh, H., Eiguren-Fernandez, A., Hering, S., Fan, Z. H., & Wu, C.-Y. (2016). Highly efficient collection of infectious pandemic influenza H1N1 virus (2009) through laminar-flow water based condensation. *Aerosol Science and Technology*, 50, i-iv.

Lin, X., Reponen, T. A., Willeke, K., Grinshpun, S. A., Foarde, K. K., & Ensor, D. S. (1999). Long-term sampling of airborne bacteria and fungi into a non-evaporating liquid. *Atmospheric Environment*, 33, 4291-4298.

Liu, B., Pui, D., Agarwal, J., McKenzie, R., Pohl, F., Preining, O., Reischl, G., Szymanski, W., & Wagner, P. (1984). Measurements of Kelvin-equivalent size distributions of well-defined aerosols with particle diameters>13 nm. *Aerosol Science and Technology*, 3, 107-115.

Miller, S., & Bodhaine, B. (1982a). Calibration of Pollak condensation nuclei counters using charged, monodisperse aerosols. *Journal of Aerosol Science*, 13, 419-428.

Miller, S., & Bodhaine, B. (1982b). Supersaturation and expansion ratios in condensation nuclei counters: an historical perspective. *Journal of Aerosol Science*, 13, 481-490.

Milton, D. K., Fabian, M. P., Cowling, B. J., Grantham, M. L., & McDevitt, J. J. (2013). Influenza virus aerosols in human exhaled breath: particle size, culturability, and effect of surgical masks. *PLoS Pathog*, 9, e1003205.

Oh, S., Anwar, D., Theodore, A., Lee, J.-H., Wu, C.-Y., & Wander, J. (2010). Development and evaluation of a novel bioaerosol amplification unit (BAU) for improved viral aerosol collection. *Journal of Aerosol Science*, 41, 889-894.

Otter, J., Donskey, C., Yezli, S., Douthwaite, S., Goldenberg, S., & Weber, D. J. (2016). Transmission of SARS and MERS coronaviruses and influenza virus in healthcare settings: the possible role of dry surface contamination. *Journal of Hospital Infection*, 92, 235-250.

Pan, H. (2015). *Virus inactivation in contaminated fruit puree and juice via hydrostatic pressure process* (Thesis). Illinois Institute of Technology.

Pan, M., Eiguren-Fernandez, A., Hsieh, H., Afshar-Mohajer, N., Hering, S. V., Lednicky, J., Hugh Fan, Z., & Wu, C. Y. (2016). Efficient collection of viable virus aerosol through laminar-flow, water-based condensational particle growth. *Journal of Applied Microbiology*, 120, 805-815.

Pease, L. F. (2012). Physical analysis of virus particles using electrospray differential mobility analysis. *Trends in Biotechnology*, 30, 216-224.

Pinto, F., Maillard, J.-Y., & Denyer, S. P. (2010). Effect of surfactants, temperature, and sonication on the virucidal activity of polyhexamethylene biguanide against the bacteriophage MS2. *American Journal of Infection Control*, 38, 393-398.

Pollak, L., & Metnieks, A. (1960). Intrinsic calibration of the photo-electric condensation nucleus counter model 1957 with convergent light-beam. In (Edited Editor), Book *Intrinsic calibration of the photo-electric condensation nucleus counter model 1957 with convergent light-beam*. Technology Note No. 9, School of Cosmic Physics, Dublin Institute for Advanced Studies, Dublin, Ireland, City.

Pollak, L., & O'connor, T. (1955). A photo-electric condensation nucleus counter of high precision. *Geofisica Pura e Applicata*, 32, 139-146.

Pollard, E. C. (1960). Theory of the physical means of the inactivation of viruses. *Annals of the New York Academy of Sciences*, 83, 654-660.

Robertson, B., & Goldreich, P. (2012). Adiabatic heating of contracting turbulent fluids. *The Astrophysical Journal Letters*, 750, 1-5.

Strey, R., Schmeling, T., & Wagner, P. (1986). The effect of the heat of association on homogeneous nucleation rates in methanol vapor. *Journal of Chemical Physics*, 85, 6192-6196.

Tang, Q., Li, D., Xu, J., Wang, J., Zhao, Y., Li, Z., & Xue, C. (2010). Mechanism of inactivation of murine norovirus-1 by high pressure processing. *International Journal of Food Microbiology*, 137, 186-189.

Thompson, S. S., & Yates, M. V. (1999). Bacteriophage inactivation at the air-water-solid interface in dynamic batch systems. *Applied and Environmental Microbiology*, 65, 1186-1190.

USEPA (1984). USEPA manual of methods for virology, Chapter 16. In (Edited Editor), Book *USEPA manual of methods for virology*, Chapter 16. Environmental Monitoring and Support Laboratory, Office of Research and Development, US Environmental Protection Agency Cincinnati, OH.

Vanhanen, J., Mikkilä, J., Lehtipalo, K., Sipilä, M., Manninen, H., Siivola, E., Petäjä, T., & Kulmala, M. (2011). Particle size magnifier for nano-CN detection. *Aerosol Science and Technology*, 45, 533-542.

Wang, Y. (2013). The H7N9 influenza virus in China—changes since SARS. *New England Journal of Medicine*, 368, 2348-2349.

Wu, C.-Y., & Biswas, P. (1998). Particle growth by condensation in a system with limited vapor. *Aerosol Science and Technology*, 28, 1-20.

Wu, Y., Shen, F., & Yao, M. (2010). Use of gelatin filter and BioSampler in detecting airborne H5N1 nucleotides, bacteria and allergens. *Journal of Aerosol Science*, 41, 869-879.

Yu, I. T., Li, Y., Wong, T. W., Tam, W., Chan, A. T., Lee, J. H., Leung, D. Y., & Ho, T. (2004). Evidence of airborne transmission of the severe acute respiratory syndrome virus. *New England Journal of Medicine*, 350, 1731-1739.

Zuo, Z., Kuehn, T. H., Bekele, A. Z., Mor, S. K., Verma, H., Goyal, S. M., Raynor, P. C., & Pui, D. Y. (2014). Survival of airborne MS2 bacteriophage generated from human saliva, artificial saliva, and cell culture medium. *Applied and Environmental Microbiology*, 80, 2796-2803.

Example 8

TABLE 3

SARS-CoV-2 N-gene rRT-PCR primers and probe that can be utilized with detection assays, systems, and methods as described herein for SARS-CoV-2 detection.

| Primer/probe name | Description | Oligonucleotide sequence (5' to 3') | Label |
|---|---|---|---|
| Led-N-F | SARS CoV-2 N Forward Primer | 5'-GGGAGCAGAGGCGGCAGTCAAG-3' (SEQ ID NO: 1) | None |
| Lef-N-R | SARS CoV-2 N Reverse Primer | 5'-CATCACCGCCATTGCCAGCCATTC-3' (SEQ ID NO: 2) | None |
| Led-N-Probe[a] | SARS CoV-2 N Probe | 5'FAM-CCTCATCACGTAGTCGCAACAGTTC-BHQ1-3' (SEQ ID NO: 3) | FAM, BHQ1 |

[a]Tis TaqMan ® probe is 5'-end labeled with the reporter molecule 6-carboxyfluorescein (FAM) and with quencher Black Hole Quencher 1 (BHQ-1) at the 3'-end.

Example 9

TABLE 4

Additional sequences of RT-LAMP primers for SARS-CoV-2 detection targeting the N gene that can be utilized by detection assays, systems, and methods as described herein.

| Primers | Primer sequence (5'-3') | SEQ ID NO: |
|---|---|---|
| F3 | TGGACCCCAAAATCAGCG | SEQ ID NO: 4 |
| B3 | AGCCAATTTGGTCATCTGGA | SEQ ID NO: 5 |
| FIP | CGTTGTTTTGATCGCGCCCCATTACGTTTGGTGGACCCTC | SEQ ID NO: 6 |
| BIP | ATACTGCGTCTTGGTTCACCGCATTGGAACGCCTTGTCCTC | SEQ ID NO: 7 |

TABLE 4-continued

Additional sequences of RT-LAMP primers for SARS-CoV-2 detection targeting the N gene that can be utilized by detection assays, systems, and methods as described herein.

| Primers | Primer sequence (5'-3') | SEQ ID NO: |
|---|---|---|
| LF | TGCGTTCTCCATTCTGGTTACT | SEQ ID NO: 8 |
| LB | TCTCACTCAACATGGCAAGGAA | SEQ ID NO: 9 |

FIP stands for Forward Inner Primer;
BIP stands for Backward Inner Primer;
LF and LB are the forward and backward loop primers

Example 10

TABLE 5

Additional sequences of RT-LAMP primers for H1N1 flu virus detection according to detection assays, systems, and methods as described herein.

| Primer | Sequence (5'-3') |
|---|---|
| F3 | ACCTTCTAGAAGACAAGCATAA (SEQ ID NO: 10) |
| B3 | TCCTCATAATCGAT (SEQ ID NO: 11) |
| FIP | TGGATTTCCCAGGATCCAGCGG AAACTATGCAAACTAAGAGG (SEQ ID NO: 12) |
| BIP | TCCACAGCAAGCTCATGGTCTC CTGGGTAACACGTTCC (SEQ ID NO: 13) |
| LF | CCAAATGCAATGGGGCTAC (SEQ ID NO: 14) |
| LB | CTACATTGTGGAAACATCTAGT TCAG (SEQ ID NO: 15) |

FIP stands for Forward Inner Primer;
BIP stands for Backward Inner Primer;
LF and LB are the forward and backward loop primers.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to the values and/or measuring techniques. In addition, the phrase "about 'x' to 'y'" includes "about 'x' to about 'y'".

Many variations and modifications may be made to the above-described embodiments. All such modifications and variations are intended to be included herein within the scope of this disclosure and protected by the following claims.

At least the following is claimed:

1. A bioaerosol amplification and detection system, comprising:
   a bioaerosol amplification unit comprising a chamber configured to receive air containing bioaerosols, wherein the chamber is further configured for adiabatic amplification of the bioaerosols;
   wherein the air containing bioaerosols is cooled by a temperature drop within the chamber of the bioaerosol amplification unit, wherein the temperature drop is controlled by the ratio of the pressure of the air containing bioaerosols after adiabatic expansion to the pressure of the air containing bioaerosols before adiabatic expansion;
   a biosampler, wherein the biosampler is in fluid communication with the bioaerosol amplification unit, wherein the biosampler is configured to receive and collect adiabatically amplified bioaerosols from the chamber of the bioaerosol amplification unit; and
   a bioaerosol analysis platform, wherein the bioaerosol analysis platform is configured to receive adiabatically amplified bioaerosols collected in the biosampler and configured to detect the adiabatically amplified bioaerosols by one or more bioaerosol detection assays, wherein the one or more bioaerosol detection assays comprise at least one coronavirus detection assay, at least one influenza detection assay, or both.

2. The bioaerosol amplification and detection system of claim 1, wherein the adiabatic amplification is adiabatic cooling.

3. The bioaerosol amplification and detection system of claim 2, wherein the adiabatic cooling further comprises swirling, mixing, or both.

4. The bioaerosol amplification and detection system of claim 1, wherein at least one coronavirus detection assay is a SARs-CoV-2, a MERS-CoV, a HCoV-229E, a HCoV-OC43, a HCoV-NL64, or a HCoV-HKU1 detection assay.

5. The bioaerosol amplification and detection system of claim 1, wherein at least one influenza detection assay is a type A influenza virus, a type B influenza virus, a type C influenza virus, a type D influenza virus, or a H1N1 detection assay.

6. The bioaerosol amplification and detection system of claim 1, wherein the bioaerosol analysis platform is a microfluidic device comprising one or more bioaerosol detection assays configured to detect the adiabatically amplified bioaerosols.

7. The bioaerosol amplification and detection system of claim 1, wherein the bioaerosol amplification unit further comprises one or more interior surfaces of the chamber wetted with water having a temperature of about 35° C. to about 65° C., wherein the one or more surfaces is adjacent to the air containing bioaerosols.

8. The bioaerosol amplification and detection system of claim 1, wherein the chamber further comprises cooled air containing bioaerosols having a temperature of about −40° C. to about 10° C. and steam having a temperature of about 35° C. to about 65° C.

9. The bioaerosol amplification and detection system of claim 1, wherein the chamber further comprises cooled air having a flow rate of about 0.1 Liters/min to about 10 Liters/min and steam having a flow rate of about 1 Liters/min to about 50 Liters/min.

10. The bioaerosol amplification and detection system of claim 6, wherein the microfluidic device is paper-based or laminated paper-based.

11. The bioaerosol amplification and detection system of claim 1, wherein the one or more detection assays comprise an immunoassay or a nucleic acid amplification assay, individually or in combination.

12. The bioaerosol amplification and detection system of claim 1, wherein the chamber is configured so that the volume of the chamber can be reduced by compression and expanded by decompression.

13. The bioaerosol amplification and detection system of claim 1, wherein the biosampler is functionally integrated into the chamber of the bioaerosol amplification unit and the chamber is configured for collection of amplified bioaerosols.

14. A method of detecting amplified bioaerosols, comprising the steps of:
   providing a bioaerosol amplification and detection system comprising a bioaerosol amplification unit, a biosampler, and a bioaerosol analysis platform;
   delivering air containing or suspected of containing bioaerosols to the bioaerosol amplification unit, wherein the bioaerosol amplification unit is configured to adiabatically amplify bioaerosols, wherein the bioaerosols are or are suspected to be coronavirus particles, influenza particles, or both;

adiabatically amplifying bioaerosols with the bioaerosol amplification unit;

delivering amplified bioaerosols from the bioaerosol amplification unit to the biosampler;

precipitating, concentrating, or both the amplified bioaerosols into a collection reservoir of the biosampler;

delivering the collected amplified bioaerosols from the collection reservoir of the biosampler to a bioaerosol analysis platform, wherein the bioaerosol analysis platform is configured to detect one or more collected amplified bioaerosols or components thereof with one or more detection assays;

detecting collected amplified bioaerosols or bioaerosol components with one or more detection assays; and wherein the air containing bioaerosols is cooled by a temperature drop within the bioaerosol amplification unit, wherein the temperature drop is controlled by the ratio of the pressure of the air containing bioaerosols after adiabatic expansion to the pressure of the air containing bioaerosols before adiabatic expansion.

15. The method of claim 14, wherein the one or more detection assays is a nucleic acid detection assay or an immunoassay, individually or in combination.

16. The method of claim 14, wherein the collection reservoir of the biosampler further comprises a collection media.

17. The method of claim 14, wherein the air containing bioaerosols is cooled within a chamber of the bioaerosol amplification unit, wherein the chamber of the bioaerosol amplification unit has one or more interior surfaces adjacent to the air containing bioaerosols, wherein one or more surfaces are wetted with warm water.

18. The method of claim 14, wherein the coronavirus particles are SARs-COV-2 particles, MERS-CoV particles, HCoV-229E particles, HCoV-OC43 particles, HCoV-NL64 particles, or HCoV-HKU1 particles, individually or in combination.

19. The method of claim 14, wherein the influenza particles are type A influenza virus, type B influenza virus, type C influenza virus, type D influenza virus, or H1N1 particles, individually or in combination.

20. The method of claim 15, wherein the nucleic detection assay is real-time reverse-transcriptase polymerase chain reaction or reverse transcription loop-mediated isothermal amplification.

* * * * *